(12) United States Patent
Roulston et al.

(10) Patent No.: US 8,173,677 B2
(45) Date of Patent: May 8, 2012

(54) COMPOSITIONS AND METHODS FOR EFFECTING NAD+ LEVELS USING A NICOTINAMIDE PHOSPHORIBOSYL TRANSFERASE INHIBITOR

(75) Inventors: Anne Roulston, Montreal (CA); Pierre Beauparlant, Montreal (CA)

(73) Assignee: Gemin X Pharmaceuticals Canada Inc., Montreal (CA)

( * ) Notice: Subject to any disclaimer, the term of this patent is extended or adjusted under 35 U.S.C. 154(b) by 448 days.

(21) Appl. No.: 12/410,930

(22) Filed: Mar. 25, 2009

(65) Prior Publication Data

US 2009/0215823 A1 Aug. 27, 2009

Related U.S. Application Data

(63) Continuation-in-part of application No. 12/237,755, filed on Sep. 25, 2008.

(60) Provisional application No. 60/975,488, filed on Sep. 26, 2007, provisional application No. 61/020,290, filed on Jan. 10, 2008.

(51) Int. Cl.
*A61K 31/4545* (2006.01)
*A61K 31/4425* (2006.01)
*A61P 35/02* (2006.01)

(52) U.S. Cl. .......................... 514/318; 514/352
(58) Field of Classification Search .................. 514/318, 514/352
See application file for complete search history.

(56) References Cited

U.S. PATENT DOCUMENTS

| | | | |
|---|---|---|---|
| 3,710,795 A | 1/1973 | Higuchi et al. | |
| 5,262,564 A | 11/1993 | Kun et al. | |
| 5,563,160 A | 10/1996 | Bramm et al. | |
| 5,696,140 A | 12/1997 | Bramm et al. | |
| 6,525,077 B2 | 2/2003 | Binderup et al. | |
| 7,253,193 B2 | 8/2007 | Binderup et al. | |

FOREIGN PATENT DOCUMENTS

| | | |
|---|---|---|
| EP | 660823 | 7/1995 |
| WO | WO-94/06770 | 3/1994 |
| WO | WO-98/54141 | 12/1998 |
| WO | WO-98/54143 | 12/1998 |
| WO | WO-98/54144 | 12/1998 |
| WO | WO-98/54145 | 12/1998 |
| WO | WO-00/61559 | 10/2000 |
| WO | WO-00/61561 | 10/2000 |
| WO | WO-03/097602 | 11/2003 |

OTHER PUBLICATIONS

Schou, C. et al., Bioorganic and Medicinal Chemistry Letters 7(24): 3095-3100 (1997).
Hjarnaa et al., Cancer Res. 59: 5751-5757 (1999).
Hara et al., "Elevation of cellular NAD levels by nicotinic acid and involvement of nicotinic acid phosphoribosyltranferase in human cells," J. Biol. Chem., 282(34): 24574-24582 (2007).
Khan et al., Expert Opin. Ther. Targets 11(5): 695-705 (2007).
Mhaidat et al., "Temozolomide induces senescence but not apoptosis in human melanoma cells," Brit. J. Cancer 97: 1225-1233 (2007).
Szkudelski, "The Mechanism of Alloxan and Streptozotocin Action in B Cells of the Rat Pancreas," Physiol. Res. 50: 536, 538-546 (2001).
Olesen et al., "Anticancer agent CHS-828 inhibits cellular synthesis of NAD," Biochemical and Biophysical Research Communication, vol. 367, pp. 799-804 (2008).

*Primary Examiner* — Raymond Henley, III
(74) *Attorney, Agent, or Firm* — Wilmer Cutler Pickering Hale and Dorr LLP

(57) ABSTRACT

The present invention relates to methods for decreasing cellular DNA repair in a patient diagnosed with or suspected to have chronic lymphocytic leukemia (CLL); decreasing cellular NAD+ biosynthesis in a patient diagnosed with or suspected to have CLL; or sensitizing a patient diagnosed with or suspected to have CLL to a DNA damaging therapy. The invention relates to methods for treating a patient diagnosed with or suspected to have CLL.

12 Claims, 15 Drawing Sheets

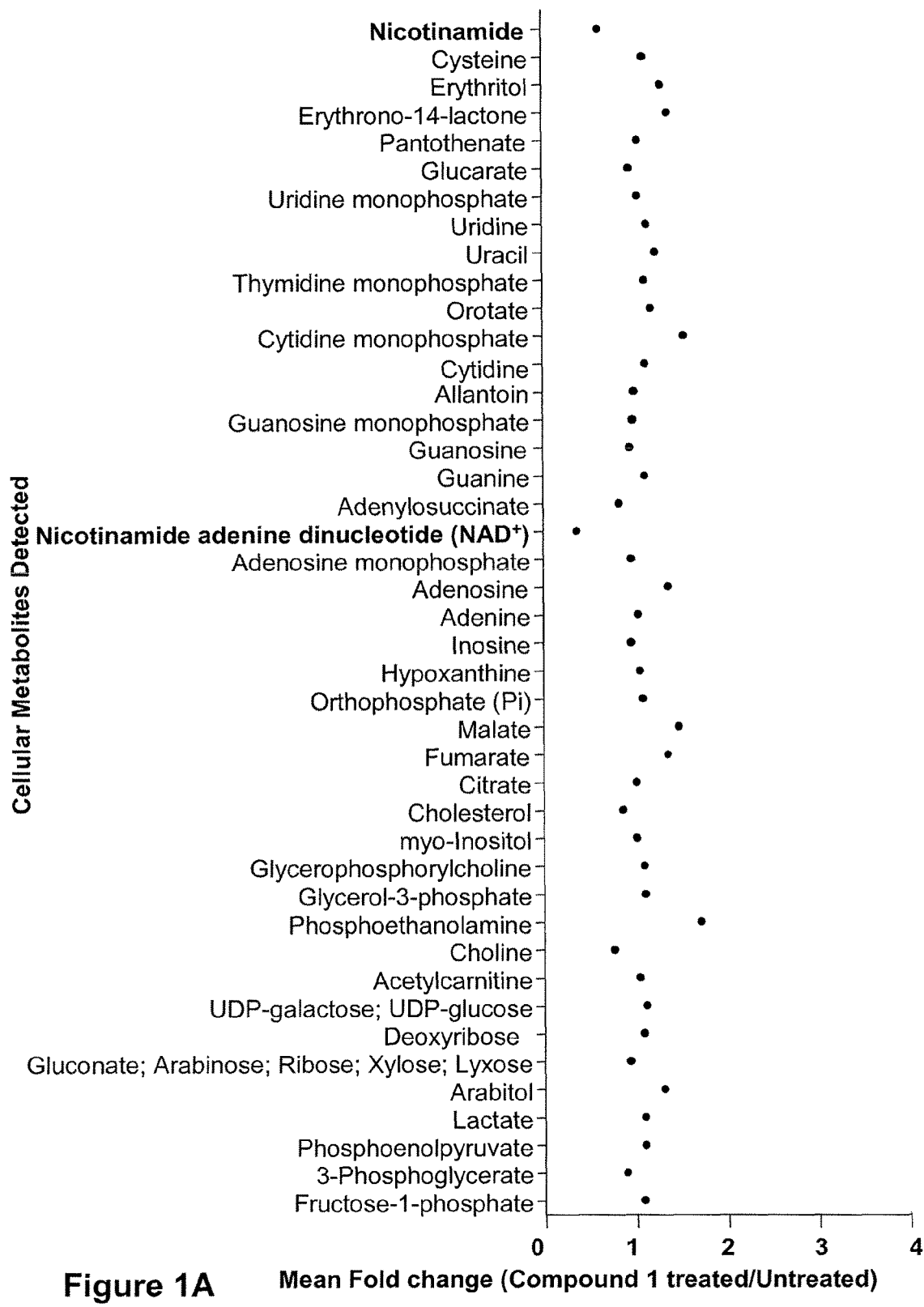
Figure 1A Mean Fold change (Compound 1 treated/Untreated)

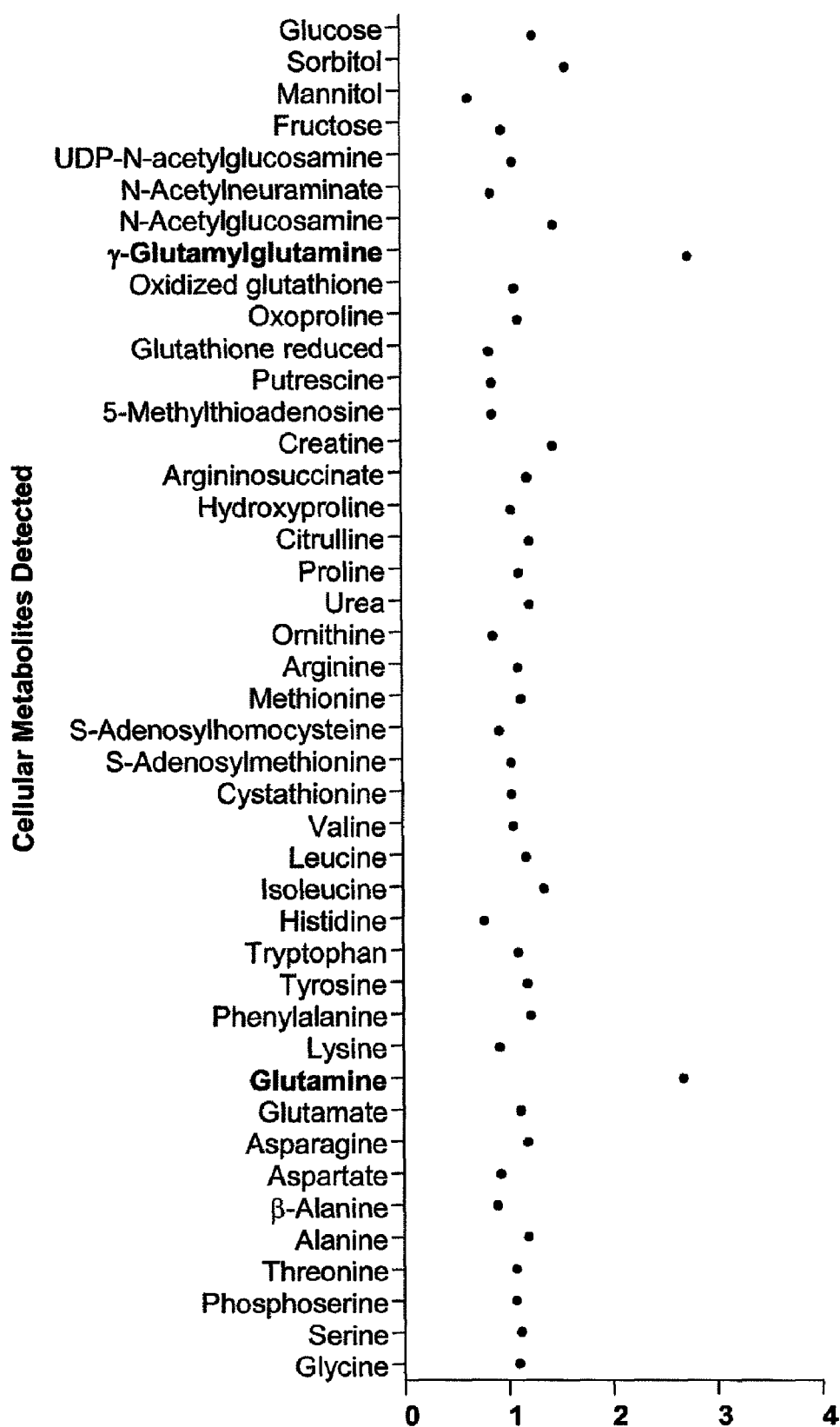
Figure 1B  Mean Fold change (Compound 1 treated/Untreated)

COMPOSITIONS AND METHODS FOR EFFECTING NAD+ LEVELS USING A NICOTINAMIDE PHOSPHORIBOSYL TRANSFERASE INHIBITOR

1. REFERENCE TO RELATED APPLICATIONS

This application is a continuation-in-part of U.S. application Ser. No. 12/237,755 filed on Sep. 25, 2008, which claims the benefit of U.S. Provisional Application No. 60/975,488, filed Sep. 26, 2007 and the benefit of U.S. Provisional Application No. 61/020,290, filed Jan. 10, 2008, the disclosures of which are incorporated by reference herein in their entirety.

2. FIELD OF THE INVENTION

The present invention relates to methods useful for effecting NAD$^+$ levels in a patient or a cell, and to methods useful in treating chronic lymphocytic leukemia ("CLL").

3. BACKGROUND OF THE INVENTION

Cancer is second only to cardiovascular disease as the leading cause of death in the United States. The American Cancer Society estimated that 1.4 million new cancer cases would be diagnosed and 565,000 people would die of cancer in 2006 (American Cancer Society, *Cancer Facts and Figures 2006*, Atlanta, Ga.). The National Cancer Institute estimated that in January 2002, approximately 10.1 million living Americans had a history of cancer. The National Institutes of Health estimate direct medical costs of cancer as over $100 billion per year with an additional $100 billion in indirect costs due to lost productivity—the largest such costs of any major disease.

Cancer is a process by which the controlling mechanisms that regulate cell growth and differentiation are impaired, resulting in a failure to control cell turnover and growth. This lack of control can cause a tumor to grow progressively, enlarging and occupying space in vital areas of the body. If the tumor invades surrounding tissue and is transported to distant sites, death of the individual can result.

Different classes of pyridyl cyanoguanidines with antiproliferative activity are disclosed in, for instance, EP 660 823, WO 98/54141, WO 98/54143, WO 98/54144, WO 98/54145, WO 00/61559 and WO 00/61561. The structure-activity relationships (SAR) of such compounds are discussed in C. Schou et al., *Bioorganic and Medicinal Chemistry Letters* 7(24), 1997, pp. 3095-3100, in which the antiproliferative effect of a number of pyridyl cyanoguanidines was tested in vitro on different human lung and breast cancer cell lines as well as on normal human fibroblasts. The compounds were also tested in vivo in nude mice carrying a human lung cancer tumor xenograft. Based on the SAR analysis, a specific compound (N-(6-(4-chlorophenoxy)hexyl)-N'-cyano-N"-(4-pyridyl)guanidine) was selected for its high antiproliferative activity in vitro and potent antitumor activity in the nude mouse model.

Hjarnaa et al., *Cancer Res.* 59, 1999, pp. 5751-5757, describe the results of further testing of the compound N-(6-(4-chlorophenoxy)hexyl)-N'-cyano-N"-(4-pyridyl)guanidine in in vitro and in vivo tests. The compound exhibited a potency in vitro which was comparable to that of the reference cytostatic agents daunorubicin and paclitaxel, while showing considerably less antiproliferative activity on normal human endothelial cells. In in vivo tests using nude mice transplanted with human tumor cells, the compound showed substantial antitumor activity, also against tumor cells that were resistant to conventional anticancer drugs such as paclitaxel.

NAD$^+$ can be synthesized through a de novo pathway from tryptophan or through a salvage pathway from two precursors, nicotinamide (the process which is herein referred to as the "nicotinamide salvage pathway") and nicotinic acid (the process which is herein referred to as the "nicotinic acid salvage pathway" or simply as "nicotinic acid pathway"). In the nicotinamide salvage pathway, nicotinamide is converted to NAD$^+$ by two enzymes, nicotinamide phosphoribosyl transferase (NMPRT) and nicotinamide mononucleotide adenyltransferase, which convert nicotinamide to nicotinamide mononucleotide and nicotinamide mononucleotide to NAD$^+$, respectively. In the nicotinic acid salvage pathway, nicotinic acid is converted to NAD$^+$ by three enzymes: nicotinic acid phosphoribosyl transferase (NAPRT), nicotinic acid mononucleotide adenyltransferase, and NAD$^+$ synthetase, which convert nicotinic acid to nicotinic acid mononucleotide, nicotinic acid mononucleotide to nicotinic acid adenine dinucleotide, and nicotinic acid adenine dinucleotide to NAD$^+$, respectively (see Hara et al. (2007), "Elevation of cellular NAD levels by nicotinic acid and involvement of nicotinic acid phosphoribosyltransferase in human cells", *Journal of Biological Chemistry*, 282 (34): 24574-24582).

Tumor cells have a high rate of NAD$^+$ turnover due to elevated ADP-ribosylation activity, predominantly mediated by the poly(ADP-ribose) polymerases (PARPs). Poly ADP-ribosylation of specific target proteins is crucial for genome stability, DNA repair, telomere maintenance, cell death and other biological functions. Proteins that bind mono and poly (ADP-ribose) have been identified, suggesting that these molecules may have important cellular functions themselves. DNA damage can stimulate NAD$^+$ biosynthesis. Expression levels of NMPRT, which is the rate-limiting enzyme in the salvage pathway from the breakdown product nicotinamide, are upregulated in colorectal cancers, suggesting that NMPRT may be crucial for maintaining cellular NAD$^+$ levels in tumors. NMPRT-deficient mice die during early embryogenesis. (E)-N-[4-(1-benzoylpiperidin-4-yl) butyl]-3-(pyridin-3-yl)acrylamide, also known as FK866, is a potent small-molecule inhibitor of human NMPRT, and the consequent reduction in NAD$^+$ levels can cause apoptosis of tumor cells while having little (toxic) effects on normal cells. This validates NMPRT as a target for the development of novel therapeutic agents (see Khan et al., *Expert Opin. Ther. Targets* (2007), 11(5):695-705).

Despite the significant research efforts and resources that have been directed towards the development of anti-cancer drugs and improved methods for treating cancer, there remains a need in the art for novel compounds, compositions, or methods that are useful for modulating NMPRT activity, decreasing cellular DNA repair, decreasing NAD$^+$ biosynthesis, sensitizing a patient to DNA damaging therapy, or increasing efficacy of radiation therapy. In addition, there remains a need for novel compounds, compositions and methods that are useful for treating a cancer deficient in nicotinic acid pathway.

Citation of any reference in Section 3 of this application is not an admission that the reference is prior art.

4. SUMMARY OF THE INVENTION

The invention is based, in part, upon the discovery that a Pyridyl Cyanoguanidine or a Prodrug Thereof inhibits nicotinamide phosphoribosyl transferase (NMPRT), an enzyme involved in NAD$^+$ biosynthesis; and, in part, on the discovery that a cancer deficient in nicotinic acid pathway, such as chronic lymphocytic leukemia (CLL), can be advantageously treated with a NMPRT inhibitor and nicotinic acid.

In one aspect, the invention relates to the use of the compounds having the formula Ia

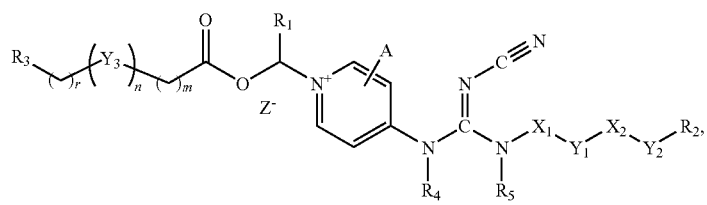

the formula Ib

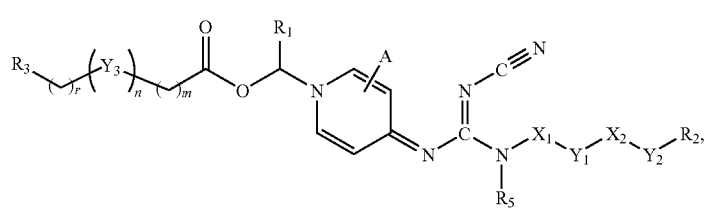

the formula II

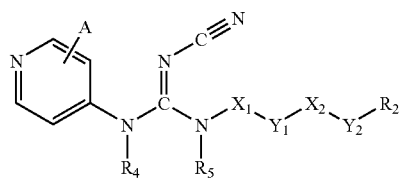

or a pharmaceutically acceptable salt thereof, wherein $X_1$ and $X_2$ are independently a bond, a straight, branched and/or cyclic hydrocarbon diradical which is unsubstituted or substituted with one or more hydroxy, halogen, nitro, amino, cyano, aminosulfonyl, alkylsulfonylamino, alkylcarbonyl, formyl, aminocarbonyl or alkylcarbonylamino; a heteroarylene or non-aromatic heterocyclic hydrocarbon diradical, each of which is unsubstituted or substituted with one or more straight, branched and/or cyclic non-aromatic hydrocarbon radical, hydroxyl, halogen, amino, nitro, cyano, aminosulfonyl, alkylsulfonylamino, alkylcarbonyl, formyl, aminocarbonyl or alkylcarbonylamino;

each $Y_1$ and $Y_2$ is independently a bond, an ether diradical (R'—O—R"), an amine diradical (R'—N—R"), O, S, S(O), S(O)$_2$, C(O), NH—CO, CO—NH, SO$_2$—N(R'), methylene or N(R')—SO$_2$ wherein R' and R" are independently a straight or branched hydrocarbon diradical containing 1-4 carbon atoms;

$Y_3$ is O, O—C(O), C(O)—O, or N(R$_8$); R$_8$ is hydrogen or C$_{1-4}$ alkyl;

$R_1$ is hydrogen or straight, branched and/or cyclic alkyl, all of which other than hydrogen are unsubstituted or substituted with phenyl; aryl; aralkyl or an aromatic hydrocarbon radical;

$R_2$ is aryl, heteroaryl or a non-aromatic heterocyclic hydrocarbon radical, tetrahydropyranyloxy, di-(C$_{1-4}$ alkoxy) phosphinoyloxy and C$_{1-4}$ alkoxycarbonylamino, all of which can be unsubstituted or substituted with one or more of halogen, trifluoromethyl, hydroxy, C$_{1-4}$ alkoxy, C$_{1-4}$ alkoxycarbonyl, nitro, cyano, amino, aminocarbonyl, sulfamoyl, C$_{1-4}$ alkyl or C$_{1-4}$ hydroxyalkyl, wherein the C$_{1-4}$ alkyl and C$_{1-4}$ hydroxyalkyl are unsubstituted or substituted with one or more of halogen, hydroxyl, cyano or nitro;

$R_3$ is hydrogen, a straight, branched and/or cyclic hydrocarbon radical, all of which other than hydrogen can be substituted with one or more amino, hydroxy, carboxy, halogen, nitro, cyano, alkoxy, aminocarbonyl, C$_{1-4}$ alkoxycarbonyl, C$_{1-4}$ alkoxycarbonylamino, sulfo, hydroxysulfonyloxy, dihydroxyphosphinoyloxy, phosphono, sulfamino, aminosulfonyl, aminoacylamino or dialkoxyphosphinoyl; heteroaryl or a non-aromatic heterocyclic hydrocarbon radical, all of which can be substituted with one or more straight, branched and/or cyclic hydrocarbon radical, amino, hydroxy, carboxy, halogen, nitro, cyano, alkoxy, aminocarbonyl, C$_{1-4}$ alkoxycarbonyl, C$_{1-4}$ alkoxycarbonylamino, sulfo, hydroxysulfonyloxy, dihydroxyphosphinoyloxy, phosphono, sulfamino, aminosulfonyl, aminoacylamino or dialkoxyphosphinoyl;

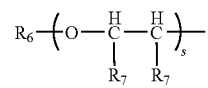

wherein s is an integer from 1 to 200; $R_6$ is hydrogen or a substituted or unsubstituted non-aromatic hydrocarbon radical; each $R_7$ is independently hydrogen or methyl;

each $R_4$ and $R_5$ is independently represent hydrogen; a straight, branched and/or cyclic hydrocarbon radical, all of which other than hydrogen can be substituted with one or more of halogen, hydroxyl, halogen, amino, nitro or cyano;

A represents hydrogen, an substituted or unsubstituted straight, branched and/or cyclic hydrocarbon radical, hydroxy, halogen, nitro, cyano, heteroaryl, heteroaralkyl or thiol;

Z⁻ is a pharmaceutically acceptable anion;
each m and r is independently an integer from 0 to 4; and n is 0 or 1.

A compound of the formula Ia, Ib, II, or a pharmaceutically acceptable salt thereof (a "Pyridyl Cyanoguanidine or a Prodrug Thereof") is useful for treating chronic lymphocytic leukemia (CLL).

In one aspect, the invention provides a method for treating a patient diagnosed with or suspected to have chronic lymphocytic leukemia (CLL) comprising administering to the patient: (a) an effective amount of a nicotinamide phosphoribosyl transferase inhibitor of the formula Ia

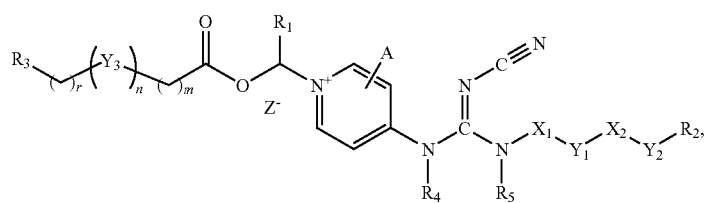

[Ia]

the formula Ib

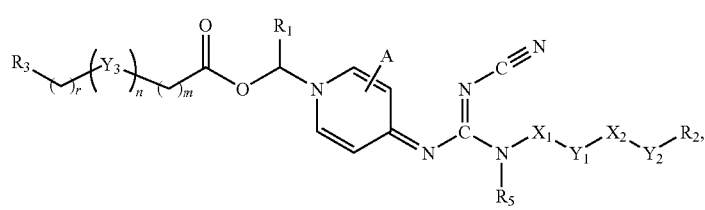

[Ib]

the formula II

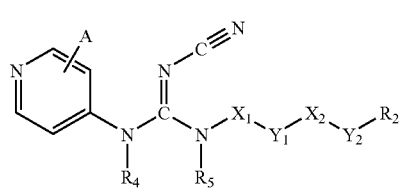

[II]

or a pharmaceutically acceptable salt thereof,
wherein $X_1$ and $X_2$ are independently a bond, a straight, branched and/or cyclic hydrocarbon diradical which is unsubstituted or substituted with one or more hydroxy, halogen, nitro, amino, cyano, aminosulfonyl, alkylsulfonylamino, alkylcarbonyl, formyl, aminocarbonyl or alkylcarbonylamino; a heteroarylene or non-aromatic heterocyclic hydrocarbon diradical, each of which is unsubstituted or substituted with one or more straight, branched and/or cyclic non-aromatic hydrocarbon radical, hydroxyl, halogen, amino, nitro, cyano, aminosulfonyl, alkylsulfonylamino, alkylcarbonyl, formyl, aminocarbonyl or alkylcarbonylamino;
each $Y_1$ and $Y_2$ is independently a bond, an ether diradical (R'—O—R"), an amine diradical (R'—N—R"), O, S, S(O), S(O)₂, C(O), NH—CO, CO—NH, SO₂—N(R'), methylene or N(R')—SO₂ wherein R' and R" are independently a straight or branched hydrocarbon diradical containing 1-4 carbon atoms;
$Y_3$ is O, O—C(O), C(O)—O, or N(R₈); R₈ is hydrogen or $C_{1-4}$ alkyl;
$R_1$ is hydrogen or straight, branched and/or cyclic alkyl, all of which other than hydrogen are unsubstituted or substituted with phenyl; aryl; aralkyl; or an aromatic hydrocarbon radical;
$R_2$ is aryl, heteroaryl or a non-aromatic heterocyclic hydrocarbon radical, tetrahydropyranyloxy, di-($C_{1-4}$ alkoxy) phosphinoyloxy and $C_{1-4}$ alkoxycarbonylamino, all of which can be unsubstituted or substituted with one or more of halogen, trifluoromethyl, hydroxy, $C_{1-4}$ alkoxy, $C_{1-4}$ alkoxycarbonyl, nitro, cyano, amino, aminocarbonyl, sulfamoyl, $C_{1-4}$ alkyl or $C_{1-4}$ hydroxyalkyl, wherein the $C_{1-4}$ alkyl and $C_{1-4}$ hydroxyalkyl are unsubstituted or substituted with one or more of halogen, hydroxyl, cyano or nitro;
$R_3$ is hydrogen, a straight, branched and/or cyclic hydrocarbon radical, all of which other than hydrogen can be substituted with one or more amino, hydroxy, carboxy, halogen, nitro, cyano, alkoxy, aminocarbonyl, $C_{1-4}$ alkoxycarbonyl, $C_{1-4}$ alkoxycarbonylamino, sulfo, hydroxysulfonyloxy, dihydroxyphosphinoyloxy, phosphono, sulfamino, aminosulfonyl, aminoacylamino or dialkoxyphosphinoyl; heteroaryl or a non-aromatic heterocyclic hydrocarbon radical, all of which can be substituted with one or more straight, branched and/or cyclic hydrocarbon radical, amino, hydroxy, carboxy, halogen, nitro, cyano, alkoxy, aminocarbonyl, $C_{1-4}$ alkoxycarbonyl, $C_{1-4}$ alkoxycarbonylamino, sulfo, hydroxysulfonyloxy, dihydroxyphosphinoyloxy, phosphono, sulfamino, aminosulfonyl, aminoacylamino or dialkoxyphosphinoyl;

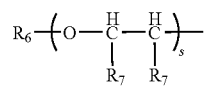

wherein s is an integer from 1 to 200; $R_6$ is hydrogen or a non-aromatic hydrocarbon radical which is unsubstituted or substituted with hydroxyl, halogen, amino, nitro, cyano, aminosulfonl, alkylsulfonylamino, alkylcarbonyl, formyl, aminocarbonyl or alkylcarbonylamino; each $R_7$ is independently hydrogen or methyl;

each $R_4$ and $R_5$ is independently represent hydrogen; a straight, branched and/or cyclic hydrocarbon radical, all of which other than hydrogen can be substituted with one or more of halogen, hydroxyl, halogen, amino, nitro or cyano;

A represents hydrogen, an substituted or unsubstituted straight, branched and/or cyclic hydrocarbon radical, hydroxy, halogen, nitro, cyano, heteroaryl, heteroaralkyl or thiol;

$Z^-$ is a pharmaceutically acceptable anion;

each m and r is independently an integer from 0 to 4; and n is 0 or 1; and (b) an effective amount of nicotinic acid.

In another aspect, the invention provides a method for treating a patient diagnosed with or suspected to have chronic lymphocytic leukemia (CLL) comprising administering to the patient: (a) an effective amount of (E)-N-[4-(1-benzoylpiperidin-4-yl)butyl]-3-(pyridin-3-yl)acrylamide; and (b) an effective amount of nicotinic acid.

In some embodiments, the effective amount of nicotinic acid is administered intravenously or orally.

In still another aspect, the invention provides a method for treating a patient diagnosed with or suspected to have chronic lymphocytic leukemia (CLL) comprising administering to the patient: (a) an effective amount of a nicotinamide phosphoribosyl transferase inhibitor of the formula Ia

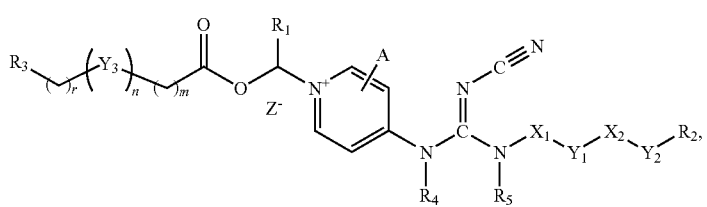

[Ia]

the formula Ib

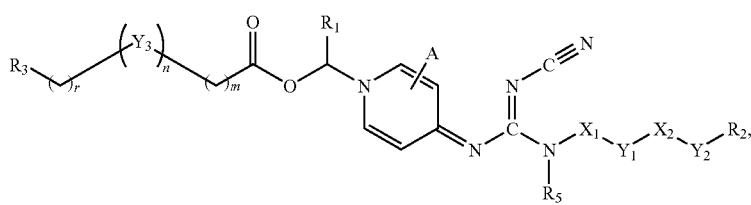

[Ib]

formula II

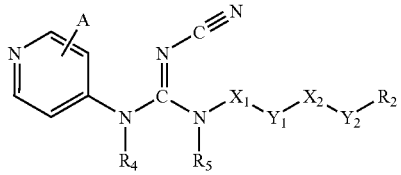

[II]

or a pharmaceutically acceptable salt thereof, wherein $X_1$ and $X_2$ are independently a bond, a straight, branched and/or cyclic hydrocarbon diradical which is unsubstituted or substituted with one or more hydroxy, halogen, nitro, amino, cyano, aminosulfonyl, alkylsulfo-nylamino, alkylcarbonyl, formyl, aminocarbonyl or alkylcarbonylamino; a heteroarylene or non-aromatic heterocyclic hydrocarbon diradical, each of which is unsubstituted or substituted with one or more straight, branched and/or cyclic non-aromatic hydrocarbon radical, hydroxyl, halogen, amino, nitro, cyano, aminosulfonyl, alkylsulfonylamino, alkylcarbonyl, formyl, aminocarbonyl or alkylcarbonylamino;

each $Y_1$ and $Y_2$ is independently a bond, an ether diradical (R'—O—R"), an amine diradical (R'—N—R"), O, S, S(O), S(O)$_2$, C(O), NH—CO, CO—NH, SO$_2$—N(R'), methylene or N(R')—SO$_2$ wherein R' and R" are independently a straight or branched hydrocarbon diradical containing 1-4 carbon atoms;

$Y_3$ is O, O—C(O), C(O)—O, or N($R_8$); $R_8$ is hydrogen or $C_{1-4}$ alkyl;

$R_1$ is hydrogen or straight, branched and/or cyclic alkyl, all of which other than hydrogen are unsubstituted or substituted with phenyl; aryl; aralkyl; or an aromatic hydrocarbon radical;

$R_2$ is aryl, heteroaryl or a non-aromatic heterocyclic hydrocarbon radical, tetrahydropyranyloxy, di-($C_{1-4}$ alkoxy) phosphinoyloxy and $C_{1-4}$ alkoxycarbonylamino, all of which can be unsubstituted or substituted with one or more of halogen, trifluoromethyl, hydroxy, $C_{1-4}$ alkoxy, $C_{1-4}$ alkoxycarbonyl, nitro, cyano, amino, aminocarbonyl, sulfamoyl, $C_{1-4}$ alkyl or $C_{1-4}$ hydroxyalkyl, wherein the $C_{1-4}$ alkyl and $C_{1-4}$ hydroxyalkyl are unsubstituted or substituted with one or more of halogen, hydroxyl, cyano or nitro;

$R_3$ is hydrogen, a straight, branched and/or cyclic hydrocarbon radical, all of which other than hydrogen can be substituted with one or more amino, hydroxy, carboxy, halogen, nitro, cyano, alkoxy, aminocarbonyl, $C_{1-4}$ alkoxycarbonyl, $C_{1-4}$ alkoxycarbonylamino, sulfo, hydroxysulfonyloxy, dihydroxyphosphinoyloxy, phosphono, sulfamino, aminosulfonyl, aminoacylamino or dialkoxyphosphinoyl; heteroaryl or a non-aromatic heterocyclic hydrocarbon radical, all of which can be substituted with one or more straight, branched and/or cyclic hydrocarbon radical, amino, hydroxy, carboxy, halogen, nitro, cyano, alkoxy, aminocarbonyl, $C_{1-4}$ alkoxycarbonyl, $C_{1-4}$ alkoxycarbonylamino, sulfo, hydroxysulfonyloxy, dihydroxyphosphinoyloxy, phosphono, sulfamino, aminosulfonyl, aminoacylamino or dialkoxyphosphinoyl;

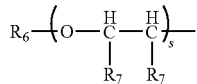

wherein s is an integer from 1 to 200; $R_6$ is hydrogen or a non-aromatic hydrocarbon radical optionally substituted with hydroxyl, halogen, amino, nitro, cyano, aminosulfonl, alkylsulfonylamino, alkylcarbonyl, formyl, aminocarbonyl or alkylcarbonylamino; each $R_7$ is independently hydrogen or methyl;

each $R_4$ and $R_5$ is independently represent hydrogen; a straight, branched and/or cyclic hydrocarbon radical, all of which other than hydrogen can be substituted with one or more of halogen, hydroxyl, halogen, amino, nitro or cyano;

A represents hydrogen, an substituted or unsubstituted straight, branched and/or cyclic hydrocarbon radical, hydroxy, halogen, nitro, cyano, heteroaryl, heteroaralkyl or thiol;

$Z^-$ is a pharmaceutically acceptable anion;

each m and r is independently an integer from 0 to 4; and n is 0 or 1;

(b) an effective amount of nicotinic acid; and
(c) DNA damaging therapy.

In one aspect, the invention provides a method for treating a patient diagnosed with or suspected to have chronic lymphocytic leukemia (CLL) comprising administering to the patient: (a) an effective amount of (E)-N-[4-(1-benzoylpiperidin-4-yl)butyl]-3-(pyridin-3-yl)acrylamide; (b) an effective amount of nicotinic acid; and (c) DNA damaging therapy.

In some embodiments, the effective amount of nicotinic acid is administered intravenously or orally.

In some embodiments, the DNA damaging therapy comprises administering the patient an effective amount of a DNA damaging chemotherapeutic agent.

In some embodiments, the DNA damaging chemotherapeutic agent is Cladribine, Pentostatin, Methotrexate, Trimetrexate glucuronate, Pemetrexed, Treosulfan, Busulfan, Dacarbazine, Temozolomide, Mitomycin C, Chlorambucil, Ifosfamide, Melphalan, Thiotepa, Mechlorethamine, Carmustine, Bendamustin, Fotemustine, Lomustine, Streptozocin, Carboplatin, Cisplatin, Lobaplatin, Oxaliplatin Bleomycin, Hydroxyurea, Actinomycin D, Azacitidine, Decitabine, Nelarabine, Cytarabine, Fludarabine, Clofarabine, Vorinostat, Gemcitabine, 5-Fluorouracil, Capecitabine, Floxuridine, Raltitrexed, Pemetrexed, Irinotecan, Topotecan, Amrubicin, Daunorubicin, Doxorubicin, Epirubicin, Etoposide, Idarubicin, Mitoxantrone, Teniposide, Valrubicin, Allopurinol, or a pharmaceutically acceptable salt thereof.

In some embodiments, the compound of formula Ia, Ib, or II is

1-[2-(2-(2-Methoxyethoxy)-ethoxy)-ethoxy-carbonyloxymethyl]-4-[N'-cyano-N''-(6-(4-chlorophenoxy)-hexyl)-N-guanidino]-pyridinium chloride;

1-[2-(2-Methoxyethoxy)-ethoxy-carbonyloxymethyl]-4-[N'-cyano-N''-(6-(4-chlorophenoxy)-hexyl)-N-guanidino]-pyridinium chloride;

1-[2-Methoxyethoxy)-carbonyloxymethyl]-4-[N'-cyano-N''-(6-(4-chlorophenoxy)-hexyl)-N-guanidino]-pyridinium chloride;

1-[2-(2-(2-Methoxyethoxy)-ethoxy)-ethoxy-carbonyloxymethyl]-4-[N'-cyano-N''-(6-(4-chlorophenoxy)-hexyl)-N-guanidino]-pyridinium iodide;

N-[1-(2-(2-(2-Methoxyethoxy)-ethoxy)-ethoxycarbonyloxymethyl)-1,4-dihydropyridin-4-ylidene]-N'-cyano-N''-(6-(4-chlorophenoxy)-hexyl)-guanidine;

1-[2-(2-(2-Methoxyethoxy)-ethoxy)-ethoxy-carbonyloxymethyl]-4-[N'-cyano-N''-(6-(4-chlorophenoxy)-hexyl)-N-guanidino]-pyridinium chloride;

1-[1-(2-(2-Methoxyethoxy)-ethoxy-carbonyloxy)-ethyl]-4-[N'-cyano-N''-(6-(4-chlorophenoxy)-hexyl)-N-guanidino]-pyridinium chloride;

1-[2-(2-(2-Methoxyethoxy)-ethoxy)-ethoxy-acetoxymethyl]-4-[N'-cyano-N''-(6-(4-chlorophenoxy)-hexyl)-N-guanidino]-pyridinium chloride;

1-[2-(2-(2-(2-Methoxyethoxy)-ethoxy)-ethoxy)-ethoxy-carbonyloxymethyl]-4-[N'-cyano-N''-(6-(4-chlorophenoxy)-hexyl)-N-guanidino]-pyridinium chloride;

1-Pivaloyloxymethyl-4-[N'-cyano-N''-(6-(4-chlorophenoxy)-hexyl)-N-guanidino]-pyridinium chloride;

1-Acetoxymethyl-4-[N'-cyano-N''-(6-(4-chlorophenoxy)-hexyl)-N-guanidino]-pyridinium chloride;

1-(L)-Valyloxymethyl-4-[N'-cyano-N''-(6-(4-chlorophenoxy)-hexyl)-N-guanidino]-pyridinium chloride;

1-Glycyloxymethyl-4-[N'-cyano-N''-(6-(4-chlorophenoxy)-hexyl)-N-guanidino]-pyridinium chloride;

1-[Monobenzyl succinyloxymethyl]-4-[N'-cyano-N''-(6-(4-chlorophenoxy)-hexyl)-N-guanidino]-pyridinium chloride;

1-[2-(2-(2-(2-(2-Methoxyethoxy)-ethoxy)-ethoxy)-ethoxy)-ethoxy carbonyloxymethyl]-4-[N'-cyano-N''-(6-(4-chlorophenoxy)-hexyl)-N-guanidino]-pyridinium chloride;

1-[2-(2-(2-(2-(2-Methoxyethoxy)-ethoxy)-ethoxy)-ethoxy-ethoxy-ethoxy-carbonyloxymethyl]-4-[N'-cyano-N''-(6-(4-chlorophenoxy)-hexyl)-N-guanidino]-pyridinium chloride;

1-[2-(2-(2-Methoxyethoxy)-ethoxy)-ethoxy-carbonyloxymethyl]-4-[N'-cyano-N''-(9-(diethoxyphosphinoyloxy)-nonyl)-N-guanidino]-pyridinium chloride;

1-[2-(2-(2-Methoxyethoxy)-ethoxy)-ethoxy)-carbonyloxymethyl]-4-[N'-cyano-N''-(12-(tert-butyloxycarbonylamino)-dodecyl)-N-guanidino]-pyridinium iodide;

1-[2-(2-(2-Methoxyethoxy)-ethoxy)-ethoxy)-carbonyloxymethyl]-4-[N'-cyano-N''-(12-(tert-butyloxycarbonylamino)-dodecyl)-N-guanidino]-pyridinium chloride;

1-[2-(2-(2-Methoxyethoxy)-ethoxy)-ethoxy)-ethoxy-carbonyloxymethyl]-4-[N'-cyano-N''-(12-(tert-butyloxycarbonylamino)-dodecyl)-N-guanidino]-pyridinium chloride;

1-[3-(N-tert-butoxycarbonylamino)-propyloxy-carbonyloxymethyl]-4-[N'-cyano-N''-(6-(4-chlorophenoxy)-hexyl)-N-guanidino]-pyridinium iodide;

1-[3-Amino-propyloxy-carbonyloxymethyl]-4-[N'-cyano-N''-(6-(4-chlorophenoxy)-hexyl)-N-guanidino]-pyridinium chloride;

1-[3-(N-tert-butoxycarbonylamino)-propyl-carbamoyloxymethyl]-4-[N'-cyano-N''-(6-(4-chlorophenoxy)-hexyl)-N-guanidino]-pyridinium iodide;

1-[3-Aminopropyl-carbamoyloxymethyl]-4-[N'-cyano-N''-(6-(4-chlorophenoxy)-hexyl)-N-guanidino]-pyridinium chloride;

1-[5-(N-tert-butoxycarbonylamino)-pentanoyloxymethyl]-4-[N'-cyano-N''-(6-(4-chlorophenoxy)-hexyl)-N-guanidino]-pyridinium iodide;

1-[5-Amino-pentanoyloxymethyl]-4-[N'-cyano-N''-(6-(4-chlorophenoxy)-hexyl)-N-guanidino]-pyridinium chloride;

1-[3-(tert-butoxycarbonyl)-propionyloxymethyl]-4-[N'-cyano-N''-(6-(4-chlorophenoxy)-hexyl)-N-guanidino]-pyridinium chloride;

1-[3-carboxy-propionyloxymethyl]-4-[N'-cyano-N''-(6-(4-chlorophenoxy)-hexyl)-N-guanidino]-pyridinium chloride;

1-[N-(tert-butoxycarbonylmethyl)-carbamoyloxymethyl]-4-[N'-cyano-N''-(6-(4-chlorophenoxy)-hexyl)-N-guanidino]-pyridinium iodide;

1-[N-(carboxymethyl)-carbamoyloxymethyl]-4-[N'-cyano-N''-(6-(4-chlorophenoxy)-hexyl)-N-guanidino]-pyridinium chloride;

1-[1-(tert-butoxycarbonyl)-4-piperidyloxy-carbonyloxymethyl]-4-[N'-cyano-N''-(6-(4-chlorophenoxy)-hexyl)-N-guanidino]-pyridinium iodide;

1-[4-Piperidyloxy-carbonyloxymethyl]-4-[N'-cyano-N''-(6-(4-chloro-phenoxy)-hexyl)-N-guanidino]-pyridinium chloride;

1-[tert-butoxycarbonylmethoxy-carbonyloxymethyl]-4-[N'-cyano-N''-(6-(4-chlorophenoxy)-hexyl)-N-guanidino]-pyridinium iodide;

1-[Carboxymethoxy-carbonyloxymethyl]-4-[N'-cyano-N''-(6-(4-chlorophenoxy)-hexyl)-N-guanidino]-pyridinium chloride;

N-[1-(α-(2-(2-(2-Methoxyethoxy)-ethoxy)-ethoxycarbonyloxy)benzyl)-1,4-dihydropyridin-4-ylidene]-N'-cyano-N''-(6-(4-chlorophenoxy)-hexyl)-guanidine;

4-[N'-cyano-N''-(6-(4-chlorophenoxy)-hexyl)-N-guanidino]-pyridine;

4-[N'-cyano-N''-(9-(diethoxyphosphinoyloxy)-nonyl)-N-guanidino]-pyridine;

4-[N'-cyano-N''-(12-(tert-butyloxycarbonylamino)-dodecyl)-N-guanidino]-pyridine;

or a pharmaceutically acceptable salt thereof.

In a particular embodiment, the compound of formula Ia is 1-[2-(2-(2-(2-Methoxyethoxy)-ethoxy)-ethoxy)-ethoxy-carbonyloxymethyl]-4-[N'-cyano-N''-(6-(4-chlorophenoxy)-hexyl)-N-guanidino]-pyridinium chloride.

In a particular embodiment, the compound of formula II is 4-[N'-cyano-N''-(6-(4-chlorophenoxy)-hexyl)-N-guanidino]-pyridine.

In some embodiments, $Z^-$ is chloride, bromide, iodide, sulfate, methanesulfonate, p-toluenesulfonate, nitrate or phosphate.

5. BRIEF DESCRIPTION OF THE DRAWINGS

FIGS. 1A, 1B and 1C are graphic representations that show kinetic and biochemical pathway profiling studies of IM-9 cells treated with a NMPRT inhibitor (Compound 1);

Figure 10:
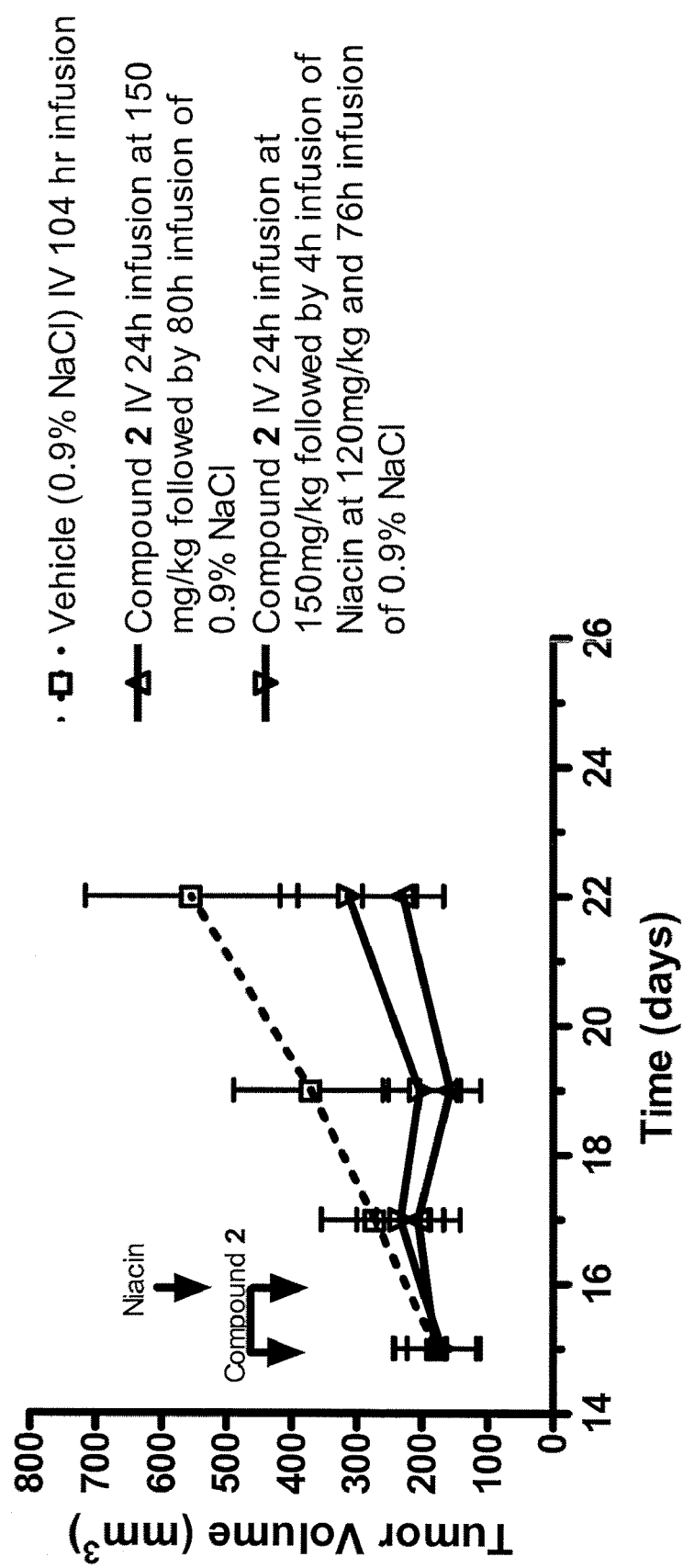
Figure 11:
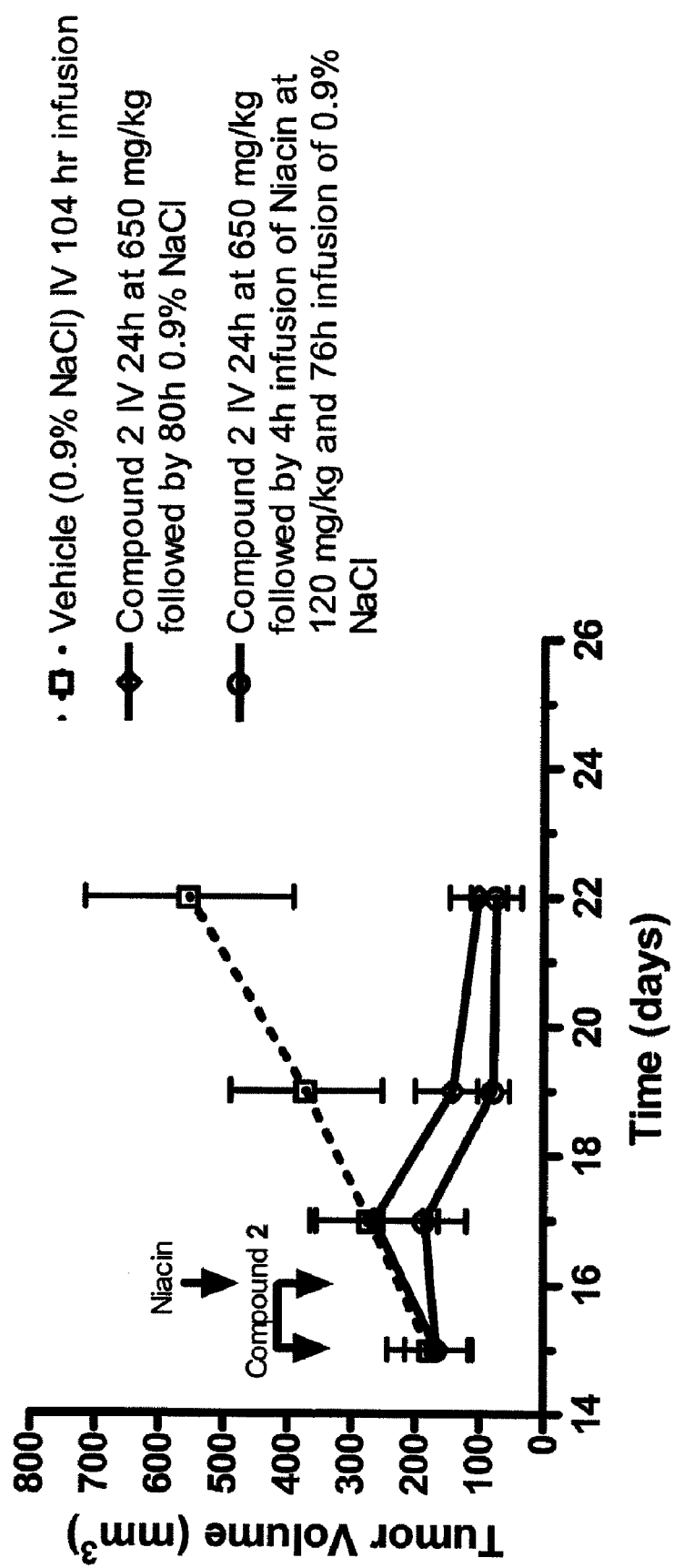

FIG. 10 is a graphic representation that shows the effects of administration of a NMPRT inhibitor (Compound 2) and nicotinic acid (niacin) on tumor size in mice injected with human fibrosarcoma HT1080 cells at the NMPRT inhibitor dosage of 150 mg/kg; and FIG. 11 is a graphic representation that shows the effects of administration of a NMPRT inhibitor (Compound 2) and nicotinic acid (niacin) on tumor size in mice injected with human fibrosarcoma HT1080 cells at the NMPRT inhibitor dosage of 650 mg/kg.

Figure 12:
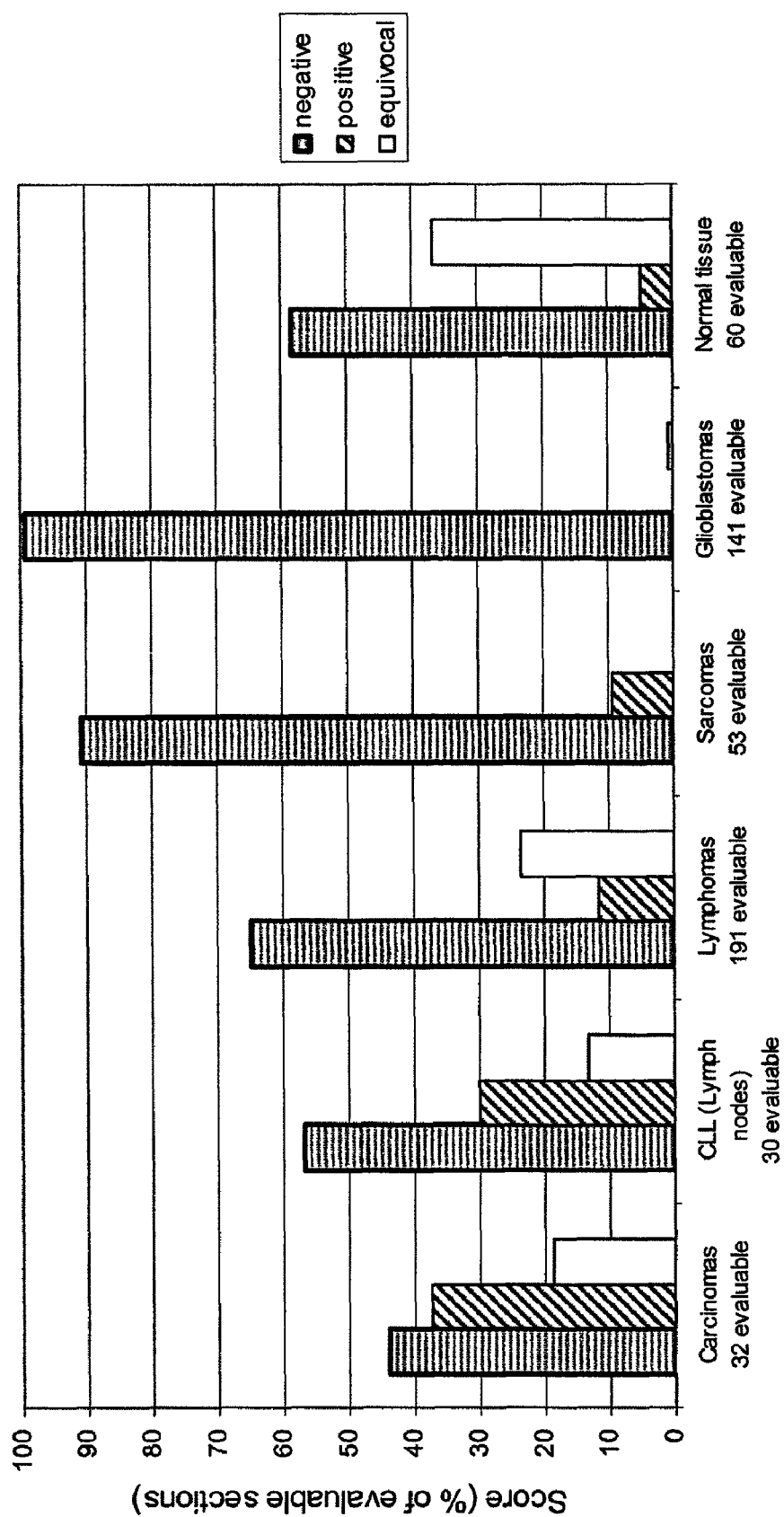

FIG. 12 is a graphic representation summarizing the results of the IHC analysis for NAPRT1 (NAPRT) in various cancer and normal tissue microarrays.

6. DETAILED DESCRIPTION OF THE INVENTION

6.1 Definitions and Abbreviations

The following definitions are used herein:

A "toxic dose" refers to a dose of a compound, for example an active pharmaceutical ingredient, which when administered to a patient causes undesirable and potentially health-threatening side effects in the patient. In one embodiment, a toxic dose is a lethal dose.

A "patient" is a mammal, e.g., a human, mouse, rat, guinea pig, dog, cat, horse, cow, pig, or non-human primate, such as a monkey, chimpanzee, baboon. In one embodiment, the monkey is a rhesus. In a specific embodiment, the patient is a human. A "subject" and a "patient" are meant to be synonyms.

A "target patient" is a patient that is being administered therapy.

A "target cell" is a cell that is being administered therapy. In one embodiment, the target cell is a cell in a tissue culture.

The phrase "pharmaceutically acceptable salt," as used herein, is a salt formed from an acid and a basic nitrogen group of a compound. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, besylate, mesylate, camphor sulfonate, and pamoate (i.e., 1,1'-methylene-bis-(2-OH-3-naphthoate)) salts. The term "pharmaceutically acceptable salt" also refers to a salt of a compound having an acidic functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, tris-(hydroxymethyl)methylamine, or 2-hydroxy-tert-butylamine, or N,N-di-lower alkyl-N-(hydroxy lower alkyl)-amines, such as N,N-dimethyl-N-(2-hydroxyethyl)amine or tri-(2-hydroxyethyl)amine; N-methyl-D-glucamine; and amino acids such as arginine, lysine, and the like.

An "effective amount" when used in connection with a Pyridyl Cyanoguanidine or a Prodrug Thereof is an amount of the Pyridyl Cyanoguanidine or a Prodrug Thereof, alone or in combination with one or more other active pharmaceutical ingredients, that is effective for achieving the desired effect (i.e., the desired therapeutic use). An "effective amount" when used in connection with nicotinic acid is an amount of nicotinic acid, alone or in combination with one or more other active pharmaceutical ingredients, that is effective for achieving the desired effect (i.e., the desired therapeutic use). An "effective amount" when used in connection with a NMPRT inhibitor is an amount of the NMPRT inhibitor, alone or in combination with one or more other active pharmaceutical ingredients, that is effective for achieving the desired effect (i.e., the desired therapeutic use).

"Sensitize," as used herein, means making more susceptible. For example, sensitizing a patient to a DNA damaging therapy means that the sensitized patient is more susceptible to the DNA damaging therapy than a patient that has not been sensitized, i.e., the DNA damaging therapy is more effective in a sensitized patient than in a non-sensitized patient.

"Modulating activity," as used herein, means increasing or decreasing activity compared to a reference activity. In one embodiment, modulating activity is inhibiting activity. Modulating activity of an enzyme means increasing or decreasing activity of the enzyme compared to a reference activity, including partially or totally inhibiting the enzyme.

"Manifestation of nicotinamide phosphoribosyl transferase activity," as used herein, means any quantity that is observable or measurable, and the value of which changes directly or indirectly as a result of a change in nicotinamide phosphoribosyl transferase activity. Such examples include levels of co-enzymes, proteins, mononucleotides, dinucleotides, nucleic acids, or other markers in the cell, tissue, or patient that was administered a NMPRT inhibitor. Further examples of manifestation of nicotinamide phosphoribosyl transferase activity include observed or measured changes in disease or condition of a cell, tissue, or a patient. In one embodiment, the disease or condition is cancer. In one embodiment, the cancer is deficient in nicotinic acid pathway. Change in activity of nicotinamide phosphoribosyl transferase can also be manifested by a change in magnitude or types of side effects associated with toxicity of a certain therapy or medication such as radiation therapy and anti-cancer medications.

An "NMPRT inhibitor" or "nicotinamide phosphoribosyl transferase inhibitor" is a compound that reduces the activity of nicotinamide phosphoribosyl transferase (NMPRT). In some embodiments, the NMPRT inhibitor reduces the activity of NMPRT by 50% or more, 75% or more, 80% or more, 85% or more, 90% or more, 95% or more, 98% or more, 99% or more, 99.9% or more, 99.99% or more, 99.999% or 99.999% or more. NMPRT activity can be measured using any technique known in the art, including indirect techniques such as measurement of cellular $NAD^+$ level. The term "NMPRT inhibitor" also includes a pharmaceutically acceptable salt of a NMPRT inhibitor, and/or a prodrug of a NMPRT inhibitor. A Pyridyl Cyanoguanidine or a Prodrug Thereof is a NMPRT inhibitor. When administered together with a DNA damaging therapy, in one embodiment, the NMPRT inhibitor is administered prior to administering the DNA damaging therapy; in another embodiment, the NMPRT inhibitor and the DNA damaging therapy are administered concurrently.

As used herein "NAD" and "$NAD^+$" are meant to be synonyms.

As used herein, "nicotinic acid" and "niacin" are meant to be synonyms.

As used herein, "nicotinic acid salvage pathway" or "nicotinic acid pathway" refers to the portion of the salvage pathway for NAD synthesis that starts with nicotinic acid.

As used herein "CLL" refers to chronic lymphocytic leukemia, which is also known as chronic lymphoid leukemia.

The term "rescue," as used herein, means increase in survival of cells or patients. In other words, the term "rescue" means decrease in mortality of cells or patients. In some embodiments, the cells or patients that are rescued, or not rescued, have been treated with a NMPRT inhibitor.

The following abbreviations are used herein and have the indicated definitions: IHC is immunohistochemistry, SD is standard deviation, RT is radiation therapy, NA is nicotinic acid, NM is nicotinamide, NMPRT is nicotinamide phosphoribosyl transferase (or nicotinamide phosphoribosyltransferase), NAPRT is nicotinic acid phosphoribosyl transferase (or nicotinic acid phosphoribosyltransferase), CI is combination index, BSTFA is bistrimethyl-silyl-trifluoroacetamide, DCM is dichloromethane, ESI is electrospray ionization, GC is gas chromatography, LC is liquid chromatography, FACS is fluorescence-activated cell-sorting, MS is mass spectroscopy, and TLC is thin layer chromatography, DMSO is dimethyl sulfoxide, MS is mass spectrometry, LC-MS or LC/MS is liquid chromatography/mass spectrometry, GC/MS is gas chromatography/mass spectrometry, ESI is electrospray ionization, ACN is acetonitrile, EI is electron impact, ATP is adenosine triphosphate, 2-ClAde is 2-chloroadenosine, m/z is mass-to-charge ratio, PRPP is phosphoribosyl pyrophosphate, PPI is pyrophosphate, IPTG is isopropyl β-D-1-thiogalactopyranoside, His is histidine, NMNAT1 is nicotinamide nucleotide adenylyltransferase 1, GFP is green fluorescent protein, EDTA is ethylenediaminetetraacetic acid, NCI is National Cancer Institute, GAPDH is glyceraldehyde-3-phosphate dehydrogenase, PBS is phosphate buffered saline, cc is cubic centimeter, and USP is United States Pharmacopeia.

6.2 Pyridyl Cyanoguanidines

Pyridyl Cyanoguanidines and methods of making same have been described before, for example in U.S. Pat. Nos. 5,696,140 and 5,563,160, and WO/1994/006770, the disclosures of all of which are incorporated by reference herein in their entirety.

In one aspect, a Pyridyl Cyanoguanidine is a compound having the formula II

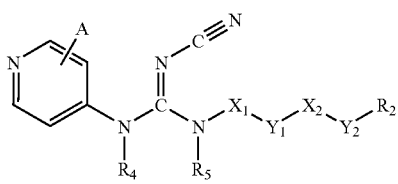

or a pharmaceutically acceptable salt thereof, wherein $X_1$ and $X_2$ are independently a bond, a straight, branched and/or cyclic hydrocarbon diradical which is unsubstituted or substituted with one or more hydroxy, halogen, nitro, amino, cyano, aminosulfonyl, alkylsulfonylamino, alkylcarbonyl, formyl, aminocarbonyl or alkylcarbonylamino; a heteroarylene or non-aromatic heterocyclic hydrocarbon diradical, each of which is unsubstituted or substituted with one or more straight, branched and/or cyclic non-aromatic hydrocarbon radical, hydroxyl, halogen, amino, nitro, cyano, aminosulfonyl, alkylsulfonylamino, alkylcarbonyl, formyl, aminocarbonyl or alkylcarbonylamino;

each $Y_1$ and $Y_2$ is independently a bond, an ether diradical (R'—O—R"), an amine diradical (R'—N—R"), O, S, S(O), S(O)$_2$, C(O), NH—CO, CO—NH, SO$_2$—N(R'), methylene or N(R')—SO$_2$ wherein R' and R" are independently a straight or branched hydrocarbon diradical containing 1-4 carbon atoms;

$R_2$ is aryl, heteroaryl or a non-aromatic heterocyclic hydrocarbon radical, tetrahydropyranyloxy, di-($C_{1-4}$ alkoxy) phosphinoyloxy and $C_{1-4}$ alkoxycarbonylamino, all of which can be unsubstituted or substituted with one or more of halogen, trifluoromethyl, hydroxy, $C_{1-4}$ alkoxy, $C_{1-4}$ alkoxycarbonyl, nitro, cyano, amino, aminocarbonyl, sulfamoyl, $C_{1-4}$ alkyl or $C_{1-4}$ hydroxyalkyl, wherein the $C_{1-4}$ alkyl and $C_{1-4}$ hydroxyalkyl are unsubstituted or substituted with one or more of halogen, hydroxyl, cyano or nitro;

each $R_4$ and $R_5$ is independently represent hydrogen; a straight, branched and/or cyclic hydrocarbon radical, all of which other than hydrogen can be substituted with one or more of halogen, hydroxyl, halogen, amino, nitro or cyano; and A represents hydrogen, an substituted or unsubstituted straight, branched and/or cyclic hydrocarbon radical, hydroxy, halogen, nitro, cyano, heteroaryl, heteroaralkyl or thiol.

Illustrative compounds of formula II include: 4-[N'-cyano-N"-(6-(4-chlorophenoxy)-hexyl)-N-guanidino]-pyridine; 4-[N'-cyano-N"-(9-(diethoxyphosphinoyloxy)-nonyl)-N-guanidino]-pyridine; and 4-[N'-cyano-N"-(12-(tert-butyloxycarbonylamino)-dodecyl)-N-guanidino]-pyridine.

A specific example of a Pyridyl Cyanoguanidine is 4-[N'-cyano-N"-(6-(4-chlorophenoxy)-hexyl)-N-guanidino]-pyridine, also referred to as Compound 1.

6.3 Pyridyl Cyanoguanidine Prodrugs

Pyridyl Cyanoguanidine prodrugs and methods of making same have been described before, for example in U.S. Pat. Nos. 6,525,077 and 7,253,193, and WO/2003/097602, the disclosures of all of which are incorporated by reference herein in their entirety.

In one aspect, a Pyridyl Cyanoguanidine prodrug is a compound having the formula Ia

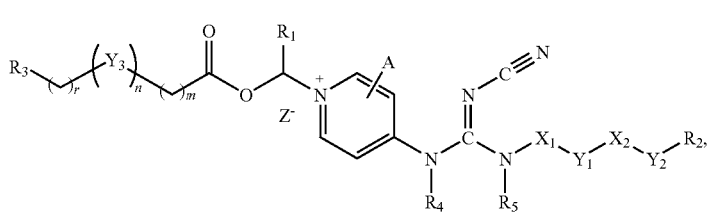

the formula Ib

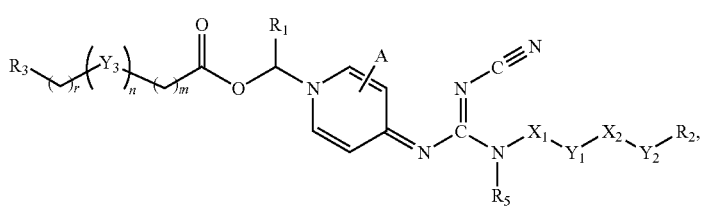

or a pharmaceutically acceptable salt thereof, wherein $X_1$ and $X_2$ are independently a bond, a straight, branched and/or cyclic hydrocarbon diradical which is unsubstituted or substituted with one or more hydroxy, halogen, nitro, amino, cyano, aminosulfonyl, alkylsulfonylamino, alkylcarbonyl, formyl, aminocarbonyl or alkylcarbonylamino; a heteroarylene or non-aromatic heterocyclic hydrocarbon diradical, each of which is unsubstituted or substituted with one or more straight, branched and/or cyclic non-aromatic hydrocarbon radical, hydroxyl, halogen, amino, nitro, cyano, aminosulfonyl, alkylsulfonylamino, alkylcarbonyl, formyl, aminocarbonyl or alkylcarbonylamino;

each $Y_1$ and $Y_2$ is independently a bond, an ether diradical (R'—O—R"), an amine diradical (R'—N—R"), O, S, S(O), S(O)$_2$, C(O), NH—CO, CO—NH, SO$_2$—N(R'), methylene or N(R')—SO₂ wherein R' and R" are independently a straight or branched hydrocarbon diradical containing 1-4 carbon atoms;

$Y_3$ is O, O—C(O), C(O)—O, or N(R₈); R₈ is hydrogen or $C_{1-4}$ alkyl;

$R_1$ is hydrogen or straight, branched and/or cyclic alkyl, all of which other than hydrogen are unsubstituted or substituted with phenyl; aryl; aralkyl or an aromatic hydrocarbon radical;

$R_2$ is aryl, heteroaryl or a non-aromatic heterocyclic hydrocarbon radical, tetrahydropyranyloxy, di-($C_{1-4}$ alkoxy) phosphinoyloxy and $C_{1-4}$ alkoxycarbonylamino, all of which can be unsubstituted or substituted with one or more of halogen, trifluoromethyl, hydroxy, $C_{1-4}$ alkoxy, $C_{1-4}$ alkoxycarbonyl, nitro, cyano, amino, aminocarbonyl, sulfamoyl, $C_{1-4}$ alkyl or $C_{1-4}$ hydroxyalkyl, wherein the $C_{1-4}$ alkyl and $C_{1-4}$ hydroxyalkyl are unsubstituted or substituted with one or more of halogen, hydroxyl, cyano or nitro;

$R_3$ is hydrogen, a straight, branched and/or cyclic hydrocarbon radical, all of which other than hydrogen can be substituted with one or more amino, hydroxy, carboxy, halogen, nitro, cyano, alkoxy, aminocarbonyl, $C_{1-4}$ alkoxycarbonyl, $C_{1-4}$ alkoxycarbonylamino, sulfo, hydroxysulfonyloxy, dihydroxyphosphinoyloxy, phosphono, sulfamino, aminosulfonyl, aminoacylamino or dialkoxyphosphinoyl; heteroaryl or a non-aromatic heterocyclic hydrocarbon radical, all of which can be substituted with one or more straight, branched and/or cyclic hydrocarbon radical, amino, hydroxy, carboxy, halogen, nitro, cyano, alkoxy, aminocarbonyl, $C_{1-4}$ alkoxycarbonyl, $C_{1-4}$ alkoxycarbonylamino, sulfo, hydroxysulfonyloxy, dihydroxyphosphinoyloxy, phosphono, sulfamino, aminosulfonyl, aminoacylamino or dialkoxyphosphinoyl;

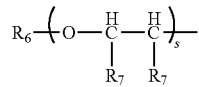

wherein s is an integer from 1 to 200; $R_6$ is hydrogen or a substituted or unsubstituted non-aromatic hydrocarbon radical; each $R_7$ is independently hydrogen or methyl;

each $R_4$ and $R_5$ is independently represent hydrogen; a straight, branched and/or cyclic hydrocarbon radical, all of which other than hydrogen can be substituted with one or more of halogen, hydroxyl, halogen, amino, nitro or cyano;

A represents hydrogen, an substituted or unsubstituted straight, branched and/or cyclic hydrocarbon radical, hydroxy, halogen, nitro, cyano, heteroaryl, heteroaralkyl or thiol;

$Z^-$ is a pharmaceutically acceptable anion;

each m and r is independently an integer from 0 to 4; and n is 0 or 1.

In some embodiments, $Z^-$ is chloride, bromide, iodide, sulfate, methanesulfonate, p-toluenesulfonate, nitrate or phosphate.

Illustrative compounds of formula Ia or Ib include:

1-[2-(2-(2-Methoxyethoxy)-ethoxy)-ethoxy-carbonyloxymethyl]-4-[N'-cyano-N"-(6-(4-chlorophenoxy)-hexyl)-N-guanidino]-pyridinium chloride;

1-[2-(2-Methoxyethoxy)-ethoxy-carbonyloxymethyl]-4-[N'-cyano-N"-(6-(4-chlorophenoxy)-hexyl)-N-guanidino]-pyridinium chloride;

1-[2-Methoxyethoxy)-carbonyloxymethyl]-4-[N'-cyano-N"-(6-(4-chlorophenoxy)-hexyl)-N-guanidino]-pyridinium chloride;

1-[2-(2-(2-Methoxyethoxy)-ethoxy)-ethoxy-carbonyloxymethyl]-4-[N'-cyano-N"-(6-(4-chlorophenoxy)-hexyl)-N-guanidino]-pyridinium iodide;

N-[1-(2-(2-(2-Methoxyethoxy)-ethoxy)-ethoxycarbonyloxymethyl)-1,4-dihydropyridin-4-ylidene]-N'-cyano-N"-(6-(4-chlorophenoxy)-hexyl)-guanidine;

1-[2-(2-(2-Methoxyethoxy)-ethoxy)-ethoxy-carbonyloxymethyl]-4-[N'-cyano-N"-(6-(4-chlorophenoxy)-hexyl)-N-guanidino]-pyridinium chloride;

1-[1-(2-(2-Methoxyethoxy)-ethoxy-carbonyloxy)-ethyl]-4-[N'-cyano-N"-(6-(4-chlorophenoxy)-hexyl)-N-guanidino]-pyridinium chloride;

1-[2-(2-(2-Methoxyethoxy)-ethoxy)-ethoxy-acetoxymethyl]-4-[N'-cyano-N"-(6-(4-chlorophenoxy)-hexyl)-N-guanidino]-pyridinium chloride;

1-[2-(2-(2-(2-Methoxyethoxy)-ethoxy)-ethoxy)-ethoxy-carbonyloxymethyl]-4-[N'-cyano-N"-(6-(4-chlorophenoxy)-hexyl)-N-guanidino]-pyridinium chloride;

1-Pivaloyloxymethyl-4-[N'-cyano-N"-(6-(4-chlorophenoxy)-hexyl)-N-guanidino]-pyridinium chloride;

1-Acetoxymethyl-4-[N'-cyano-N"-(6-(4-chlorophenoxy)-hexyl)-N-guanidino]-pyridinium chloride;

1-(L)-Valyloxymethyl-4-[N'-cyano-N"-(6-(4-chlorophenoxy)-hexyl)-N-guanidino]-pyridinium chloride;

1-Glycyloxymethyl-4-[N'-cyano-N"-(6-(4-chlorophenoxy)-hexyl)-N-guanidino]-pyridinium chloride;

1-[Monobenzyl succinyloxymethyl]-4-[N'-cyano-N"-(6-(4-chlorophenoxy)-hexyl)-N-guanidino]-pyridinium chloride;

1-[2-(2-(2-(2-Methoxyethoxy)-ethoxy)-ethoxy)-ethoxy carbonyloxymethyl]-4-[N'-cyano-N"-(6-(4-chlorophenoxy)-hexyl)-N-guanidino]-pyridinium chloride;

1-[2-(2-(2-(2-(2-Methoxyethoxy)-ethoxy)-ethoxy-ethoxy-ethoxy-carbonyloxymethyl]-4-[N'-cyano-N"-(6-(4-chlorophenoxy)-hexyl)-N-guanidino]-pyridinium chloride;

1-[2-(2-(2-Methoxyethoxy)-ethoxy)-ethoxy-carbonyloxymethyl]-4-[N'-cyano-N"-(9-(diethoxyphosphinoyloxy)-nonyl)-N-guanidino]-pyridinium chloride;

1-[2-(2-(2-Methoxyethoxy)-ethoxy)-ethoxy)-carbonyloxymethyl]-4-[N'-cyano-N"-(12-(tert-butyloxycarbonylamino)-dodecyl)-N-guanidino]-pyridinium iodide;

1-[2-(2-(2-Methoxyethoxy)-ethoxy)-ethoxy)-carbonyloxymethyl]-4-[N'-cyano-N"-(12-(tert-butyloxycarbonylamino)-dodecyl)-N-guanidino]-pyridinium chloride;

1-[2-(2-(2-Methoxyethoxy)-ethoxy)-ethoxy)-ethoxy-carbonyloxymethyl]-4-[N'-cyano-N"-(12-(tert-butyloxycarbonylamino)-dodecyl)-N-guanidino]-pyridinium chloride;

1-[3-(N-tert-butoxycarbonylamino)-propyloxy-carbonyloxymethyl]-4-[N'-cyano-N"-(6-(4-chlorophenoxy)-hexyl)-N-guanidino]-pyridinium iodide;

1-[3-Amino-propyloxy-carbonyloxymethyl]-4-[N'-cyano-N"-(6-(4-chlorophenoxy)-hexyl)-N-guanidino]-pyridinium chloride;

1-[3-(N-tert-butoxycarbonylamino)-propyl-carbamoyloxymethyl]-4-[N'-cyano-N"-(6-(4-chlorophenoxy)-hexyl)-N-guanidino]-pyridinium iodide;

1-[3-Aminopropyl-carbamoyloxymethyl]-4-[N'-cyano-N"-(6-(4-chlorophenoxy)-hexyl)-N-guanidino]-pyridinium chloride;

1-[5-(N-tert-butoxycarbonylamino)-pentanoyloxymethyl]-4-[N'-cyano-N"-(6-(4-chlorophenoxy)-hexyl)-N-guanidino]-pyridinium iodide;

1-[5-Amino-pentanoyloxymethyl]-4-[N'-cyano-N''-(6-(4-chlorophenoxy)-hexyl)-N-guanidino]-pyridinium chloride;

1-[3-(tert-butoxycarbonyl)-propionyloxymethyl]-4-[N'-cyano-N''-(6-(4-chlorophenoxy)-hexyl)-N-guanidino]-pyridinium chloride;

1-[3-carboxy-propionyloxymethyl]-4-[N'-cyano-N''-(6-(4-chlorophenoxy)-hexyl)-N-guanidino]-pyridinium chloride;

1-[N-(tert-butoxycarbonylmethyl)-carbamoyloxymethyl]-4-[N'-cyano-N''-(6-(4-chlorophenoxy)-hexyl)-N-guanidino]-pyridinium iodide;

1-[N-(carboxymethyl)-carbamoyloxymethyl]-4-[N'-cyano-N''-(6-(4-chlorophenoxy)-hexyl)-N-guanidino]-pyridinium chloride;

1-[1-(tert-butoxycarbonyl)-4-piperidyloxy-carbonyloxymethyl]-4-[N'-cyano-N''-(6-(4-chlorophenoxy)-hexyl)-N-guanidino]-pyridinium iodide;

1-[4-Piperidyloxy-carbonyloxymethyl]-4-[N'-cyano-N''-(6-(4-chloro-phenoxy)-hexyl)-N-guanidino]-pyridinium chloride;

1-[tert-butoxycarbonylmethoxy-carbonyloxymethyl]-4-[N'-cyano-N''-(6-(4-chlorophenoxy)-hexyl)-N-guanidino]-pyridinium iodide;

1-[Carboxymethoxy-carbonyloxymethyl]-4-[N'-cyano-N''-(6-(4-chlorophenoxy)-hexyl)-N-guanidino]-pyridinium chloride; and N-[1-(α-(2-(2-(2-Methoxyethoxy)-ethoxy)-ethoxycarbonyloxy)benzyl)-1,4-dihydropyridin-4-ylidene]-N'-cyano-N''-(6-(4-chlorophenoxy)-hexyl)-guanidine.

A specific example of a Pyridyl Cyanoguanidine prodrug is 1-[2-(2-(2-(2-Methoxyethoxy)-ethoxy)-ethoxy)-ethoxy-carbonyloxymethyl]-4-[N'-cyano-N''-(6-(4-chlorophenoxy)-hexyl)-N-guanidino]-pyridinium chloride, also referred to as Compound 2.

6.4 Nicotinic Acid

Nicotinic acid is also known as niacin. It is commercially available from many sources (e.g., Sigma-Aldrich; St. Louis, Mo.), and is a frequent ingredient in dietary supplements. In some embodiments, nicotinic acid is administered orally, for example, in the form of a capsule or a tablet. In other embodiments, nicotinic acid is administered parenterally, for example intravenously. Intravenous administration can be intermittent or continuous. In some embodiments, nicotinic acid is administered by infusion using a drip or an infusion pump.

Nicotinic acid can be administered, for example, either as a single dose or successively within a period of about 5 minutes, about 15 minutes, about 30 minutes, about 1 hour, about 90 minutes, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 49 hours, about 50 hours, about 51 hours, about 52 hours, about 53 hours, about 54 hours, about 55 hours, about 56 hours, about 57 hours, about 58 hours, about 59 hours, about 60 hours, about 61 hours, about 62 hours, about 63 hours, about 64 hours, about 65 hours, about 66 hours, about 67 hours, about 68 hours, about 69 hours, about 70 hours, about 71 hours, about 72 hours, about 73 hours, about 74 hours, about 75 hours, about 76 hours, about 77 hours, about 78 hours, about 79 hours, about 80 hours, about 81 hours, about 82 hours, about 83 hours, about 84 hours, about 85 hours, about 86 hours, about 87 hours, about 88 hours, about 89 hours, about 90 hours, about 91 hours, about 92 hours, about 93 hours, about 94 hours, about 95 hours, or about 96 hours. In one embodiment, nicotinic acid is administered successively within a period of about 72 hours. In another embodiment, nicotinic acid is administered as a single dose.

In one embodiment, nicotinic acid is administered in one or more doses within a period of time. In one embodiment, nicotinic acid is administered in 1 dose, 2 doses, 3 doses, 4 doses, or 5 doses within a period of time. In one embodiment, nicotinic acid is administered in 1 or 2 doses within a period of time. In a specific embodiment, nicotinic acid is administered in 1 or 2 doses within a period of about 24 hours. In one embodiment, each dose of nicotinic acid is administered as a single dose, or successively within a period of time.

Nicotinic acid can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the NMPRT inhibitor (e.g., a Pyridyl Cyanoguanidine or a Prodrug Thereof). In various embodiments, nicotinic acid and the NMPRT inhibitor (e.g., a Pyridyl Cyanoguanidine or a Prodrug Thereof) are administered 1 minute apart, 10 minutes apart, 30 minutes apart, less than 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, 12 hours to 24 hours apart, 24 hours to 48 hours apart, 48 hours to a week apart, a week to two weeks apart, two weeks to three weeks apart, three weeks to one month apart, one month to two months apart, two months to three months apart, or three months to six months apart.

In one embodiment, nicotinic acid and the NMPRT inhibitor are administered within 3 hours of each other. In another embodiment, nicotinic acid and the NMPRT inhibitor are administered 1 minute to 24 hours apart.

Nicotinic acid can be administered, for example, concurrently with, within about 5 minutes after, or about 15 minutes, about 30 minutes, about 1 hour, about 90 minutes, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 36 hours, about 2 days, about 3 days, about 4 days, about 5 days, about 6 days, about 7 days, about 8 days, about 9 days, about 10 days, about 11 days, about 12 days, about 13 days, or about 14 days after the NMPRT inhibitor has been administered. In one embodiment, nicotinic acid is administered about 1 hour after the NMPRT inhibitor has been administered. In another embodiment, nicotinic acid is administered within about 5 minutes after the NMPRT inhibitor has been administered.

In one specific embodiment, nicotinic acid and the NMPRT inhibitor are administered concurrently.

In one specific embodiment, nicotinic acid and the NMPRT inhibitor are each administered as a single dose and are administered concurrently.

In one specific embodiment, nicotinic acid and the NMPRT inhibitor are administered in the same composition.

6.5 Methods for Decreasing Cellular DNA Repair

A Pyridyl Cyanoguanidine or a Prodrug Thereof is useful for decreasing cellular DNA repair in a target patient (e.g., a human) or in a target cell (e.g., a human cell).

The invention provides methods for decreasing cellular DNA repair in a target cell compared to a reference cell, comprising contacting the target cell with an effective amount of a Pyridyl Cyanoguanidine or a Prodrug Thereof.

In various embodiments, the decrease in cellular DNA repair is measured relative to a reference cell. For example, the decrease can be more than 10%, more than 20%, more than 30%, more than 50%, more than 75%, more than 90%, more than 95%, or more than 99% compared to the reference cell. In one embodiment, the reference cell is a target cell prior to the administration of a Pyridyl Cyanoguanidine or a Prodrug Thereof. In another embodiment, the reference cell is a cell that has not been administered a Pyridyl Cyanoguanidine or a Prodrug Thereof. In another embodiment, the reference cell is normal, wild-type, or a healthy cell. In one embodiment, the reference cell is an isolated cell, for example a cell in a tissue culture.

The invention provides methods for decreasing cellular DNA repair in a target patient compared to a reference patient, comprising administering to the target patient in need of such treatment an effective amount of a Pyridyl Cyanoguanidine or a Prodrug Thereof.

In various embodiments, the decrease in cellular DNA repair is measured relative to a reference patient. For example, the decrease can be more than 10%, more than 20%, more than 30%, more than 50%, more than 75%, more than 90%, more than 95%, or more than 99% compared to the reference patient. In one embodiment, the reference patient is a target patient prior to the administration of a Pyridyl Cyanoguanidine or a Prodrug Thereof. In one embodiment, the target patient and the reference patient is a human. In one embodiment, the reference patient is a patient that has not been administered a Pyridyl Cyanoguanidine or a Prodrug Thereof. In another embodiment, the reference patient is a normal and/or a healthy patient.

6.6 Methods for Decreasing Cellular NAD$^+$ Biosynthesis

A Pyridyl Cyanoguanidine or a Prodrug Thereof is useful for decreasing cellular NAD$^+$ biosynthesis in a target patient (e.g., a human) or in a target cell (e.g., a human cell). In one embodiment, the target patient and the reference patient are humans.

The invention provides methods for decreasing cellular NAD$^+$ biosynthesis in a target cell compared to a reference cell, comprising contacting the target cell with an effective amount of a Pyridyl Cyanoguanidine or a Prodrug Thereof.

In various embodiments, the decrease in cellular NAD$^+$ biosynthesis is measured relative to a reference cell. For example, the decrease can be more than 10%, more than 20%, more than 30%, more than 50%, more than 75%, more than 90%, more than 95%, or more than 99% compared to the reference cell. In one embodiment, the reference cell is the target cell prior to the administration of a Pyridyl Cyanoguanidine or a Prodrug Thereof. In another embodiment, the reference cell is a cell that has not been administered a Pyridyl Cyanoguanidine or a Prodrug Thereof. In another embodiment, the reference cell is normal, wild-type, or a healthy cell. In one embodiment, the reference cell is an isolated cell, for example a cell in a tissue culture.

The invention provides methods for decreasing cellular NAD$^+$ biosynthesis in a target patient compared to a reference patient, comprising administering to the target patient in need of such treatment an effective amount of a Pyridyl Cyanoguanidine or a Prodrug Thereof.

In various embodiments, the decrease in cellular NAD$^+$ biosynthesis is measured relative to a reference patient. For example, the decrease can be more than 10%, more than 20%, more than 30%, more than 50%, more than 75%, more than 90%, more than 95%, or more than 99% compared to the reference patient. In one embodiment, the reference patient is the target patient prior to the administration of a Pyridyl Cyanoguanidine or a Prodrug Thereof. In one embodiment, the reference patient is a patient that has not been administered a Pyridyl Cyanoguanidine or a Prodrug Thereof. In another embodiment, the reference patient is a normal or a healthy patient.

6.7 Methods for Modulating Nicotinamide Phosphoribosyl Transferase (NMPRT) Activity A Pyridyl Cyanoguanidine or a Prodrug Thereof is useful for modulating nicotinamide phosphoribosyl transferase activity in a patient (e.g., a human) or in a cell (e.g., a human cell).

The invention provides methods for modulating nicotinamide phosphoribosyl transferase (NMPRT) activity in a target cell compared to a reference cell, comprising contacting the target cell with an effective amount of a Pyridyl Cyanoguanidine or a Prodrug Thereof. In some embodiments, the target cell is a human cell. In other embodiments, the target cell is a cancer cell.

In one embodiment, modulating NMPRT activity comprises decreasing or inhibiting NMPRT activity. In various embodiments, modulation of NMPRT activity is measured relative to a reference cell. If modulation is a decrease in NMPRT activity, the decrease can be about 10%, about 20%, about 30%, about 50%, about 75%, about 90%, about 95%, or about 100% compared to the reference cell.

In one embodiment, the reference cell is a target cell prior to the administration of a Pyridyl Cyanoguanidine or a Prodrug Thereof. In one embodiment, the reference is a cell that has not been administered a Pyridyl Cyanoguanidine or a Prodrug Thereof. In another embodiment, the reference cell is a normal, a wild-type, or a healthy cell. In another embodiment, the reference cell is a non-cancerous cell. In one embodiment, the cell is an isolated cell, for example a cell in a tissue culture.

The invention provides methods for modulating nicotinamide phosphoribosyl transferase (NMPRT) activity in a target patient compared to a reference patient, comprising administering to a target patient in need of such treatment an effective amount of a Pyridyl Cyanoguanidine or a Prodrug Thereof.

In various embodiments, modulation of NMPRT activity is measured relative to a reference patient. If modulation is a decrease in NMPRT activity, the decrease can be more than 10%, more than 20%, more than 30%, more than 50%, more than 75%, more than 90%, more than 95%, or more than 99% compared to the reference patient. In one embodiment, the reference patient is a target patient prior to the administration of a Pyridyl Cyanoguanidine or a Prodrug Thereof. In another embodiment, the reference patient is a patient that has not been administered a Pyridyl Cyanoguanidine or a Prodrug Thereof. In some embodiments, the reference patient is a normal or a healthy patient. In various embodiments, the target and the reference patient is a human.

6.8 Methods for Sensitizing a Patient or a Cancer Cell to DNA Damaging Therapy A NMPRT inhibitor (e.g., a Pyridyl Cyanoguanidine or a Prodrug Thereof) is useful for sensitizing a patient (e.g., a human) or a cell (e.g., a human cell) to DNA damaging therapy.

The invention provides methods for sensitizing a cancer cell to DNA damaging therapy, comprising contacting the cell with an effective amount of a NMPRT inhibitor (e.g., a Pyridyl Cyanoguanidine or a Prodrug Thereof). A sensitized cell is more susceptible or amenable to DNA damaging therapy than a non-sensitized cell, i.e., a DNA damaging therapy is more effective in a sensitized cell compared to a non-sensitized cell. In some embodiments, the cell is a cancer cell.

In various embodiments, sensitization of the target cell is measured relative to a reference cell. For example, the sensitization can be by more than 10%, more than 20%, more than 30%, more than 50%, more than 75%, more than 90%, more than 95%, more than 100%, more than 1.5-fold, more than 2-fold, more than 5-fold, more than 10-fold, more than 50-fold, more than 100-fold, or more than 1,000-fold, when compared to the reference cell. In one embodiment, the reference cell is the target cell prior to the administration of a NMPRT inhibitor (e.g., a Pyridyl Cyanoguanidine or a Prodrug Thereof). In another embodiment, the reference cell is a normal, a wild-type, or a healthy cell. In one embodiment, the cell is an isolated cell, for example a cell in a tissue culture.

The invention provides methods for sensitizing a patient to DNA damaging therapy, comprising administering to a patient in need of such treatment an effective amount of a NMPRT inhibitor (e.g., a Pyridyl Cyanoguanidine or a Prodrug Thereof). In a particular embodiment, the DNA damaging therapy is radiation therapy. A sensitized patient is more susceptible or amenable to DNA damaging therapy than a non-sensitized patient, i.e., a DNA damaging therapy is more effective in a sensitized patient compared to a non-sensitized patient. In some embodiments, the patient is a human.

In some embodiments, the sensitization is measured relative to a reference patient. For example, the sensitization can be by more than 10%, more than 20%, more than 30%, more than 50%, more than 75%, more than 90%, more than 95%, more than 100%, more than 1.5-fold, more than 2-fold, more than 5-fold, more than 10-fold, more than 50-fold, more than 100-fold, or more than 1,000-fold, when compared to the reference patient. In one embodiment, the reference patient is the patient prior to the administration of a NMPRT inhibitor (e.g., a Pyridyl Cyanoguanidine or a Prodrug Thereof). In another embodiment, the reference patient is a normal or a healthy patient.

In one embodiment, the NMPRT inhibitor (e.g., a Pyridyl Cyanoguanidine or a Prodrug Thereof) is administered prior to DNA damaging therapy. In another embodiment, the NMPRT inhibitor (e.g., a Pyridyl Cyanoguanidine or a Prodrug Thereof) is administered concurrently with DNA damaging therapy.

In a particular embodiment, the DNA damaging therapy comprises administering a DNA damaging chemotherapeutic agent. In some embodiments, the DNA damaging chemotherapeutic agent is Cladribine, Pentostatin, Methotrexate, Trimetrexate glucuronate, Pemetrexed, Treosulfan, Busulfan, Dacarbazine, Temozolomide, Mitomycin C, Chlorambucil, Ifosfamide, Melphalan, Thiotepa, Mechlorethamine, Carmustine, Bendamustin, Fotemustine, Lomustine, Streptozocin, Carboplatin, Cisplatin, Lobaplatin, Oxaliplatin Bleomycin, Hydroxyurea, Actinomycin D, Azacitidine, Decitabine, Nelarabine, Cytarabine, Fludarabine, Clofarabine, Vorinostat, Gemcitabine, 5-Fluorouracil, Capecitabine, Floxuridine, Raltitrexed, Pemetrexed, Irinotecan, Topotecan, Amrubicin, Daunorubicin, Doxorubicin, Epirubicin, Etoposide, Idarubicin, Mitoxantrone, Teniposide, Valrubicin, Allopurinol, or a pharmaceutically acceptable salt thereof.

In other embodiments, the DNA damaging therapy comprises radiation therapy.

6.9 The Patient in Need of Treatment with Compounds and/or Compositions Described Herein In some embodiments, the patient in need of treatment with compounds and/or compositions described herein is considered to be in need of a DNA damaging therapy. In some embodiments, the DNA damaging therapy comprises administering a DNA damaging chemotherapeutic agent.

In one embodiment, the patient in need of DNA damaging therapy is diagnosed with or suspected to have chronic lymphocytic leukemia ("CLL").

In still another embodiment, the patient in need of DNA damaging therapy has previously undergone or is presently undergoing treatment for cancer. Such previous treatments include, but are not limited to, prior chemotherapy, radiation therapy, surgery or immunotherapy, such as cancer vaccines.

6.10 Multi-Therapy with a NMPRT Inhibitor

A NMPRT inhibitor can be administered to a patient that has undergone or is currently undergoing DNA damaging therapy including, radiation therapy, or administration of a DNA damaging chemotherapeutic agent.

In some embodiments, the NMPRT inhibitor is a Pyridyl Cyanoguanidine or a Prodrug Thereof. In another embodiment, the NMPRT inhibitor is (E)-N-[4-(1-benzoylpiperidin-4-yl)butyl]-3-(pyridin-3-yl)acrylamide.

In one embodiment, the invention provides methods for decreasing cellular DNA repair in a target patient in need thereof compared to a reference patient comprising administering to the target patient: (a) an effective amount of a NMPRT inhibitor; and (b) DNA damaging therapy including, but not limited to, radiation therapy, or administration of a DNA damaging chemotherapeutic agent.

In another embodiment, the invention provides methods for decreasing cellular $NAD^+$ biosynthesis in a target patient in need thereof compared to a reference patient comprising administering to the target patient: (a) an effective amount of a NMPRT inhibitor; and (b) DNA damaging therapy including, but not limited to, radiation therapy, or administration of a DNA damaging chemotherapeutic agent.

In another embodiment, the invention provides methods for modulating nicotinamide phosphotransferase activity in a patient in need thereof comprising administering to the patient: (a) an effective amount of a NMPRT inhibitor; and (b) DNA damaging therapy including, but not limited to, radiation therapy, or administration of a DNA damaging chemotherapeutic agent. In another embodiment, the invention provides methods for increasing efficiency of radiation therapy in a target patient in need thereof compared to a reference patient comprising administering to the target patient: (a) an effective amount of a NMPRT inhibitor; (b) DNA damaging therapy including, but not limited to, radiation therapy.

In another embodiment, the invention provides methods for sensitizing a patient in need of a DNA damaging therapy to the DNA damaging therapy comprising administering to the patient: (a) an effective amount of a NMPRT inhibitor; and (b) DNA damaging therapy including, but not limited to, radiation therapy, or a DNA damaging chemotherapeutic agent.

A NMPRT inhibitor can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the DNA damaging therapy. In various embodiments, a NMPRT inhibitor, and the DNA damaging therapy are administered 1 minute apart, 10 minutes apart, 30 minutes apart, less than 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart, no more than 48 hours apart, no more than one week apart, no more than two weeks apart, no more than three weeks apart, no more than one month apart, no more than two months apart, no more than three months apart or no more than six months apart. In one embodiment, a the NMPRT inhibitor, and the DNA damaging therapy are administered within 3 hours of each other. In another embodiment, a NMPRT inhibitor, and the DNA damaging therapy are administered 1 minute to 24 hours apart.

The DNA damaging therapy can be administered, for example, concurrently with, within about 5 minutes after, or about 15 minutes, about 30 minutes, about 1 hour, about 90 minutes, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 36 hours, about 2 days, about 3 days, about 4 days, about 5 days, about 6 days, about 7 days, about 8 days, about 9 days, about 10 days, about 11 days, about 12 days, about 13 days, or about 14 days after the NMPRT inhibitor has been administered. In one embodiment, the DNA damaging therapy is administered about 1 hour after the NMPRT inhibitor has been administered. In a specific embodiment, the DNA damaging therapy is administered concurrently with the NMPRT inhibitor. In another embodiment, the DNA damaging therapy is administered within about 5 minutes after the NMPRT inhibitor has been administered.

The NMPRT inhibitor can be administered, for example, either as a single dose or successively within a period of about 5 minutes, about 15 minutes, about 30 minutes, about 1 hour, about 90 minutes, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 49 hours, about 50 hours, about 51 hours, about 52 hours, about 53 hours, about 54 hours, about 55 hours, about 56 hours, about 57 hours, about 58 hours, about 59 hours, about 60 hours, about 61 hours, about 62 hours, about 63 hours, about 64 hours, about 65 hours, about 66 hours, about 67 hours, about 68 hours, about 69 hours, about 70 hours, about 71 hours, about 72 hours, about 73 hours, about 74 hours, about 75 hours, about 76 hours, about 77 hours, about 78 hours, about 79 hours, about 80 hours, about 81 hours, about 82 hours, about 83 hours, about 84 hours, about 85 hours, about 86 hours, about 87 hours, about 88 hours, about 89 hours, about 90 hours, about 91 hours, about 92 hours, about 93 hours, about 94 hours, about 95 hours, or about 96 hours. In one embodiment, the NMPRT inhibitor is administered successively within a period of about 72 hours. In another embodiment, the NMPRT inhibitor is administered as a single dose.

In one embodiment, the NMPRT inhibitor is administered in one or more doses within a period of time. In one embodiment, the NMPRT inhibitor is administered in 1 dose, 2 doses, 3 doses, 4 doses, or 5 doses within a period of time. In one embodiment, the NMPRT inhibitor is administered in 1 or 2 doses within a period of time. In a specific embodiment, the NMPRT inhibitor is administered in 1 or 2 doses within a period of about 24 hours. In one embodiment, each dose of the NMPRT inhibitor is administered as a single dose, or successively within a period of time.

The DNA damaging therapy can be administered, for example, as a single dose or successively within a period of about 5 minutes, about 15 minutes, about 30 minutes, about 1 hour, about 90 minutes, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 49 hours, about 50 hours, about 51 hours, about 52 hours, about 53 hours, about 54 hours, about 55 hours, about 56 hours, about 57 hours, about 58 hours, about 59 hours, about 60 hours, about 61 hours, about 62 hours, about 63 hours, about 64 hours, about 65 hours, about 66 hours, about 67 hours, about 68 hours, about 69 hours, about 70 hours, about 71 hours, about 72 hours, about 73 hours, about 74 hours, about 75 hours, about 76 hours, about 77 hours, about 78 hours, about 79 hours, about 80 hours, about 81 hours, about 82 hours, about 83 hours, about 84 hours, about 85 hours, about 86 hours, about 87 hours, about 88 hours, about 89 hours, about 90 hours, about 91 hours, about 92 hours, about 93 hours, about 94 hours, about 95 hours, or about 96 hours. In one embodiment, the DNA damaging therapy is administered successively within a period of about 24 hours. In one embodiment, the DNA damaging therapy is administered successively within a period of about 72 hours. In another embodiment, the DNA damaging therapy is administered as a single dose.

In one embodiment, the DNA damaging therapy is administered in one or more doses within a period of time. In one embodiment, the DNA damaging therapy is administered in 1 dose, 2 doses, 3 doses, 4 doses, or 5 doses within a period of time. In one embodiment, the DNA damaging therapy is administered in 1 or 2 doses within a period of time. In a specific embodiment, the DNA damaging therapy is administered in 1 or 2 doses within a period of about 24 hours. In one embodiment, each dose of the chemotherapeutic agent is administered as a single dose, or successively within a period of time.

In one specific embodiment, the NMPRT inhibitor is administered either as a single dose or successively within a period of from about 5 minutes to about 24 hours, followed by administering DNA damaging therapy either as a single dose or successively within a period of from about 5 minutes to about 24 hours, and wherein the DNA damaging therapy is administered from within about 5 minutes after to about 14 days after the NMPRT inhibitor has been administered, and wherein the sum of the NMPRT inhibitor and the DNA damaging therapy is effective for treating cancer or a neoplastic disease.

In one specific embodiment, the NMPRT inhibitor is administered as a single dose, DNA damaging therapy is administered in one or more doses within a period of about 24 hours, the DNA damaging therapy is administered from within about 5 minutes after to about 14 days after the NMPRT inhibitor has been administered, and each dose of the DNA damaging therapy is administered as a single dose within the period or successively within the period. In one embodiment, the DNA damaging therapy is administered from within about 5 minutes after to about 24 hours after, or from within about 5 minutes after to about 1 hour after, the NMPRT inhibitor has been administered. In one embodiment, the DNA damaging therapy is administered in 1 or 2 doses within a period of about 24 hours.

In one specific embodiment, the NMPRT inhibitor is administered as a single dose and DNA damaging therapy is administered as a single dose. In one specific embodiment, the NMPRT inhibitor is administered as a single dose and DNA damaging therapy is administered as a single dose within about 5 minutes after the NMPRT inhibitor has been administered. In one specific embodiment, NMPRT inhibitor and DNA damaging therapy are administered concurrently. In another specific embodiment, the NMPRT inhibitor and DNA damaging therapy are each administered as a single dose and are administered at the same time. In one specific embodiment, the NMPRT inhibitor are administered in the same composition. In another embodiment, the DNA damaging therapy is radiation therapy. In yet another embodiment, the DNA damaging therapy comprises administering a DNA damaging chemotherapeutic agent.

6.11 DNA Damaging Therapy

In one embodiment, the DNA damaging therapy comprises administering a DNA damaging chemotherapeutic agent. Exemplary DNA damaging chemotherapeutic agents useful in the methods and compositions of the present invention include, but are not limited to, drugs listed in Table 2 and pharmaceutically acceptable salts thereof.

TABLE 2

| Target | Generic name |
|---|---|
| Adenosine deaminase | Cladribine, Pentostatin |
| Dihydrofolate reductase | Methotrexate, Trimetrexate glucuronate, Pemetrexed, Treosulfan |
| DNA/Alkylating agent | Busulfan, Dacarbazine, Temozolomide, Mitomycin C |
| DNA/Alkylating agent/Nitrogen mustard | Chlorambucil, Ifosfamide, Melphalan, Thiotepa, Mechlorethamine |
| DNA/Alkylating agent/ Nitrosourea | Carmustine, Bendamustin, Fotemustine, Lomustine, Streptozocin |
| DNA/Alkylating agent/Platinum | Carboplatin, Cisplatin, Lobaplatin, Oxaliplatin |
| DNA/Free radicals | Bleomycin, Hydroxyurea |
| DNA/Intercalator | Actinomycin D |
| DNA methyltransferase | Azacitidine, Decitabine |
| DNA polymerase | Nelarabine, Cytarabine, Fludarabine, Clofarabine |
| Histone deacetylase | Vorinostat |
| Ribonucleotide reductase | Gemcitabine |
| Thymidylate synthase | 5-Fluorouracil, Capecitabine, Floxuridine, Raltitrexed, Pemetrexed |
| Glycinamide ribonucleotide formyltransferase (GARFT) | Pemetrexed |
| Topoisomerase I | Irinotecan, Topotecan |
| Topoisomerase II | Amrubicin, Daunorubicin, Doxorubicin, Epirubicin, Etoposide, Idarubicin, Mitoxantrone, Teniposide, Valrubicin |
| Xanthine oxidase | Allopurinol |

In some embodiments, the DNA damaging agent and the NMPRT inhibitor exhibit a synergistic effect as evidenced by a lower $IC_{50}$ value of the combination treatment compared to the treatment with the DNA damaging agent only. For example, temozolomide, carmustine, and streptozocin can act synergistically with a NMPRT inhibitor, such as a Pyridyl Cyanoguanidine or a Prodrug Thereof.

In another embodiment, DNA damaging therapy comprises administering radiation therapy.

6.12 Therapeutic/Prophylactic Administration of a NMPRT Inhibitor

Compositions comprising a NMPRT inhibitor are suitable for internal or external use and comprise a physiologically acceptable carrier or vehicle and an effective amount of NMPRT inhibitor.

A NMPRT inhibitor can be administered in amounts that are effective for decreasing cellular DNA repair in a human cell, decreasing cellular $NAD^+$ biosynthesis in a cell, increasing efficiency of radiation therapy in a cell, modulating nicotinamide phosphoribosyl transferase activity in a cell, decreasing cellular DNA repair in a patient, decreasing cellular $NAD^+$ biosynthesis in a patient, increasing efficiency of radiation therapy in a patient, modulating nicotinamide phosphoribosyl transferase activity in a patient, or sensitizing a human to a DNA damaging therapy.

Administration of a NMPRT inhibitor can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, compositions comprising an effective amount of a NMPRT inhibitor can be in solid, semi-solid or liquid dosage form, such as, for example, injectables, tablets, suppositories, pills, time-release capsules, elixirs, tinctures, emulsions, syrups, powders, liquids, suspensions, or the like, in one embodiment, in unit dosages and consistent with conventional pharmaceutical practices. Likewise, the compositions can also be administered in intravenous (both bolus and infusion), intraperitoneal, subcutaneous or intramuscular form, all using other forms known to those skilled in the art.

Illustrative pharmaceutical compositions include tablets and gelatin capsules. Illustrative (physiologically acceptable) carriers or vehicles include, but are not limited to: a) a diluent, e.g., lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algiic acid or its sodium salt, or effervescent mixtures; and/or e) absorbent, colorant, flavorant and sweetener.

Liquid, particularly injectable, compositions can, for example, be prepared by dissolution or dispersion. For example, a NMPRT inhibitor can be admixed with a pharmaceutically acceptable solvent such as, for example, water, saline, aqueous dextrose, glycerol, ethanol, and the like, to thereby form an injectable isotonic solution or suspension.

A NMPRT inhibitor can be also formulated as a suppository that can be prepared from fatty emulsions or suspensions, using polyalkylene glycols such as propylene glycol, as the carrier.

A NMPRT inhibitor can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564, incorporated herein by reference.

A NMPRT inhibitor can also be delivered by the use of monoclonal antibodies as individual carriers to which the NMPRT inhibitor is coupled. The NMPRT inhibitor can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the NMPRT inhibitor can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Parental injectable administration can be used for subcutaneous, intramuscular or intravenous injections and infusions. Injectables can be prepared in conventional forms, either as liquid solutions or suspensions or solid forms suitable for dissolving in liquid prior to injection.

In one embodiment, the NMPRT inhibitor is administered intravenously. One embodiment, for parenteral administration employs the implantation of a slow-release or sustained-released system, according to U.S. Pat. No. 3,710,795, incorporated herein by reference.

The compositions can be sterilized or can contain non-toxic amounts of adjuvants, such as preserving, stabilizing, wetting or emulsifying agents, solution promoters, salts for regulating the osmotic pressure pH buffering agents, and other substances, including, but not limited to, sodium acetate or triethanolamine oleate. In addition, the compositions can also contain other therapeutically useful substances.

Compositions can be prepared according to conventional mixing, granulating or coating methods, respectively, and the present pharmaceutical compositions can contain from about 0.1% to about 99%, preferably from about 1% to about 70% of the NMPRT inhibitor by weight or volume.

The dosage regimen utilizing the NMPRT inhibitor can be selected in accordance with a variety of factors including type, species, age, weight, sex and medical condition of the patient; the severity of the condition of the patient in need of treatment with a NMPRT inhibitor, or a cell, is in; the route of administration; the renal or hepatic function of the patient; and the particular NMPRT inhibitor employed. A person skilled in the art can readily determine or prescribe the effective amount of the NMPRT inhibitor useful for achieving the desired effect in a cell or in a patient in need of treatment with a NMPRT inhibitor.

Effective dosage amounts of a NMPRT inhibitor, when administered to a patient, range from about 0.05 to about 1,000 mg of the NMPRT inhibitor per day. Compositions for in vivo or in vitro use can contain about 0.5, 1.0, 2.5, 5.0, 10.0, 15.0, 25.0, 50.0, 100.0, 250.0, 500.0 or 1000.0 mg of the NMPRT inhibitor. In one embodiment, the compositions are in the form of a tablet that can be scored. Effective plasma levels of the NMPRT inhibitor can range from about 0.1 to 2.0 µg/mL. The amount of a NMPRT inhibitor that is effective for achieving the desired effect in a cell or in a patient in need of such treatment can be determined using clinical techniques that are known to those of skill in the art. In addition, in vitro and in vivo assays can optionally be employed to help identify optimal dosage ranges. The precise dose to be employed can also depend on the route of administration and the seriousness of the condition of a cell or a patient in need of such treatment and can be decided according to the judgment of the practitioner and each patient's circumstances in view of, e.g., published clinical studies. Suitable effective dosage amounts, however, can range from about 10 micrograms to about 5 grams about every 4 hours, in one embodiment, about 500 mg or less per every 4 hours. In one embodiment, the effective dosage is about 0.01 mg, 0.5 mg, about 1 mg, about 50 mg, about 100 mg, about 200 mg, about 300 mg, about 400 mg, about 500 mg, about 600 mg, about 700 mg, about 800 mg, about 900 mg, about 1 g, about 1.2 g, about 1.4 g, about 1.6 g, about 1.8 g, about 2.0 g, about 2.2 g, about 2.4 g, about 2.6 g, about 2.8 g, about 3.0 g, about 3.2 g, about 3.4 g, about 3.6 g, about 3.8 g, about 4.0 g, about 4.2 g, about 4.4 g, about 4.6 g, about 4.8 g, and about 5.0 g, every 4 hours. Equivalent dosages can be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The effective dosage amounts described herein refer to total amounts administered; that is, if more than one NMPRT inhibitor is administered, the effective dosage amounts correspond to the total amount administered.

A NMPRT inhibitor can be administered in a single daily dose, or the total daily dosage can be administered in divided doses of two, three or four times daily. Furthermore, a NMPRT inhibitor can be administered in intranasal form via topical use of suitable intranasal vehicles, or via transdermal routes, using those forms of transdermal skin patches known to those of skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of a NMPRT inhibitor ranges from about 0.1% to about 15%, weight/weight or weight/volume.

In one embodiment, the compositions comprise a total amount of a NMPRT inhibitor that is effective on its own. In another embodiment, the amount of NMPRT inhibitor is at least about 0.01% of the combined combination chemotherapy agents by weight of the composition. When intended for oral administration, this amount can be varied from about 0.1% to about 80% by weight of the composition. Some oral compositions can comprise from about 4% to about 50% of a NMPRT inhibitor. Other compositions of the present invention are prepared so that a parenteral dosage unit contains from about 0.01% to about 2% by weight of the composition.

The NMPRT inhibitor can be assayed in vitro or in vivo for the desired therapeutic or prophylactic activity prior to use in humans. Animal model systems can be used to demonstrate safety and efficacy.

The present methods for using a NMPRT inhibitor can further comprise administering another prophylactic or therapeutic agent to the patient being administered a NMPRT inhibitor. In one embodiment, the other prophylactic or therapeutic agent is administered in an effective amount. The other prophylactic or therapeutic agent includes, but is not limited to, an antiemetic agent, a hematopoietic colony stimulating factor, an anxiolytic agent, and an analgesic agent.

In a further embodiment, the NMPRT inhibitor can be administered prior to, concurrently with, or after the other prophylactic or therapeutic agent, or on the same day, or within 1 hour, 2 hours, 12 hours, 24 hours, 48 hours or 72 hours of each other.

Effective amounts of the prophylactic or therapeutic agents are known to those skilled in the art. However, it is well within the skilled artisan's purview to determine the other prophylactic or therapeutic agent's optimal effective amount range.

In one embodiment, the other prophylactic or therapeutic agent is an antiemetic agent. Antiemetic agents useful in the methods of the present invention include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine and tropisetron.

In one embodiment, the other prophylactic or therapeutic agent is a hematopoietic colony stimulating factor. Hematopoietic colony stimulating factors useful in the methods of the present invention include, but are not limited to, filgrastim, sargramostim, molgramostim and epoietin alfa.

In one embodiment, the other prophylactic or therapeutic agent is an opioid analgesic agent. Opioid analgesic agents useful in the methods of the present invention include, but are not limited to, morphine, heroin, hydromorphone, hydrocodone, oxymorphone, oxycodone, metopon, apomorphine, normorphine, etorphine, buprenorphine, meperidine, lopermide, anileridine, etoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene.

In one embodiment, the other prophylactic or therapeutic agent is a non-opioid analgesic agent. Non-opioid analgesic agents useful in the methods of the present invention include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam and sulindac.

In one embodiment, the other prophylactic or therapeutic agent is an anxiolytic agent. Anxiolytic agents useful in the methods of the present invention include, but are not limited to, buspirone, and benzodiazepines such as diazepam, lorazepam, oxazapam, chlorazepate, clonazepam, chlordiazepoxide and alprazolam.

The compositions of the invention can be sold or used as prescription products, or alternatively as over-the-counter products. In one embodiment, the compositions of the invention can be sold or used as nutraceutical products.

6.13 Methods for Treating a Patient Who Received a Toxic Dose of a NMPRT Inhibitor An inhibitor of NMPRT can be more toxic to cancer cells than normal (healthy) cells. However, at a very high dose, inhibitors of NMPRT can lead to a lethal $NAD^+$ depletion even in normal cell. Because $NAD^+$ can be synthesized independently via nicotinic acid pathway from nicotinic acid, administration of nicotinic acid can replenish $NAD^+$ in normal cells and serve as an antidote to an overdose of a NMPRT inhibitor. Thus, nicotinic acid is useful for treating a patient who received a toxic dose of a NMPRT inhibitor. In some embodiments, the NMPRT inhibitor is a Pyridyl Cyanoguanidine or a Prodrug Thereof. In another embodiment, the NMPRT inhibitor is (E)-N-[4-(1-benzoylpiperidin-4-yl)butyl]-3-(pyridin-3-yl)acrylamide.

The invention provides methods for treating a patient (e.g., a human) who received a toxic dose of a NMPRT inhibitor comprising administering the patient in need thereof an effective amount of nicotinic acid. In one embodiment, the patient is a human.

In one embodiment, nicotinic acid is administered as an intravenous infusion at a dose of 2.8 mg/min for 1 h (90 mg/m$^2$ total). In another embodiment, nicotinic acid is administered as an intravenous infusion at a dose of 2.8 mg/min for 2 h (180 mg/m$^2$ total). In yet another embodiment, nicotinic acid is administered as an intravenous infusion at a dose of 2.8 mg/min for 3 h (270 mg/m$^2$ total). In still another embodiment, nicotinic acid is administered as an intravenous infusion at a dose of 2.8 mg/min for 4 h (90 mg/m$^2$/h; 360 mg/m$^2$ total). In a specific embodiment, administering the effective amount of nicotinic acid comprises intravenously administering nicotinic acid at to the human at dose of about 90 mg/m$^2$/h for at least four hours.

In some embodiments, the effective amount of nicotinic acid is administered orally, for example using a capsule or a tablet. Of course, any formulation suitable for oral administration can be used to deliver the effective amount of nicotinic acid to the patient.

6.14 Pharmaceutical Compositions Comprising a NMPRT Inhibitor and Nicotinic Acid In some embodiments, the invention provides a pharmaceutical composition useful for treating a patient diagnosed with or suspected to have a cancer deficient in nicotinic acid pathway, for decreasing cellular DNA repair in a target cell, decreasing cellular NAD+ biosynthesis in a target cell, increasing efficiency of radiation therapy in a target cell, modulating nicotinamide phosphoribosyl transferase activity in a cell, decreasing cellular DNA repair in a target patient, decreasing cellular NAD+ biosynthesis in a target patient, increasing efficiency of radiation therapy in a target patient, modulating nicotinamide phosphoribosyl transferase activity in a patient, sensitizing a patient to a DNA damaging therapy, or treating a patient diagnosed with or suspected to have a cancer deficient in nicotinic acid pathway.

In some embodiments, the pharmaceutical compositions comprise a physiologically acceptable carrier, and effective amount of a NMPRT inhibitor, and an effective amount of nicotinic acid. Exemplary NMPRT inhibitors include a Pyridyl Cyanoguanidine or a Prodrug Thereof and (E)-N-[4-(1-benzoylpiperidin-4-yl)butyl]-3-(pyridin-3-yl)acrylamide. Other NMPRT inhibitors can also be used in the compositions and methods of the invention.

Compositions comprising a NMPRT inhibitor and nicotinic acid are suitable for internal or external use and comprise a physiologically acceptable carrier or vehicle, an effective amount of a NMPRT inhibitor and an effective amount of nicotinic acid.

A NMPRT inhibitor and nicotinic acid can be administered in amounts that are effective for decreasing cellular DNA repair in a target cell, decreasing cellular NAD+ biosynthesis in a target cell, increasing efficiency of radiation therapy in a target cell, modulating nicotinamide phosphoribosyl transferase activity in a cell, decreasing cellular DNA repair in a target patient, decreasing cellular NAD+ biosynthesis in a target patient, increasing efficiency of radiation therapy in a target patient, modulating nicotinamide phosphoribosyl transferase activity in a patient, sensitizing a patient to a DNA damaging therapy, or treating a patient diagnosed with or suspected to have a cancer deficient in nicotinic acid pathway.

Administration of a NMPRT inhibitor and nicotinic acid can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, compositions comprising an effective amount of a NMPRT inhibitor and nicotinic acid can be in solid, semi-solid or liquid dosage form, such as, for example, injectables, tablets, suppositories, pills, time-release capsules, elixirs, tinctures, emulsions, syrups, powders, liquids, suspensions, or the like, in one embodiment, in unit dosages and consistent with conventional pharmaceutical practices. Likewise, the compositions can also be administered in intravenous (both bolus and infusion), intraperitoneal, subcutaneous or intramuscular form, all using other forms known to those skilled in the art.

Illustrative pharmaceutical compositions include tablets and gelatin capsules. Illustrative (physiologically acceptable) carriers or vehicles include, but are not limited to: a) a diluent, e.g., lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algiic acid or its sodium salt, or effervescent mixtures; and/or e) absorbent, colorant, flavorant and sweetener.

Liquid, particularly injectable, compositions can, for example, be prepared by dissolution or dispersion. For example, a NMPRT inhibitor and nicotinic acid are admixed with a pharmaceutically acceptable solvent such as, for example, water, saline, aqueous dextrose, glycerol, ethanol, and the like, to thereby form an injectable isotonic solution or suspension.

A NMPRT inhibitor and nicotinic acid can be also formulated as a suppository that can be prepared from fatty emulsions or suspensions, using polyalkylene glycols such as propylene glycol, as the carrier.

A NMPRT inhibitor and nicotinic acid can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564, which is incorporated herein by reference.

A NMPRT inhibitor and nicotinic acid can also be delivered by the use of monoclonal antibodies as individual carriers to which the NMPRT inhibitor and/or nicotinic acid is coupled. The NMPRT inhibitor and/or nicotinic acid can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxide-polylysine substituted with palmitoyl residues. Furthermore, the NMPRT inhibitor and/or nicotinic acid can be coupled to a class of biodegradable polymers useful in achieving controlled release of a drug, for example, polylactic acid, poly-epsilon caprolactone, polyhydroxy butyric acid, polyorthoesters, polyacetals, polydihydropyrans, polycyanoacrylates and cross-linked or amphipathic block copolymers of hydrogels.

Parenteral injectable administration can be used for subcutaneous, intramuscular or intravenous injections and infusions. Injectables can be prepared in conventional forms, either as liquid solutions or suspensions or solid forms suitable for dissolving in liquid prior to injection.

In one embodiment, the NMPRT inhibitor and nicotinic acid are administered intravenously. In another embodiment, the NMPRT inhibitor is administered intravenously and nicotinic acid is administered orally. In yet another embodiment, the NMPRT inhibitor and nicotinic acid are both administered orally.

One embodiment, for parenteral administration employs the implantation of a slow-release or sustained-released system, according to U.S. Pat. No. 3,710,795, which is incorporated herein by reference.

The compositions can be sterilized or can contain non-toxic amounts of adjuvants, such as preserving, stabilizing, wetting or emulsifying agents, solution promoters, salts for regulating the osmotic pressure pH buffering agents, and other substances, including, but not limited to, sodium acetate or triethanolamine oleate. In addition, the compositions can also contain other therapeutically useful substances.

Compositions can be prepared according to conventional mixing, granulating or coating methods, respectively, and the present pharmaceutical compositions can contain from about 0.1% to about 99%, or from about 1% to about 70% of the NMPRT inhibitor by weight or volume.

The dosage regimen for utilizing the NMPRT inhibitor and nicotinic acid when administered intravenously can be selected in accordance with a variety of factors including type, species, age, weight, sex and medical condition of the patient; the severity of the condition that the patient in need of treatment with a NMPRT inhibitor and nicotinic acid, or a cell, is in; the route of administration; the renal or hepatic function of the patient; and the particular NMPRT inhibitor employed. A person skilled in the art can readily determine or prescribe the effective amount of the NMPRT inhibitor and nicotinic acid that when administered intravenously useful for achieving the desired effect in a cell or in a patient in need of treatment with a NMPRT inhibitor and nicotinic acid.

Effective dosage amounts of a NMPRT inhibitor and nicotinic acid, when administered to a patient, range from about 0.05 to about 1000 mg of the NMPRT inhibitor per day. Compositions for in vivo or in vitro use can contain about 0.5, 1.0, 2.5, 5.0, 10.0, 15.0, 25.0, 50.0, 100.0, 250.0, 500.0 or 1000.0 mg of NMPRT inhibitor. In one embodiment, the compositions are in the form of a tablet that can be scored. Effective plasma levels of the NMPRT inhibitor can range from about 0.1 to 2.0 µg/mL. The amount of a NMPRT inhibitor that is effective for achieving the desired effect in a cell or in a patient in need of such treatment can be determined using clinical techniques that are known to those of skill in the art. In addition, in vitro and in vivo assays can optionally be employed to help identify optimal dosage ranges. The precise dose to be employed can also depend on the route of administration, and the seriousness of the condition of a cell or a patient in need of such treatment and can be decided according to the judgment of the practitioner and each patient's circumstances in view of, e.g., published clinical studies. Suitable effective dosage amounts, however, can range from about 10 micrograms to about 5 grams about every 4 hours, in one embodiment, about 500 mg or less per every 4 hours. In one embodiment, the effective dosage is about 0.01 mg, 0.5 mg, about 1 mg, about 50 mg, about 100 mg, about 200 mg, about 300 mg, about 400 mg, about 500 mg, about 600 mg, about 700 mg, about 800 mg, about 900 mg, about 1 g, about 1.2 g, about 1.4 g, about 1.6 g, about 1.8 g, about 2.0 g, about 2.2 g, about 2.4 g, about 2.6 g, about 2.8 g, about 3.0 g, about 3.2 g, about 3.4 g, about 3.6 g, about 3.8 g, about 4.0 g, about 4.2 g, about 4.4 g, about 4.6 g, about 4.8 g, and about 5.0 g, every 4 hours. Equivalent dosages can be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The effective dosage amounts described herein refer to total amounts administered; that is, if more than one NMPRT inhibitor is administered, the effective dosage amounts correspond to the total amount administered.

A NMPRT inhibitor and nicotinic acid can be administered in a single daily dose, or the total daily dosage can be administered in divided doses of two, three or four times daily. Furthermore, a NMPRT inhibitor and nicotinic acid can be administered in intranasal form via topical use of suitable intranasal vehicles, or via transdermal routes, using those forms of transdermal skin patches known to those of skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of a NMPRT inhibitor and nicotinic acid ranges from about 0.1% to about 15%, weight/weight or weight/volume.

In one embodiment, the compositions comprise a total amount of a NMPRT inhibitor and nicotinic acid that is effective on its own. In another embodiment, the amount of NMPRT inhibitor and nicotinic acid is at least about 0.01% of the combined combination chemotherapy agents by weight of the composition. When intended for oral administration, this amount can be varied from about 0.1% to about 80% by weight of the composition. Some oral compositions can comprise from about 4% to about 50% of a NMPRT inhibitor and nicotinic acid. Other compositions of the present invention are prepared so that a parenteral dosage unit contains from about 0.01% to about 2% by weight of the composition.

The NMPRT inhibitor and nicotinic acid can be assayed in vitro or in vivo for the desired therapeutic or prophylactic activity prior to use in humans. Animal model systems can be used to demonstrate safety and efficacy.

The present methods for using a NMPRT inhibitor and nicotinic acid can further comprise administering another prophylactic or therapeutic agent to the patient being administered a NMPRT inhibitor and nicotinic acid. In one embodiment, the other prophylactic or therapeutic agent is administered in an effective amount. The other prophylactic or therapeutic agent includes, but is not limited to, an antiemetic agent, a hematopoietic colony stimulating factor, an anxiolytic agent, and an analgesic agent.

In a further embodiment, the NMPRT inhibitor and nicotinic acid can be administered prior to, concurrently with, or after the other prophylactic or therapeutic agent, or on the same day, or within 1 hour, 2 hours, 12 hours, 24 hours, 48 hours or 72 hours of each other.

Effective amounts of the prophylactic or therapeutic agents are known to those skilled in the art. However, it is well within the skilled artisan's purview to determine the other prophylactic or therapeutic agent's optimal effective amount range.

In one embodiment, the other prophylactic or therapeutic agent is an antiemetic agent. Antiemetic agents useful in the methods of the present invention include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine and tropisetron.

In one embodiment, the other prophylactic or therapeutic agent is a hematopoietic colony stimulating factor. Hematopoietic colony stimulating factors useful in the methods of the present invention include, but are not limited to, filgrastim, sargramostim, molgramostim and epoietin alfa.

In one embodiment, the other prophylactic or therapeutic agent is an opioid analgesic agent. Opioid analgesic agents useful in the methods of the present invention include, but are not limited to, morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene.

In one embodiment, the other prophylactic or therapeutic agent is a non-opioid analgesic agent. Non-opioid analgesic agents useful in the methods of the present invention include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam and sulindac.

In one embodiment, the other prophylactic or therapeutic agent is an anxiolytic agent. Anxiolytic agents useful in the methods of the present invention include, but are not limited to, buspirone, and benzodiazepines such as diazepam, lorazepam, oxazapam, chlorazepate, clonazepam, chlordiazepoxide and alprazolam.

The compositions of the invention can be sold or used as prescription products, or alternatively as over-the-counter products. In one embodiment, the compositions of the invention can be sold or used as nutraceutical products.

6.15 Pharmaceutical Compositions Comprising a NMPRT Inhibitor, Nicotinic Acid, and a DNA Damaging Chemotherapeutic Agent In some embodiments, the invention provides a pharmaceutical composition useful for treating a patient diagnosed with or suspected to have a cancer deficient in nicotinic acid pathway. In some embodiments, the pharmaceutical compositions comprise a physiologically acceptable carrier, an effective amount of a NMPRT inhibitor, an effective amount of nicotinic acid, and an effective amount of a DNA damaging chemotherapeutic agent.

In one embodiment, the NMPRT inhibitor is a Pyridyl Cyanoguanidine or a Prodrug Thereof. In another embodiment, the NMPRT inhibitor is (E)-N-[4-(1-benzoylpiperidin-4-yl)butyl]-3-(pyridin-3-yl)acrylamide. Other NMPRT inhibitors can also be used in the compositions of the invention.

Suitable DNA damaging chemotherapeutic agents include, but are not limited to: Cladribine, Pentostatin, Methotrexate, Trimetrexate glucuronate, Pemetrexed, Treosulfan, Busulfan, Dacarbazine, Temozolomide, Mitomycin C, Chlorambucil, Ifosfamide, Melphalan, Thiotepa, Mechlorethamine, Carmustine, Bendamustin, Fotemustine, Lomustine, Streptozocin, Carboplatin, Cisplatin, Lobaplatin, Oxaliplatin Bleomycin, Hydroxyurea, Actinomycin D, Azacitidine, Decitabine, Nelarabine, Cytarabine, Fludarabine, Clofarabine, Vorinostat, Gemcitabine, 5-Fluorouracil, Capecitabine, Floxuridine, Raltitrexed, Pemetrexed, Irinotecan, Topotecan, Amrubicin, Daunorubicin, Doxorubicin, Epirubicin, Etoposide, Idarubicin, Mitoxantrone, Teniposide, Valrubicin, Allopurinol, or a pharmaceutically acceptable salt thereof.

Compositions comprising a NMPRT inhibitor, nicotinic acid, and a DNA damaging chemotherapeutic agent are suitable for internal or external use and comprise a physiologically acceptable carrier or vehicle, an effective amount of a NMPRT inhibitor, an effective amount of nicotinic acid, and an effective amount of a DNA damaging chemotherapeutic agent.

A NMPRT inhibitor, nicotinic acid and a DNA damaging chemotherapeutic agent can be administered in amounts that are effective for treating a patient diagnosed with or suspected to have a cancer deficient in nicotinic acid pathway.

Administration of a NMPRT inhibitor, nicotinic acid and a DNA damaging chemotherapeutic agent can be accomplished via any mode of administration for therapeutic agents. These modes include systemic or local administration such as oral, nasal, parenteral, transdermal, subcutaneous, vaginal, buccal, rectal or topical administration modes. In one embodiment, the NMPRT inhibitor, nicotinic acid and a DNA damaging chemotherapeutic agent are suitable for oral administration. In another embodiment, the NMPRT inhibitor, nicotinic acid and a DNA damaging chemotherapeutic agent are suitable for parenteral administration.

Depending on the intended mode of administration, compositions comprising an effective amount of a NMPRT inhibitor, nicotinic acid and a DNA damaging chemotherapeutic agent can be in solid, semi-solid or liquid dosage form, such as, for example, injectables, tablets, suppositories, pills, time-release capsules, elixirs, tinctures, emulsions, syrups, powders, liquids, suspensions, or the like, in one embodiment, in unit dosages and consistent with conventional pharmaceutical practices. Likewise, the compositions can also be administered in intravenous (both bolus and infusion), intraperitoneal, subcutaneous or intramuscular form, all using other forms known to those skilled in the art.

Illustrative pharmaceutical compositions include tablets and gelatin capsules. Illustrative (physiologically acceptable) carriers or vehicles include, but are not limited to: a) a diluent, e.g., lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algiic acid or its sodium salt, or effervescent mixtures; and/or e) absorbent, colorant, flavorant and sweetener.

Liquid, particularly injectable, compositions can, for example, be prepared by dissolution or dispersion. For example, a NMPRT inhibitor, nicotinic acid, and a DNA damaging chemotherapeutic agent can be admixed with a pharmaceutically acceptable solvent such as, for example, water, saline, aqueous dextrose, glycerol, ethanol, and the like, to thereby form an injectable isotonic solution or suspension.

A NMPRT inhibitor, nicotinic acid, and a DNA damaging chemotherapeutic agent can be also formulated as a suppository that can be prepared from fatty emulsions or suspensions, using polyalkylene glycols such as propylene glycol, as the carrier.

A NMPRT inhibitor, nicotinic acid, and a DNA damaging chemotherapeutic agent can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564, which is incorporated herein by reference.

A NMPRT inhibitor, nicotinic acid, and a DNA damaging chemotherapeutic agent can also be delivered by the use of monoclonal antibodies as individual carriers to which the NMPRT inhibitor and/or nicotinic acid and/or the DNA damaging chemotherapeutic agent is coupled. The NMPRT inhibitor, nicotinic acid, and a DNA damaging chemotherapeutic agent can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the NMPRT inhibitor, nicotinic acid and/or the DNA damaging chemotherapeutic agent can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Parenteral injectable administration can be used for subcutaneous, intramuscular or intravenous injections and infusions. Injectables can be prepared in conventional forms, either as liquid solutions or suspensions or solid forms suitable for dissolving in liquid prior to injection.

In one embodiment, the NMPRT inhibitor and nicotinic acid are administered intravenously. In another embodiment, the NMPRT inhibitor is administered intravenously and nicotinic acid is administered orally. In yet another embodiment, the NMPRT inhibitor and nicotinic acid are administered orally.

One embodiment, for parenteral administration employs the implantation of a slow-release or sustained-released system, according to U.S. Pat. No. 3,710,795, which is incorporated herein by reference.

The compositions can be sterilized or can contain non-toxic amounts of adjuvants, such as preserving, stabilizing, wetting or emulsifying agents, solution promoters, salts for regulating the osmotic pressure pH buffering agents, and other substances, including, but not limited to, sodium acetate or triethanolamine oleate. In addition, the compositions can also contain other therapeutically useful substances.

Compositions can be prepared according to conventional mixing, granulating or coating methods, respectively, and the present pharmaceutical compositions can contain from about 0.1% to about 99%, preferably from about 1% to about 70% of the NMPRT inhibitor by weight or volume.

The dosage regimen utilizing the NMPRT inhibitor, nicotinic acid, and the DNA damaging chemotherapeutic agent administered intravenously can be selected in accordance with a variety of factors including type, species, age, weight, sex and medical condition of the patient; the severity of the condition of the patient in need of treatment with the NMPRT inhibitor, nicotinic acid, and the DNA damaging chemotherapeutic agent; the route of administration; the renal or hepatic function of the patient; and the particular NMPRT inhibitor and the particular DNA damaging chemotherapeutic agent employed. A person skilled in the art can readily determine or prescribe the effective amount of the NMPRT inhibitor, nicotinic acid, and the DNA damaging chemotherapeutic agent that when administered intravenously are useful for achieving the desired effect in a cell or in a patient in need of treatment with the NMPRT inhibitor, nicotinic acid, and the DNA damaging chemotherapeutic agent.

Effective dosage amounts of a NMPRT inhibitor, nicotinic acid, and a DNA damaging chemotherapeutic agent, when administered to a patient, range from about 0.05 to about 1000 mg of the NMPRT inhibitor or a prodrug thereof per day. Compositions for in vivo or in vitro use can contain about 0.5, 1.0, 2.5, 5.0, 10.0, 15.0, 25.0, 50.0, 100.0, 250.0, 500.0 or 1000.0 mg of NMPRT inhibitor. In one embodiment, the compositions are in the form of a tablet that can be scored. Effective plasma levels of the NMPRT inhibitor can range from about 0.1 to 2.0 μg/mL. The amount of a NMPRT inhibitor that is effective for achieving the desired effect in a cell or in a patient in need of such treatment can be determined using clinical techniques that are known to those of skill in the art. In addition, in vitro and in vivo assays can optionally be employed to help identify optimal dosage ranges. The precise dose to be employed can also depend on the route of administration, and the seriousness of the condition of a cell or a patient in need of such treatment and can be decided according to the judgment of the practitioner and each patient's circumstances in view of, e.g., published clinical studies. Suitable effective dosage amounts, however, can range from about 10 micrograms to about 5 grams about every 4 hours, in one embodiment, about 500 mg or less per every 4 hours. In one embodiment, the effective dosage is about 0.01 mg, 0.5 mg, about 1 mg, about 50 mg, about 100 mg, about 200 mg, about 300 mg, about 400 mg, about 500 mg, about 600 mg, about 700 mg, about 800 mg, about 900 mg, about 1 g, about 1.2 g, about 1.4 g, about 1.6 g, about 1.8 g, about 2.0 g, about 2.2 g, about 2.4 g, about 2.6 g, about 2.8 g, about 3.0 g, about 3.2 g, about 3.4 g, about 3.6 g, about 3.8 g, about 4.0 g, about 4.2 g, about 4.4 g, about 4.6 g, about 4.8 g, and about 5.0 g, every 4 hours. Equivalent dosages can be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The effective dosage amounts described herein refer to total amounts administered; that is, if more than one NMPRT inhibitor is administered, the effective dosage amounts correspond to the total amount administered.

A NMPRT inhibitor, nicotinic acid, and a DNA damaging chemotherapeutic agent can be administered in a single daily dose, or the total daily dosage can be administered in divided doses of two, three or four times daily. Furthermore, a NMPRT inhibitor, nicotinic acid, and a DNA damaging chemotherapeutic agent can be administered in intranasal form via topical use of suitable intranasal vehicles, or via transdermal routes, using those forms of transdermal skin patches known to those of skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of a NMPRT inhibitor, nicotinic acid, and a DNA damaging chemotherapeutic agent ranges from about 0.1% to about 15%, weight/weight or weight/volume.

In one embodiment, the compositions comprise a total amount of a NMPRT inhibitor, nicotinic acid, and a DNA damaging chemotherapeutic agent that is effective on its own. In another embodiment, the amount of NMPRT inhibitor, nicotinic acid, and a DNA damaging chemotherapeutic agent is at least about 0.01% of the combined combination chemotherapy agents by weight of the composition. When intended for oral administration, this amount can be varied from about 0.1% to about 80% by weight of the composition. Some oral compositions can comprise from about 4% to about 50% of a NMPRT inhibitor, nicotinic acid, and a DNA damaging chemotherapeutic agent. Other compositions of the present invention are prepared so that a parenteral dosage unit contains from about 0.01% to about 2% by weight of the composition.

The NMPRT inhibitor, nicotinic acid, and a DNA damaging chemotherapeutic agent can be assayed in vitro or in vivo for the desired therapeutic or prophylactic activity prior to use in humans. Animal model systems can be used to demonstrate safety and efficacy.

The present methods for using a NMPRT inhibitor, nicotinic acid, and a DNA damaging chemotherapeutic agent can further comprise administering another prophylactic or therapeutic agent to the patient being administered a NMPRT inhibitor, nicotinic acid, and a DNA damaging chemotherapeutic agent. In one embodiment, the other prophylactic or therapeutic agent is administered in an effective amount. The other prophylactic or therapeutic agent includes, but is not limited to, an antiemetic agent, a hematopoietic colony stimulating factor, an anxiolytic agent, and an analgesic agent.

In a further embodiment, the NMPRT inhibitor, nicotinic acid, and the DNA damaging chemotherapeutic agent can be administered prior to, concurrently with, or after the other prophylactic or therapeutic agent, or on the same day, or within 1 hour, 2 hours, 12 hours, 24 hours, 48 hours or 72 hours of each other.

Effective amounts of the prophylactic or therapeutic agents are known to those skilled in the art. However, it is well within the skilled artisan's purview to determine the other prophylactic or therapeutic agent's optimal effective amount range.

In one embodiment, the other prophylactic or therapeutic agent is an antiemetic agent. Antiemetic agents useful in the methods of the present invention include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine and tropisetron.

In one embodiment, the other prophylactic or therapeutic agent is a hematopoietic colony stimulating factor. Hematopoietic colony stimulating factors useful in the methods of the present invention include, but are not limited to, filgrastim, sargramostim, molgramostim and epoietin alfa.

In one embodiment, the other prophylactic or therapeutic agent is an opioid analgesic agent. Opioid analgesic agents useful in the methods of the present invention include, but are not limited to, morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene.

In one embodiment, the other prophylactic or therapeutic agent is a non-opioid analgesic agent. Non-opioid analgesic agents useful in the methods of the present invention include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam and sulindac.

In one embodiment, the other prophylactic or therapeutic agent is an anxiolytic agent. Anxiolytic agents useful in the methods of the present invention include, but are not limited to, buspirone, and benzodiazepines such as diazepam, lorazepam, oxazapam, chlorazepate, clonazepam, chlordiazepoxide and alprazolam.

The compositions of the invention can be sold or used as prescription products, or alternatively as over-the-counter products. In one embodiment, the compositions of the invention can be sold or used as nutraceutical products.

6.16 Methods for Treating a Patient Diagnosed with or Suspected to have a Cancer Deficient in Nicotinic Acid Pathway The combination of a NMPRT inhibitor and nicotinic acid is useful for treating a patient diagnosed with or suspected to have chronic lymphocytic leukemia ("CLL"), a cancer deficient in nicotinic acid pathway. In some embodiments, the NMPRT inhibitor is a Pyridyl Cyanoguanidine or a Prodrug Thereof. In another embodiment, the NMPRT inhibitor is (E)-N-[4-(1-benzoylpiperidin-4-yl)butyl]-3-(pyridin-3-yl) acrylamide.

An inhibitor of NMPRT can be more toxic to cancer cells than normal (healthy) cells. However, administration of a NMPRT inhibitor can lead to a harmful and even lethal $NAD^+$ depletion even in normal cell. Because $NAD^+$ can be synthesized independently via nicotinic acid pathway from nicotinic acid, administration of nicotinic acid can replenish $NAD^+$ in normal cells and reduce side effects associated with the administration of the NMPRT inhibitor. Thus, nicotinic acid is useful for treating a patient being treated with a NMPRT inhibitor. In some embodiments, the NMPRT inhibitor is a Pyridyl Cyanoguanidine or a Prodrug Thereof. In another embodiment, the NMPRT inhibitor is (E)-N-[4-(1-benzoylpiperidin-4-yl)butyl]-3-(pyridin-3-yl)acrylamide.

In cancers that are deficient in nicotinic acid pathway, administration of nicotinic acid will not replenish $NAD^+$ and thereby not reduce the toxicity of the NMPRT inhibitor to the cancer cell. Thus, the efficacy of the NMPRT inhibitor in cancer cells deficient in nicotinic acid pathway will not be reduced by administration of nicotinic acid. In contrast, administration of nicotinic acid to normal cells (which can synthesize $NAD^+$ using the nicotinic acid pathway), reduces toxicity and side effects associated with administration of the NMPRT inhibitor to normal cells or uptake of the NMPRT inhibitor by normal cells. Therefore, a higher dose of the NMPRT inhibitor can be administered to the patient diagnosed with or suspected to have a cancer deficient in nicotinic acid when co-administered with nicotinic acid. Side effects in a patient administered the NMPRT inhibitor can also be reduced by co-administration of nicotinic acid. By co-administration of a NMPRT inhibitor and nicotinic acid, it is meant that the NMPRT inhibitor is administered prior to or subsequent to nicotinic acid, or that the NMPRT inhibitor and nicotinic acid are administered concurrently.

The invention provides methods for treating a patient (e.g., a human) diagnosed with or suspected to have chronic lymphocytic leukemia, which is a cancer deficient in nicotinic acid pathway comprising administering to the patient in need thereof an effective amount of a NMPRT inhibitor and an effective amount of nicotinic acid.

In one embodiment, nicotinic acid is administered as an intravenous infusion at a dose of 2.8 mg/min for 1 h (90 $mg/m^2$ total). In another embodiment, nicotinic acid is administered as an intravenous infusion at a dose of 2.8 mg/min for 2 h (180 $mg/m^2$ total). In yet another embodiment, nicotinic acid is administered as an intravenous infusion at a dose of 2.8 mg/min for 3 h (270 $mg/m^2$ total). In still another embodiment, nicotinic acid is administered as an intravenous infusion at a dose of 2.8 mg/min for 4 h (90 $mg/m^2/h$; 360 $mg/m^2$ total). In a specific embodiment, administering the effective amount of nicotinic acid comprises intravenously administering nicotinic acid at to the patient at dose of about 90 $mg/m^2/h$ for at least four hours.

In some embodiments, the effective amount of nicotinic acid is administered orally, for example, using a capsule or a tablet. Of course, any formulation suitable for oral administration can be used to deliver the effective amount of nicotinic acid to the patient.

6.17 Identification of Cancers Deficient in Nicotinic Acid Pathway

It has been discovered that some cancers, but not all, are deficient in nicotinic acid pathway. One method that is useful for determination whether a cancer is deficient in nicotinic acid pathway is to add isotopically labeled nicotinic acid (e.g., with $^2H$, $^3H$, $^{13}C$, $^{14}C$, $^{15}N$, $^{17}O$, or $^{18}O$) to the tissue culture and monitor cellular production of isotopically labeled $NAD^+$ in the tissue (see Hara et al. (2007), "Elevation of cellular NAD levels by nicotinic acid and involvement of nicotinic acid phosphoribosyltransferase in human cells", *Journal of Biological Chemistry* 282 (34): 24574-24582, incorporated by reference herein in its entirety). Another method that is useful for determination whether a cancer is deficient in nicotinic acid pathway is to administer an effective dose of a NMPRT inhibitor to cells or a patient followed by administration of nicotinic acid. If the cancer is deficient in nicotinic acid pathway, the cells or the patient will be rescued (i.e., the survival rate will increase). Another method is to determine NAPRT1 expression by immunohistochemical screening of tissue samples. Tissue sections were scored for specific NAPRT1 expression by comparison of sections stained with anti-NAPRT1 compared to sequential sections stained with a pre-immune rabbit IgG to assess non-specific staining. Of course, other methods for determination whether a cancer is deficient in nicotinic acid pathway can also be used. A more detailed explanation is provided in the Examples section, below.

Exemplary cancers deficient in nicotinic acid pathway include, but are not limited to, sarcomas, glioblastoma, neuroblastoma, colon cancer, and chronic lymphocytic leukemia.

6.18 Kits Comprising a NMPRT Inhibitor and Nicotinic Acid

The invention encompasses kits that can simplify the administration of a NMPRT inhibitor and nicotinic acid to a patient. In some embodiments, the NMPRT inhibitor is a Pyridyl Cyanoguanidine or a Prodrug Thereof. In another embodiment, the NMPRT inhibitor is (E)-N-[4-(1-benzoylpiperidin-4-yl)butyl]-3-(pyridin-3-yl)acrylamide.

In one aspect, a kit of the invention comprises a unit dosage form of a NMPRT inhibitor and nicotinic acid. In another aspect, the kit comprises a unit dosage form of a NMPRT inhibitor and a unit dosage form of nicotinic acid. In one embodiment, the unit dosage form is a container, which can be sterile, containing an effective amount of a NMPRT inhibitor and/or an effective amount of nicotinic acid and a physiologically acceptable carrier or vehicle. The kit can further comprise a label or printed instructions instructing the use of the NMPRT inhibitor and nicotinic acid to achieve the desired effect in a patient in need of such treatment.

The kit can also further comprise a unit dosage form of another prophylactic or therapeutic agent, for example, a container containing an effective amount of the other prophylactic or therapeutic agent. In one embodiment, the kit comprises a container containing an effective amount of a NMPRT inhibitor and nicotinic acid and an effective amount of another prophylactic or therapeutic agent. Examples of other therapeutic agents include, but are not limited to, those listed above.

In another embodiment, the kit of the invention comprises a unit dosage form of a NMPRT inhibitor (e.g., a Pyridyl Cyanoguanidine or a Prodrug Thereof), nicotinic acid, and a DNA damaging chemotherapeutic agent. In one embodiment, the unit dosage form is a container, which can be sterile, containing an effective amount of a NMPRT inhibitor, an effective amount of nicotinic acid, an effective amount of a DNA damaging chemotherapeutic agent, and a physiologically acceptable carrier or vehicle.

The kit can further comprise a label or printed instructions instructing the use of the NMPRT inhibitor, nicotinic acid, and a DNA damaging chemotherapeutic agent to achieve the desired effect in a patient in need of such treatment.

In one embodiment, the kit comprises a container containing an effective amount of a NMPRT inhibitor, nicotinic acid, a DNA damaging chemotherapeutic agent and an effective amount of another prophylactic or therapeutic agent. Examples of other therapeutic agents include, but are not limited to, those listed above.

A kit of the invention can further comprise a device that is useful for administering the unit dosage forms. Examples of such a device include, but are not limited to, a syringe, a drip bag, a patch, an inhaler, and an enema bag.

The invention is further described in the following examples, which do not limit the scope of the invention described in the claims. The following examples illustrate the uses of NMPRT inhibitors, Pyridyl Cyanoguanidines and prodrugs thereof, nicotinic acid, and DNA damaging therapy for achieving the desired effect in a cell or a patient in need of treatment.

7. EXAMPLES

7.1 General Experimental Methods

7.1.1 Cell Culture and Test Compounds

Cell lines used in this study corresponding to those of the NCI panel of 60 were: CCRF-CEM, HL-60, K-562, MOLT-4, RPMI-8226, A549, NCI-H226, NCI-H460, HCT-116, HT29, SW-620, U251, MALME-3M, SK-MEL-2, SK-MEL-28, SK-MEL-5, SK-OV-3, A498, CAKI-1, PC-3, DU-145, MCF7, NCI/ADR-RES, MDA-MB-231, BT-549. NCI-ADR-RES and U-251 cells were obtained from the National Cancer Institute (NCI; Frederick, Md.), NYH from Leo Pharmaceuticals (Ballerup, Denmark) all other cell lines including IM-9, DMS-114, SHP-77 and HeLa were obtained from the ATCC (Manassas, Va.) and were maintained in culture in Roswell Park Memorial Institute (RPMI) 1640 media (Hyclone; Logan, Utah) supplemented with 10% FBS (Hyclone, Logan, Utah), Penicillin (100 U/mL), Streptomycin (100 µg/mL), and 2 mM L-glutamine (Invitrogen; Carlsbad, Calif.). MCF-7 cells were also supplemented with 10 µg/mL of insulin (Sigma-Aldrich; St. Louis, Mo.). Stock solutions of Compound 1 were made up at stock concentrations of 15 mM from powder in dimethyl sulfoxide (DMSO, Sigma-Aldrich; St. Louis, Mo.) and stored at −20° C. Nicotinic acid and nicotinamide (Sigma-Aldrich; St. Louis, Mo.) were made up in RPMI-1640 as 100 mM stock solutions and then filter sterilized before use. Doxorubicin (Sigma-Aldrich; St. Louis, Mo.) was made up as a stock solution of 10 mM in DMSO.

SW982, Jurkat, MES-SA, U-2OS, HT1080 and Hs821.T cells were obtained from American Type Culture Collection (Manassas, Va.) and cultured in RPMI. 4-hydroxy-cyclophosphamide, temozolomide, carmustine, and streptozotocin were obtained from Sigma-Aldrich (St. Louis, Mo.). 4-hydroxy-cyclophosphamide, temozolomide, and streptozotocin were made up as stock solutions in DMSO. Carmustine was made up as a stock solution in ethanol.

7.1.2 Biochemical Pathway Profiling Studies

IM-9 cells were treated with 0.2% DMSO (control samples) or Compound 1 at 30 nM (6 replicates of each). At 6 hours after Compound 1 treatment, $2 \times 10^6$ viable (as determined by trypan blue staining) cells were harvested from each sample, rinsed three times in cold PBS and the cell pellets snap frozen in liquid nitrogen. Cell pellets were frozen at −80° C., thawed, and extracted using the automated MicroLab STAR® system (Hamilton Company, Salt Lake City, Utah). Resulting extracts were divided into 2 fractions; one for Liquid Chromatography and one for Gas Chromatography.

7.1.3 Liquid Chromatography/Mass Spectroscopy (LC/MS)

LC/MS was carried out using a Surveyor HPLC with an electrospray ionization source coupled to an LTQ mass spectrometer (ThermoElectron Corporation; Waltham Mass.). Cell extracts were loaded onto an Aquasil column (Thermo-Electron Corporation; Waltham Mass.) via a CTC autosampler (LeapTechnologies; Carrboro, N.C.) and gradient eluted (0% B, 4 min; 0-50% B, 2 min; 50-80% B, 5 min, 80-100% B, 1 minute; maintain 100% B, 2 minutes; (Solvent A: 0.1% formic Acid in $H_2O$); Solvent B: 0.1% formic acid in MeOH) directly into the mass spectrometer (flow rate of 200 µL/min). The LTQ took full scan mass spectra while switching polarity to monitor negative and positive ions. An LTQ-FTICR hybrid MS (ThermoElectron Corporation; Waltham, Mass.) operated at 50,000 resolving power with a mass measurement error<10 ppm using gradient conditions described above was used to confirm reported biochemicals present above the instrument's LOD.

7.1.4 Gas Chromatography/Mass Spectroscopy (GC/MS).

Samples destined for GC/MS analysis were re-dried under vacuum desiccation for a minimum of 24 h prior to being derivatized under dried nitrogen using equal parts of bistrimethyl-silyl-trifluoroacetamide (BSTFA) and solvent mixture (ACN:DCM:cyclohexane (5:4:1, v/v/v) with 5% TEA) containing standards, and placed at 60° C. for 1 h. The GC column was 5% phenyl, and the temperature ramp was 40-300° C. in 16 min. Samples were analyzed on a Thermo-Finnigan Trace DSQ fast-scanning single-quadrupole mass spectrometer (ThermoElectron Corporation; Waltham Mass.) using EI ionization with 50-750 amu scan range and tuned and calibrated daily for mass resolution and mass accuracy.

7.1.5 Statistical Analyses

Statistical analysis of the data was performed using JMP (SAS, http://www.jmp.com), a commercial software package, and "R" (http://cran.r-project.org/). A logarithmic (ln) transform was applied to the observed relative concentrations for each biochemical. Biochemicals with detectable levels in at least two-thirds of the samples in any groups, were included in the analyses. Biochemicals considered to be significantly changed relative to time-matched control samples had a q-value$\leq$0.2 and a p-value$\leq$0.1.

7.1.6 Relative ATP Levels (Viability Assays)

Cells were plated in logarithmic growth phase at 500-20,000 cells per well in 96-well clear bottom plates (Corning; Corning, N.Y.) and cultured for 14 to 16 hours prior to the start of drug treatment. Serial dilutions of Compound 2 and Compound 1 were made in DMSO, diluted 1:50 in RPMI-1640 (Hyclone; Logan, Utah) and then added to tissue culture media at a final concentration of 0.2% DMSO. Cells were typically treated with a dose range of compound from approximately 250 nM in 1:3 dilutions to 3.8 pM for 72 hours unless otherwise indicated. Relative ATP levels were determined by the bioluminescent measuring of cellular ATP levels in each culture well with the ViaLight-HS High Sensitivity Cytotoxicity and Cell Proliferation BioAssay Kit (Cambrex Bioproducts, Cat. No. LT07-311; Charles City, Iowa) according to manufacturer's instructions. Briefly, a cell permeabilizing reagent was added to each culture well in media at the time of viability determination, allowing free ATP to be released from viable cells in the culture. Addition of luciferase to the mixture catalyzes the release of light proportional to the amount of free ATP present, which can then be quantified in a Centro LB 960 luminometer (EG&G Berthold; Oak Ridge, Tenn.); the level of ATP is generally directly proportional to the viability of the cells.

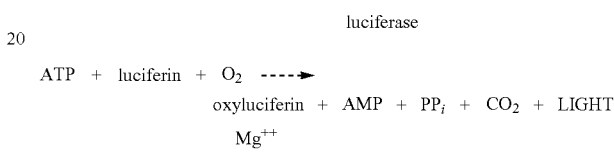

To calculate the relative ATP levels, the mean value of relative light units (RLU) from triplicate samples in the ViaLight assay at each dose was divided by the mean value (×100) obtained from DMSO treated cells to give percent change in ATP levels or percent viability. Sigmoidal dose response curves were then generated using non-linear regression analysis of variable slope by Prism Version 4.00 for Windows (GraphPad Software, Inc.; San Diego, Calif.) and $IC_{50}$ values calculated.

7.1.7 Cell Lysis

An aliquot of 300 µL of IM-9 cells ($10^5$ cells/ml) in media was removed at various times after 30 nM Compound 1 treatment, diluted 1:3 in PBS containing 50 ng/mL of PI and then analyzed by flow cytometry within 1 hour on a BD FACSCalibur flow cytometer (BD Biosciences; Mississauga, ON, Canada). Data from 10,000 cells was collected from one cell sample at each time point.

7.1.8 Determination of Intracellular $NAD^+$ Levels

HeLa cells (1×$10^6$ cells in duplicate) were treated with DMSO or Compound 1 (100 nM) in the presence or absence of nicotinic acid (10 µM) for 18 hrs. Cells were harvested by trypsinization and centrifugation, and cell pellets were snap frozen in liquid nitrogen and stored at −80° C. before being extracted. The pellets were resuspended in 500 µL of water containing 2-chloroadenosine (Sigma-Aldrich; St. Louis, Mo.) as internal standard followed by the addition of 500 µL of perchloric acid (1M). After mixing for 10 mins, the samples were placed on ice for 10 min then centrifuged. The pH of the supernatants was neutralized with a solution of ammonium formate (0.15M) with ammonium hydroxide (1.16 M). The aqueous solution was evaporated and reconstituted in a solution of EDTA (20 µM) in water for LC-MS analysis. LC-MS was performed using a Waters Alliance System 2795 (Waters; Milford, Mass.) that was connected to a Waters EMD 1000 (Waters; Milford, Mass.). The compounds were separated over an Atlantis dC 18 µm 2.1×50 mm column obtained from Waters (Waters; Milford, Mass.). The mobile phases consisted of a solution of 5 mM ammonium acetate with 0.1% of acetic acid (A) and a solution of 5 mM ammonium acetate in methanol with 0.5% of acetic acid (B). The gradient began at 100% (A) and decreased to 90% (A) over 1 min, then to 30% (A) over 3 min. The mobile phase (B) increase to 100% in the next 4 min and was held at 100% for 1 min. Finally, the mobile phase returned to 100% (A) over 1 min and the column was re-equilibrated with 100% (A) for 5 min. The flow rate was constant at 0.250 mL/min and the injection volume was 10 µL. The settings of the ESI source were as follows (nomenclature as used in Empower software): capillary voltage, 4500 V; cone voltage, 20 V; desolvation gas, nitrogen, temperature, 300° C. and flow, 600 L/Hr; source temperature at 150° C. Single ions were recorded. The monitored ions (positive mode) were $NAD^+$ (m/z 664) and the internal standard 2-ClAde (m/z 302). A solution of nicotinamide adenine dinucleotide ($NAD^+$) (Sigma-Aldrich; St. Louis, Mo.) in water was used as reference.

7.1.9 NF-κB Regulated Gene Expression

HeLa cells were seeded at a density of $3-5\times10^6$ cells in a 150 mm dish and grown overnight prior to transfection. Cells were then cotransfected with an NF-κB regulated firefly luciferase gene (NFκB-luc, Cat. No. LR0051; Panomics; Redwood City, Calif.) and a construct containing a basal promoter regulated Renilla luciferase gene (phRL-TK) (Promega #E6241; Madison, Wis.) which serves as an internal control for general changes in gene transcription and cytotoxicity. A total of 15 µg of DNA was added to cells in a volume of 4 mL Optimem (Invitrogen; Carlsbad, Calif.) and 45 µl of Lipofectamine 2000 (Invitrogen; Carlsbad, Calif.) at a ratio of 9.5:1 NF-κB-luc:TK-RLluc and incubated at 37° C. overnight. Transfected cells were then harvested by trypsinization, counted and plated at 5,000 cells per well in quadruplicate. Cells were treated immediately with DMSO or Compound 1 (100 nM) in the presence or absence of nicotinic acid (10 µM) for 24 hours followed by a 4 hour stimulation with TNFα (50 ng/ml) to induce NF-κB transcription factors. Firefly and Renilla luciferase levels were quantified with the Dualglo luciferase assay according to manufacturer's instructions using a luminometer (EG&G Berthold; Oak Ridge, Tenn.). NF-κB regulated firefly luciferase activity was normalized to the Renilla luciferase in each replicate and then expressed as a percentage of the mean of untreated samples.

7.1.10 Synthesis of $NAD^+$ from Nicotinamide or Nicotinic Acid

In vivo: HeLa cells ($1\times10^6$ per sample) were plated 14-16 hours prior to the start of drug treatment. Cells were then treated with DMSO or Compound 1 (20 nM) for 2 hours and then treated with 0.5 µCi of $^{14}C$-nicotinamide (1 µM) or 0.05 µCi of $^{14}C$-nicotinic acid (100 nM) (Moravek Biochemicals; Brea, Calif.) and incubated for an additional 6 hours. Cells were harvested by trypsinization and collected by centrifugation, and cell pellets resuspended in 50 µl of 10 mM $NaH_2PO_4$. To extract the radiolabeled nucleotide metabolites, the cells were lysed by 6 freeze-thaw cycles of liquid nitrogen/37° C. water bath. Precipitates were removed by centrifugation at 13,000 g for 20 mins.

In vitro: Untreated HeLa cells were harvested by trypsinization, collected by centrifugation and resuspended at $2.5\times10^7$ cells/mL in 10 mM $NaH_2PO_4$ buffer then cell extracts were made by 6 freeze-thaw cycles as above and cell extracts clarified by centrifugation at 23,000 g at 4° C. for 90 mins. 20 µL of extract was incubated in the presence or absence of 20 nM Compound 1 in an enzymatic reaction buffer containing 5 mM $MgCl_2$, 2 mM ATP, 0.5 mM phosphoribosyl pyrophosphate, 500 nM $^{14}C$-nicotinamide or 50 nM $^{14}C$-nicotinic acid at 37° C. for one (nicotinamide) or 2 (nicotinic acid) hours in a total reaction volume of 50 µL. The reaction was terminated by incubation at 100° C. for 2 mins. The radiolabeled nucleotides were separated by thin-layer chromatography and identified by comparison with radiolabeled standards of $NAD^+$, its precursors and metabolites (Moravek Biochemicals; Brea, Calif.). Approximately 10 µL of each sample was spotted onto Silica gel 60 plates (Merck KGaA, EMD chemicals Inc; Gibbstown, N.J.) and resolved in a solvent of isobutyric acid:ammonium hydroxide:water (66:1:33) overnight. The dried TLC plates were then exposed to BAS-MS screens (Fuji Photo Film Co. LTD; Kanagawa, Japan) for 2-3 days, scanned on a Typhoon Imager (Amersham; Piscataway, N.J.).

7.1.11 Expression and Purification of Recombinant NMPRT

Human NMPRT cDNA (Origene; Rockville, Md.) was cloned into the pET151 vector (Invitrogen; Carlsbad, Calif.). The resulting construct encodes a recombinant NMPRT protein with hexahistidine and FLAG epitope tags at the $NH_2$-terminus. Four litres of BL21(DE3)pLysS bacteria (Invitrogen; Carlsbad, Calif.) at O.D. ~0.6 in LB media were induced to express the NMPRT protein with 200 µM IPTG (Roche Diagnostics; Mannheim, Germany) for 3.5 hours with shaking (250 rpm) at 37° C. The bacterial cells were harvested by centrifugation at 6,000 g for 15 minutes at 4° C., the supernatant was discarded and the cells frozen at −20° C. Frozen cell pellets were thawed and resuspended in 160 mL of Lysis buffer (20 mM Tris-HCl pH 8.0, 300 mM NaCl, 0.1% Triton X-100, 1 mM pefabloc (Roche Diagnostics; Mannheim, Germany), 1 µg/mL each of aprotinin (Roche Diagnostics; Mannheim, Germany), leupeptin (Roche Diagnostics; Mannheim, Germany) and pepstatin (Roche Diagnostics; Mannheim, Germany) and sonicated six times for 15 seconds (65% amplitude, Fisher Scientific model 500, Ottawa, ON) with one minute rest between pulses. The cell extract was clarified by centrifugation at 57,000 g for 30 minutes at 4° C. and the pellet was discarded. $Ni^{2+}$-NTA agarose beads (Quiagen; Mississauga, ON) (6.4 mL) were equilibrated with Lysis buffer and then incubated with the clarified bacterial cell extract for 2 hours with rotation at 4° C. Beads were collected by centrifugation at 2,000 g for 3 minutes at 4° C. The supernatant was discarded and the beads were washed six times with Wash buffer (20 mM Tris-HCl pH 8.0, 300 mM NaCl, 10% glycerol, 0.1% Triton X-100 and 40 mM Imidazole) and collected as above. $His_6$-NMPRT protein was eluted from the beads with 24 mL Elution buffer (Wash buffer plus 150 mM Imidazole). $His_6$-NMPRT recombinant protein was concentrated using Amicon Ultra-15 centrifugal filter concentrators (Millipore; Billerica, Mass.) and stored in small aliquots at −80° C. The protein concentration was determined by Bradford assay (Bio-Rad; Hercules, Calif.).

7.1.12 Recombinant NMPRT Assays

The activity of recombinant NMPRT was assessed using a coupled-enzyme fluorescence assay based on the quantitation of NAD$^+$. Recombinant full length human NMNAT1 was purchased from Alexis Biochemicals (Alexis Biochemicals Inc.; San Diego, Calif.). Recombinant NMPRT was generated as described above. Reactions were carried out in 96 well white plates (Corning; Corning, N.Y.) in 50 mM HEPES buffer, pH 7.4, 50 mM KCl, 5 mM MgCl$_2$, 0.5 mM β-mercaptoethanol, 0.005% BSA, 1% DMSO, 2.0 U/mL LDH (Sigma-Aldrich; St. Louis, Mo., L2500), 4 mM sodium L-lactate (Sigma-Aldrich; St. Louis, Mo., L7022), 0.4 U/mL Diaphorase (Sigma-Aldrich; St. Louis, Mo., D5540), 6 μM Resazurin sodium salt, 0.4 mM PRPP, 3.0 nM NMNAT1, 125 μM ATP, 50 μM nicotinamide and 2-5 μM recombinant NMPRT at room temperature for 180 minutes. Fluorescence was measured using a Tecan Safire plate reader (Tecan-US; Durham, N.C.) with an excitation wavelength of 560 nm and emission wavelength of 590 nm. The K$_m$ for nicotinamide was determined for every preparation of the enzyme and a titration of NAD$^+$ was run with every assay to ensure that measurements were within the linear range. Titration curves for the inhibition of NMPRT by Compound 1 were carried out using tenfold dilutions starting with a concentration of 10 μM. The K$_i$ was calculated using Prism version 4.0 (Graphpad Software, Inc; San Diego, Calif.) and the Cheng-Prusoff Equation. The Cheng-Prusoff Equation is $K_i = IC_{50}/(1+[S]/K_m)$, where [S] is substrate (nicotinamide) concentration.

7.1.13 Expression of Yeast Pnc1 in Mammalian Cells

The *Saccharomyces cerevisiae* PNC1 gene was amplified from yeast genomic DNA and cloned into pcDNA3 vector (Invitrogen, Carlsbad, Calif.) to generate a construct (pc-FLAGPNC1) encoding a FLAG epitope at the NH2-terminus of the expressed pnc1 protein. For transient transfection into HeLa cells, 5 μg of pcDNA3, pcFLAGPNC1 or pcDNA3-HAE-GFP (to measure transfection efficiency) was diluted into 1.5 mL of Opti-MEM (Invitrogen, Carlsbad, Calif.) reduced serum media. 60 μL of Lipofectamine 2000 (Invitrogen, Carlsbad, Calif.) was diluted in 6 mL of Opti-MEM (Invitrogen; Carlsbad, Calif.) reduced serum media and incubated at room temperature for 15 minutes. Equal volumes of diluted plasmid and diluted Lipofectamine 2000 (Invitrogen, Carlsbad, Calif.) were mixed gently and incubated at room temperature for 15 minutes. 3 mL of each plasmid mixture was added to a 100 mm culture dish plated with 1×10$^6$ HeLa cells grown overnight in 11 mL of antibiotic free RPMI-1640 (Hyclone; Logan, Utah) supplemented with 10% FBS. After 24 hours growth at 37° C. each plate was split into 96 well white plates (pcDNA3, pcFLAGPNC1) or 96 well clear bottom plates (pcDNA3-HAE-GFP) at a density of 1,000 cells per well. The efficiency of transfection was assessed by viewing the expression of GFP from the pcDNA3-HAE-GFP transfected cells under a Axiovert S 100 TV fluorescence microscope (Carl Zeiss, Mikroscopie, Jena, Germany). The transfection efficiency was between 40-50% of the HeLa cells transfected after 24 hours. The pcDNA3 and pcFLAGPNC1 transfected cells were treated with varying concentrations of Compound 1 as indicated. Cell viability was assessed by ViaLight assay as described above.

The expression of Pnc1 protein was monitored by western blot analysis of cell extracts. Briefly, transfected cells were harvested by trypsinization and lysed with 20 mM Tris-HCl pH 8.0, 60 mM KCl, 1 mM EDTA, 1 mM dithiothreitol, 0.5% NP-40 (Igepal), 1 mM Pefabloc (Roche Diagnostics; Mannheim, Germany) and 1 μg/mL each of aprotinin (Roche Diagnostics; Mannheim, Germany), leupeptin (Roche Diagnostics; Mannheim, Germany) and pepstatin (Roche Diagnostics; Mannheim, Germany). After centrifugation at 13,000 g for 15 minutes at 4° C., the protein concentration of the supernatant was determined using the Bradford assay (Bio-Rad; Hercules, Calif.). 20 μg of cell extract was separated on 12.5% Criterion pre-cast gels (Bio-Rad; Hercules, Calif.). The proteins were transferred to Immobilon-P (Millipore; Billerica, Mass.) PVDF membrane and blocked with 5% nonfat milk/Tris-buffered saline (TBS)/0.1% Tween (Sigma-Aldrich; St. Louis, Mo.) for 1 hour at room temperature. The membrane was incubated with a mouse anti-FLAG antibody (Sigma-Aldrich; St. Louis, Mo.) at a dilution of 1:2000 in 5% nonfat milk/TBS/0.1% Tween overnight at 4° C. After washing 4 times five minutes each with TBS/0.1% Tween, the membrane was incubated with HRP-conjugated goat anti-mouse antibody at a dilution of 1:5000 in 5% nonfat milk/TBS/0.1% Tween for 1 hour at room temperature. After four washes of 5 minutes each in TBS/0.1% Tween, the level of FLAG-PNC1 protein was revealed with the ECL Plus (Amersham; Piscataway, N.J.) western blotting detection reagent. Chemiluminescence was detected with a Versadoc instrument (Bio-Rad; Hercules, Calif.).

7.1.14 siRNA-Mediated Knockdown of NMPRT in HeLa Cells

HeLa cells were plated at 750×10$^5$ cells per 100 mm culture dish and grown overnight in media without antibiotics. Cells were transfected with 50 nM On-Target plus Smartpool hNMPRT siRNA (Dharmacon; Lafayette, La., L-004581-00-0020) or On-Target plus siControl (non-targeting) siRNA (Dharmacon; Lafayette, La., D-001810-01-0020) using Opti-MEM (Invitrogen; Carlsbad, Calif.) reduced serum media and Oligofectamine (Invitrogen; Carlsbad, Calif.) siRNA transfection reagent (optimized at 24 μL per 100 mm dish). A second identical transfection was done 24 hours after the initial transfection. 24 hours following the second transfection, cells were trypsinized and replated into 96 well white plates at a cell density of 2000 cells per well for the Compound 1 titration. Cells were treated with various concentrations of Compound 1 at 37° C. for 72 hours at which time viability was assessed using the ViaLight assay described above. To measure the level of NMPRT protein reduction, a sample of the siRNA treated cells was harvested at 24 hours after the second siRNA transfection. These cells were lysed with 20 mM HEPES pH 7.4, 150 mM NaCl, 1 mM EDTA, 1 mM dithiothreitol, 2% CHAPS (Sigma-Aldrich; St. Louis, Mo.), 1 mM pefabloc (Roche Diagnostics; Mannheim, Germany) and 1 μg/mL each of aprotinin (Roche Diagnostics; Mannheim, Germany), leupeptin (Roche Diagnostics; Mannheim, Germany) and pepstatin (Roche Diagnostics; Mannheim, Germany) by pipetting up and down 10-15 times and incubation on ice for 15 minutes. After centrifugation at 13,000 g for 15 minutes at 4° C., the protein concentration of the supernatant was determined using the Bio-Rad Bradford assay (Bio-Rad; Hercules, Calif.). 25 μg of cell extract was separated on 12.5% Criterion pre-cast gels (Bio-Rad; Hercules, Calif.). The proteins were transferred to Immobilon-P (Millipore; Billerica, Mass.) PVDF membrane and blocked with 5% nonfat milk/Tris-buffered saline (TBS)/0.1% Tween for 1 hour at room temperature. The membrane was incubated with a rabbit anti-NMPRT antibody (Abcam; Cambridge, Mass.) at a dilution of 1:1000 in 5% nonfat milk/TBS/0.1%

Tween for 2 hours at room temperature with shaking. After washing 4 times for five minutes each, the membrane was incubated with HRP-conjugated goat anti-mouse antibody at a dilution of 1:5000 in 5% nonfat milk/TBS/0.1% Tween for 1 hour at room temperature. After two washes of 10 minutes each in TBS/0.1% Tween followed by two washes of 10 minutes each in TBS the level of NMPRT protein was revealed with ECL Plus (Amersham; Piscataway, N.J.) western blotting detection reagent. Chemiluminescence was detected with a Versadoc instrument (Bio-Rad; Hercules, Calif.) and the level of protein was quantitated using the Bio-Rad Quantity One software (Bio-Rad; Hercules, Calif.). Subsequently, the membrane was probed with rabbit anti-GAPDH antibody (Abcam; Cambridge, Mass.) at a dilution of 1:2000 and GAPDH protein levels were assessed as above. The level of NMPRT expression was normalized to the level of GAPDH protein expression resulting in 90% knockdown of NMPRT protein.

7.1.15 Pearson Correlation Analysis

Mean $IC_{50}$ values of Compound 1 by 72 hour ViaLight assay were determined in 2-4 independent experiments for 25 of the NCI panel of 60 cell lines described. Relative mRNA expression level values (Microarray data—from Novartis, measured on Affymetrix U95Av2 arrays) for the same 25 cell lines were obtained from the NCI DTP Molecular targets program (http://dtp.nci.nih.gov/mtargets/download.htm), Experiment # 89629, pattern ID# GC95997. Pearson correlation analysis for these two data sets were performed in GraphPad Prism Version 4.00 (Graphpad Software, Inc.; San Diego, Calif.).

7.2 Example 1

Kinetic and Biochemical Pathway Profiling Studies in IM-9 Cells Treated with Compound 1

Figure 1C:
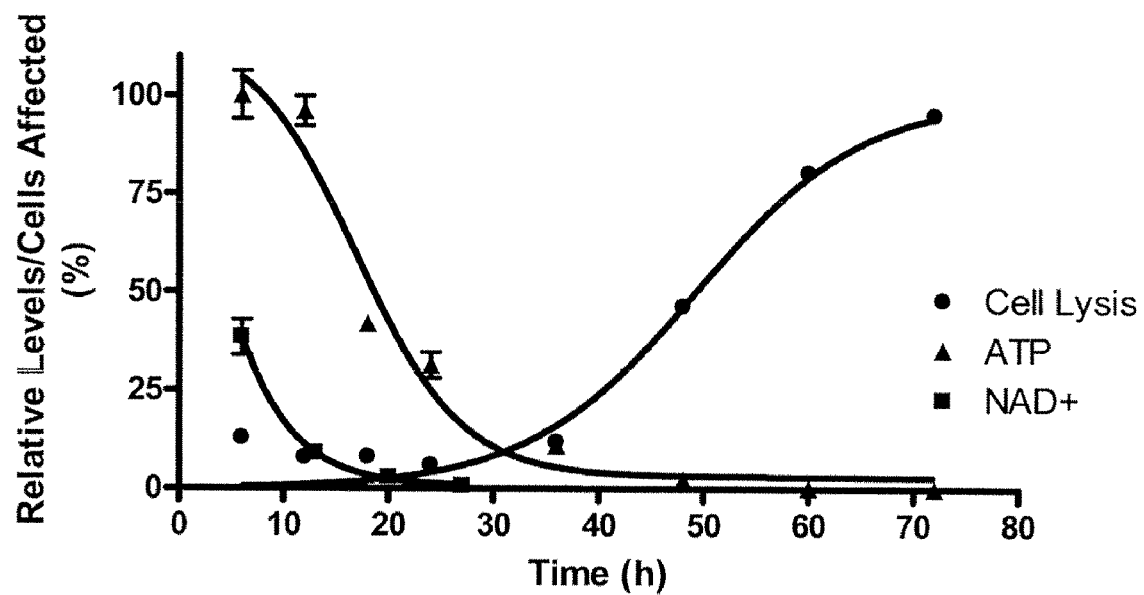

FIG. 1A shows a scatter plot representing the mean fold change in 88 metabolites detected in Compound 1 treated (30 nM) IM-9 cells relative to untreated time-matched control samples. Each point represents the mean of 6 replicate cell samples extracted and analyzed by quantitative GC/MS and LC/MS. FIG. 1B shows the kinetics of $NAD^+$ levels, ATP levels and cell lysis over time in cells treated with 30 nM Compound 1. Cells were treated with Compound 1 for a 72 hr continuous exposure, and then assayed for $NAD^+$ levels, ATP levels, and cell lysis at various times after compound addition. $NAD^+$ levels were measured by LC/MS and is expressed as the mean±SD of 6 replicates. ATP levels were assessed by ViaLight assay and is represented as a percentage of untreated control samples. Each point represents the mean±SD of triplicate samples. Cell lysis was measured by fluorescence-activated cell-sorting (FACS) analysis of cells stained with propidium iodide. Each point represents the percentage of cells staining positive in a single sample of 10,000 cells.

7.3 Example 2

Figure 2:
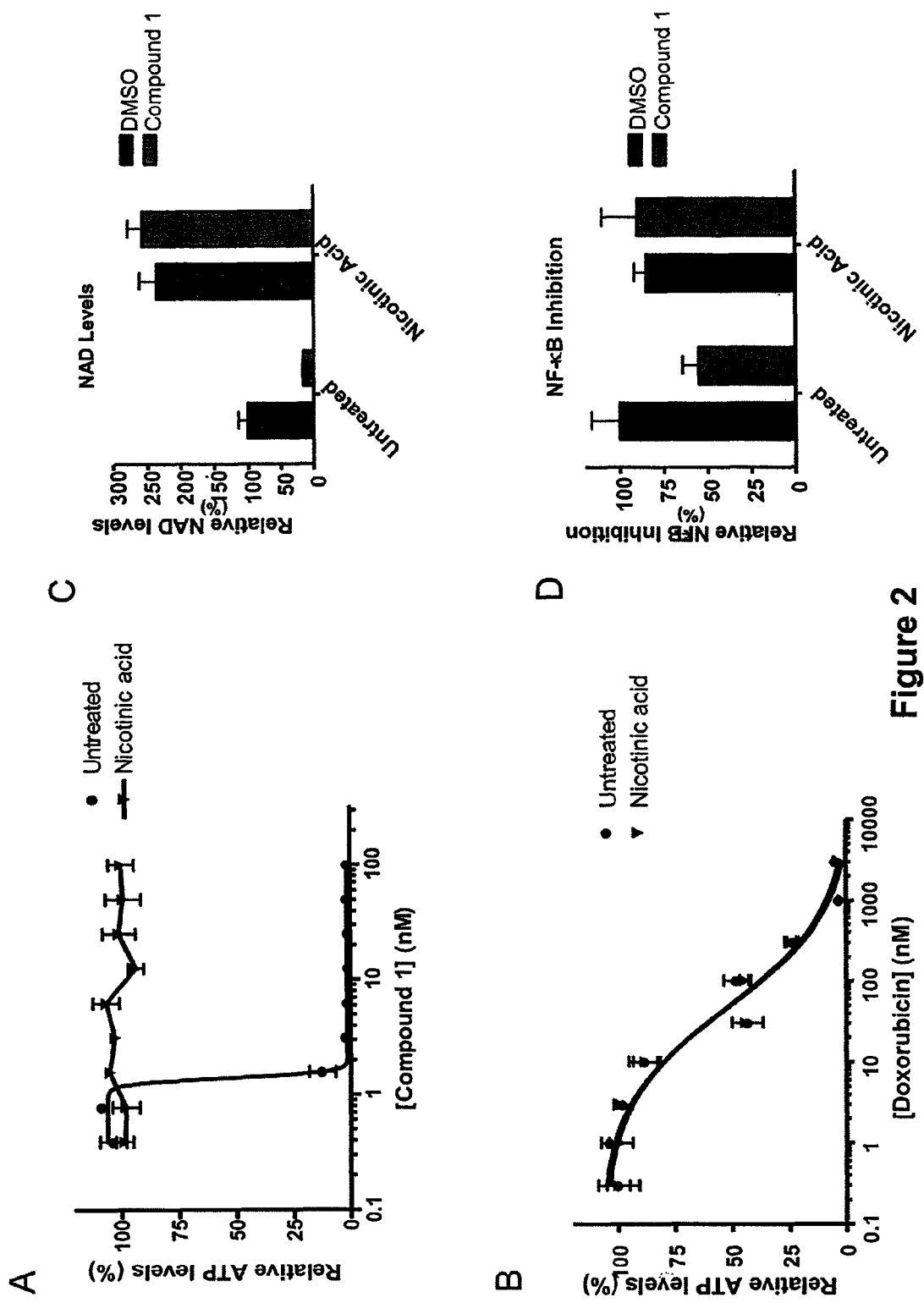
FIGS. 2A, 2B, 2C and 2D are graphic representations that show that nicotinic acid can rescue HeLa cells treated with a NMPRT inhibitor (Compound 1) from cytotoxicity, $NAD^+$ level decline, and NF-κB inhibition.

Nicotinic Acid Can Rescue Cell Cytotoxicity, $NAD^+$ Decline and NF-κB Inhibition HeLa Cells Treated with a NMPRT Inhibitor HeLa cells were treated with various concentrations of a NMPRT Inhibitor (Compound 1) (FIG. 2A) or Doxorubicin (FIG. 2B), in the presence or absence of nicotinic acid (10 mM). Viability was measured after 72 hours by ViaLight assay (assessing ATP levels). Relative viability was determined by expressing ATP levels relative to untreated or nicotinic acid treated cell controls without Compound 1. As shown in FIG. 2C, $NAD^+$ was extracted and quantified by LC/MS from untreated or Compound 1 (100 nM) treated HeLa cells in the presence or absence of 10 mM nicotinic acid. $NAD^+$ levels are expressed as the mean±SD of duplicate samples relative to untreated samples without nicotinic acid. As shown in FIG. 2D, NF-κB regulated gene expression was measured in HeLa cells after transient co-transfections of an NF-κB regulated firefly luciferase construct and a basal promoter (TK) renilla luciferase construct. Cells were treated with DMSO or Compound 1 (100 nM) in the presence or absence of 10 mM nicotinic acid for 24 hrs followed by 4 hours of TNFα treatment to induce NF-κB transcription factors. NF-κB regulated luciferase activity (normalized to TK) is expressed relative to untreated samples without nicotinic acid. Each bar is the mean±SD of quadruplicate samples. Each figure is representative of two independent experiments. The results show that nicotinic acid can rescue a cell treated with a NMPRT inhibitor from cytotoxicity, decline in $NAD^+$ levels, and NF-κB inhibition.

7.4 Example 3

Rescue of NMPRT Inhibitor Cytotoxicity by Nicotinic Acid

Figure 3:
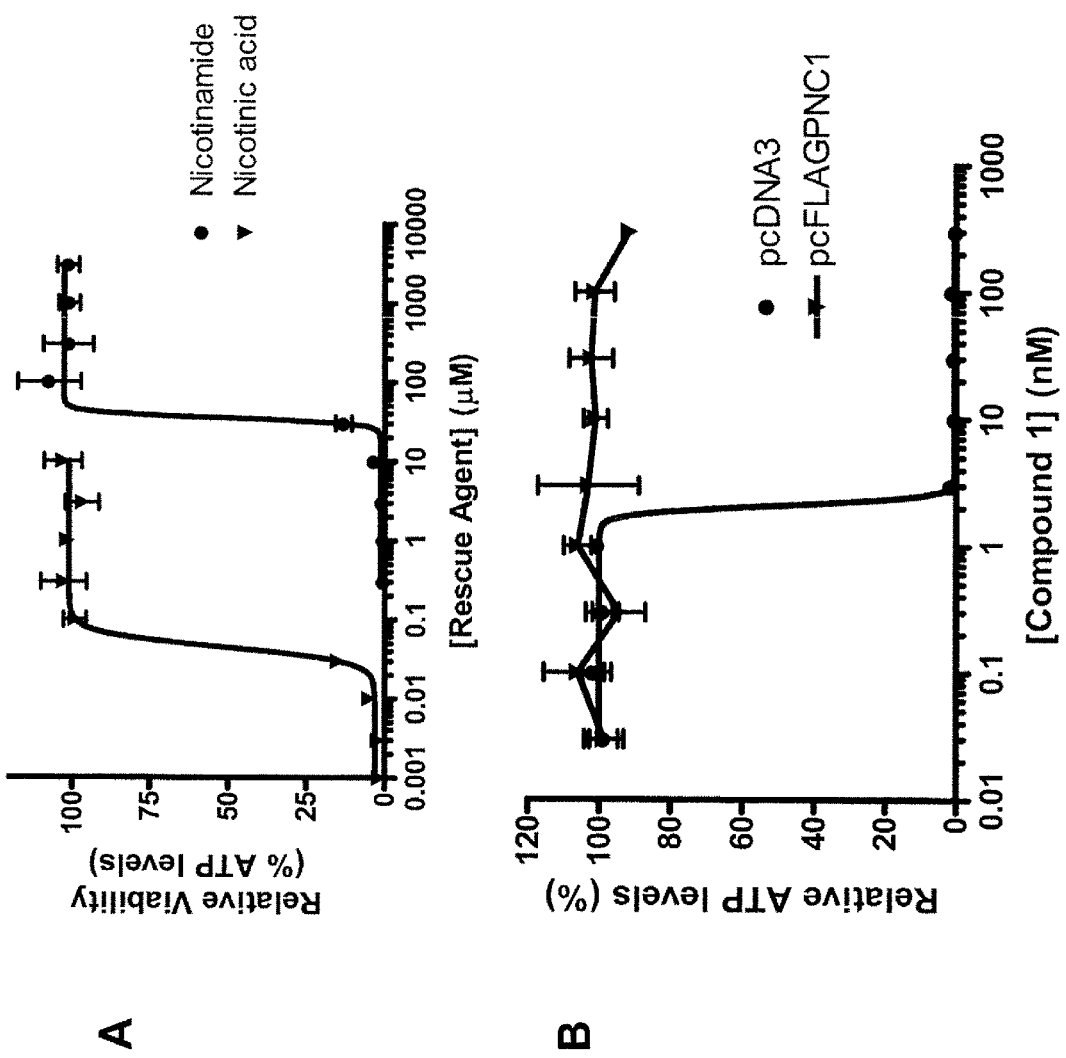
FIG. 3A is a graphic representation that shows that nicotinic acid, but not nicotinamide, can rescue a cell from cytotoxicity of a NMPRT inhibitor (Compound 1)
FIG. 3B is a graphic representation that shows that overexpression of yeast PNC 1 gene (pcFLAGPNC 1) can rescue a cell from a NMPRT inhibitor (Compound 1) cytotoxicity.

As shown in FIG. 3A, nicotinic acid, but not nicotinamide can rescue NMPRT Inhibitor (Compound 1) induced cytotoxicity. HeLa cells were treated with Compound 1 alone at a lethal concentration of 20 nM or with increasing doses of nicotinic acid (NA) or nicotinamide (NM) added to the media. Viability was measured after 72 hours by ViaLight assay. Relative viability was determined by expressing ATP levels of Compound 1 treated cells relative to the levels in cells treated with corresponding levels of NA or NM. Each point represents the mean and error bars the SD of triplicate samples. The NM used in this experiment was determined to contain 0.1% NA, which is believed to be the reason why it rescued viability in cells at concentrations 1,000× higher than those required for NA rescue. Pnc1 is a nicotinamidase that converts nicotinamide to nicotinic acid. As shown in FIG. 3B, overexpression of the yeast PNC1 gene also rescued cells from Compound 1 cytotoxicity. The concentration of nicotinamide in RPMI 1640 media was 8 mM. HeLa cells were transiently transfected with vector (pcDNA3) or a plasmid expressing a flag-tagged yeast PNC1 gene (pcFLAG-PNC 1). Twenty four hours after transfection cells were replated into 96-well plates and Compound 1 was added at various concentrations. Relative viability was assessed after 72 hours by ViaLight assay.

7.5 Example 4

Metabolism of Nicotinamide, but not Nicotinic Acid, is Blocked by Compound 1

Figure 4:
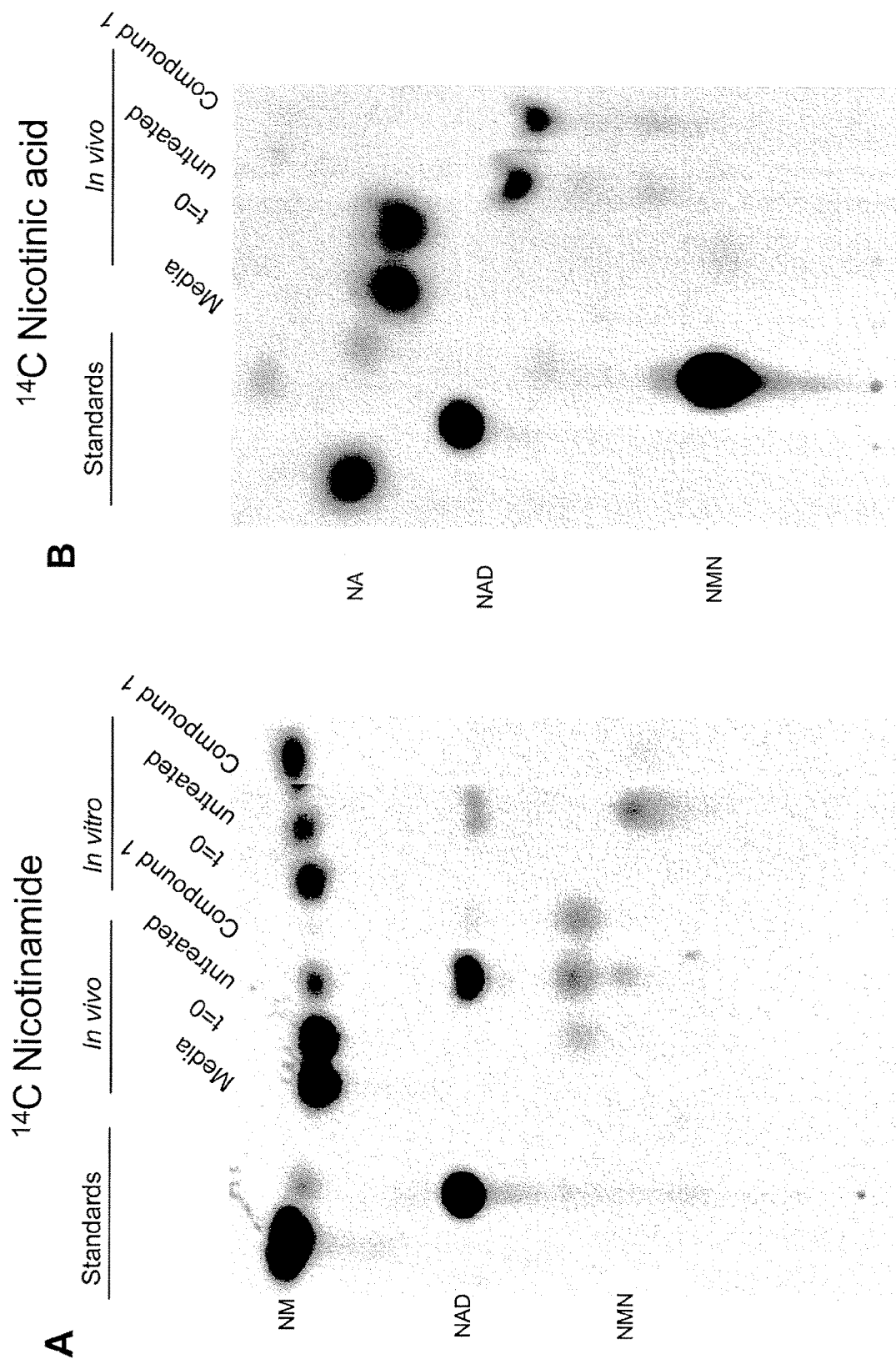
FIGS. 4A and 4B are TLC representations that show that metabolism of nicotinamide, but not nicotinic acid, is blocked by a NMPRT inhibitor (Compound 1)

The conversion of $^{14}C$ nicotinamide (FIG. 4A) or $^{14}C$ nicotinic acid (FIG. 4B) to $^{14}C$-labeled $NAD^+$ was measured in HeLa cells (in vivo) or in HeLa cell extracts (in vitro). In vivo metabolism: HeLa cells were treated with Compound 1 (20 nM) for 2 hours and then $^{14}C$ labeled nicotinamide (1 μM)

or nicotinic acid (100 nM) added to the media for an additional 6 hours. Media control samples indicate where labeled precursors were added to media without cells and then extracted. Controls (t=0) indicate labeled precursors were added to HeLa cells in culture and extracted immediately instead of after 6 hrs. Cells were rinsed, harvested, extracts made by freeze/thaw lysis and clarified by centrifugation. In vitro metabolism: $^{14}$C labeled nicotinamide (500 nM) or nicotinic acid (50 nM) was added to a buffer containing DMSO or Compound 1 (20 nM) and incubated for 1-2 hours. Clarified extracts containing radiolabeled nucleotides from in vivo and in vitro metabolism reactions were spotted onto a silica coated TLC plate and resolved in a solvent of isobutyric acid:ammonium hydroxide:water 66:1:33). FIGS. 4A and 4B show that Compound 1 blocks NAD synthesis from nicotinamide, but not from nicotinic acid.

7.6 Example 5

Compound 1 is a Potent Inhibitor of Recombinant NMPRT In Vitro

Figure 5:
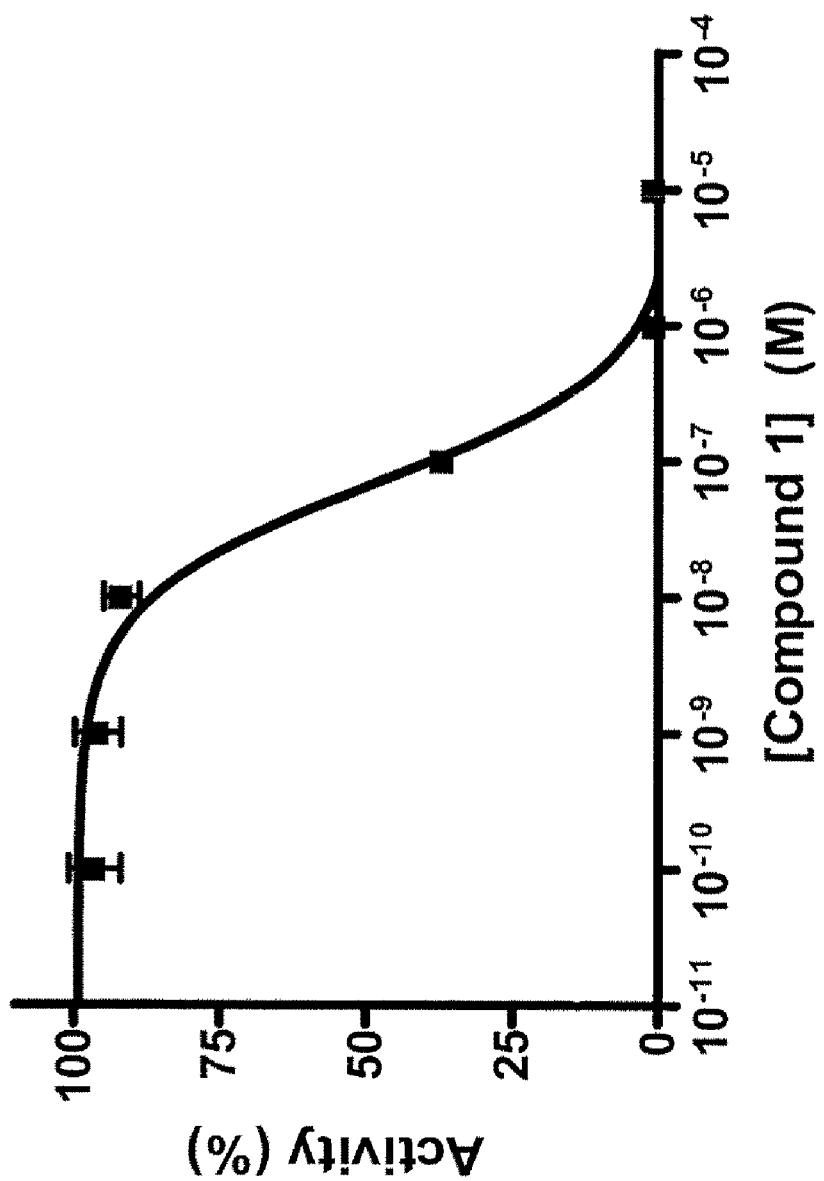
FIG. 5 is a graphic representation that shows in vitro activity of a NMPRT inhibitor (Compound 1) against recombinant NMPRT.

A coupled assay with fluorescent readout was used to measure the effects of Compound 1 on His-Flag tagged recombinant NMPRT purified from bacterial extracts. The inhibitory activity of Compound 1 is shown in FIG. 5. Table 3 shows the inhibition constant ($K_i$) against NMPRT for Compound 1 in two independent experiments, calculated as described in Section 6.1.12. $IC_{50}$ value for the compound was determined in IM-9 and HCT-116 cells by ViaLight essay as described supra.

TABLE 3

| | | $IC_{50}$ (nM) Cell viability assay (72 h) | |
|---|---|---|---|
| | $K_i$ (nM) | | |
| Compound | Recombinant NMPRT | IM-9 (Multiple myeloma) | HCT-116 (Colon) |
| Compound 1 | 1.0 | 3.33 ± 0.66 | 2.30 ± 0.64 |

7.7 Example 6 siRNA Knockdown of NMPRT Causes Increased Sensitivity to Compound 1

Figure 6:
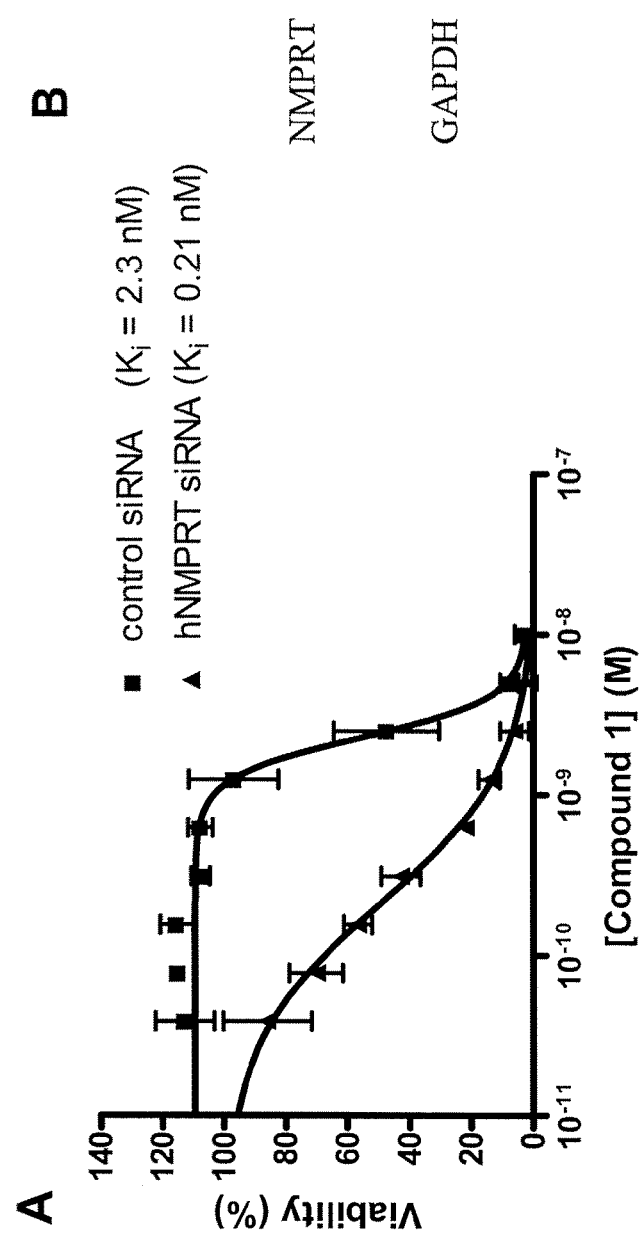
FIGS. 6A and 6B are a graphic representation and Western blot representation, respectively, that show that siRNA knockdown of NMPRT causes increased sensitivity to a NMPRT inhibitor (Compound 1)

HeLa cells were transfected twice with siRNA oligos which were either scrambled (control siRNA) or were directed against the NMPRT gene (hNMPRT siRNA). 24 hours after the second transfection, cells were replated into 96-well plates and treated with various concentrations of Compound 1. Viability was measured after 72 hours by ViaLight assay. Relative viability was determined by expressing ATP levels relative to DMSO treated cells, as shown in FIG. 6A. Each point represents the mean±SD of triplicate samples. As shown in FIG. 6B, the level NMPRT protein knockdown was measured by Western blot analysis using an anti-NMPRT antibody and was determined to be approximately 90% of siControl transfected samples.

7.8 Example 7

The Expression of NMPRT Correlates with Sensitivity to Compound 1

Figure 7A:
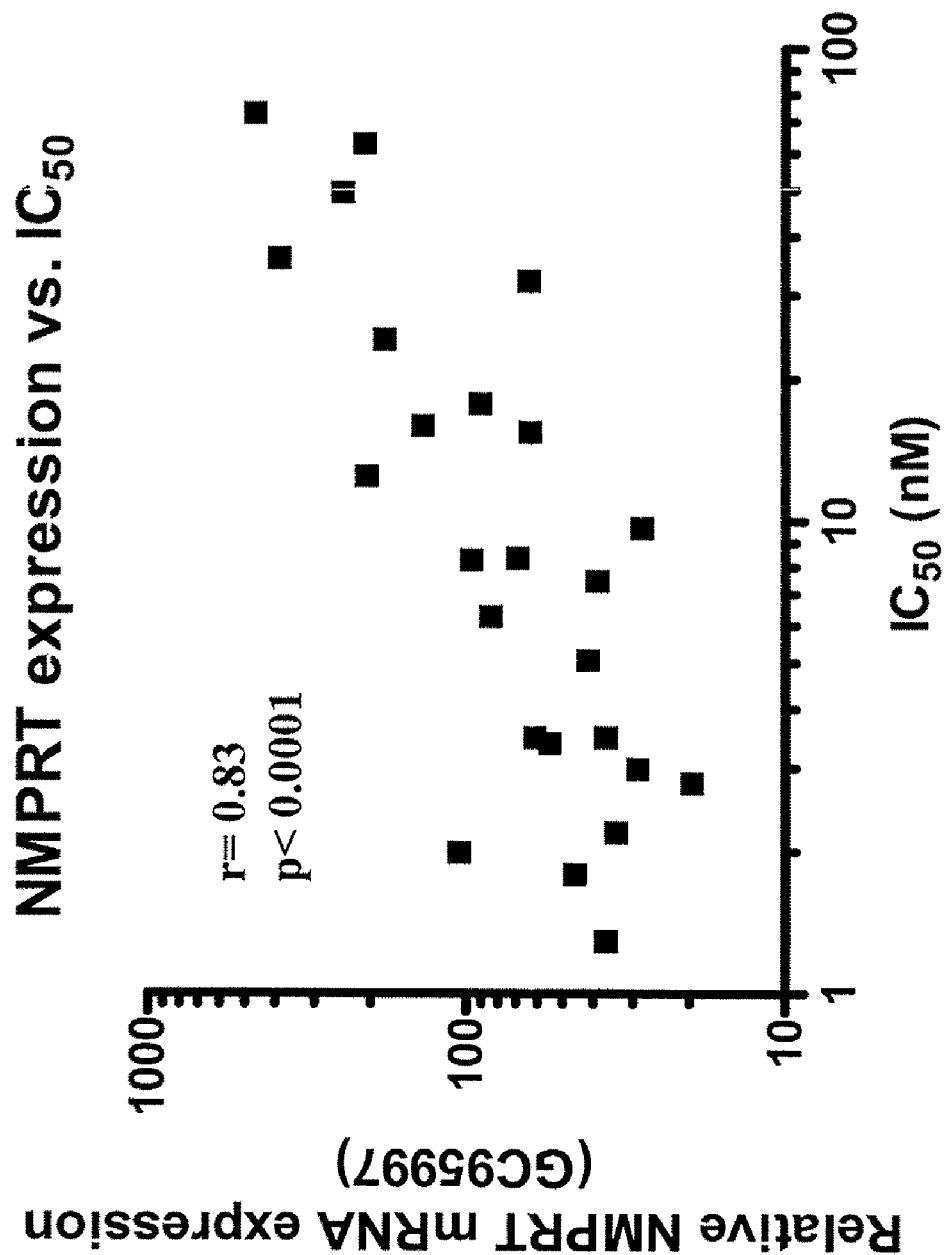
FIG. 7A is a graphic representation that shows that the expression of NMPRT is correlated with sensitivity to a NMPRT inhibitor (Compound 1)
Figure 7B:
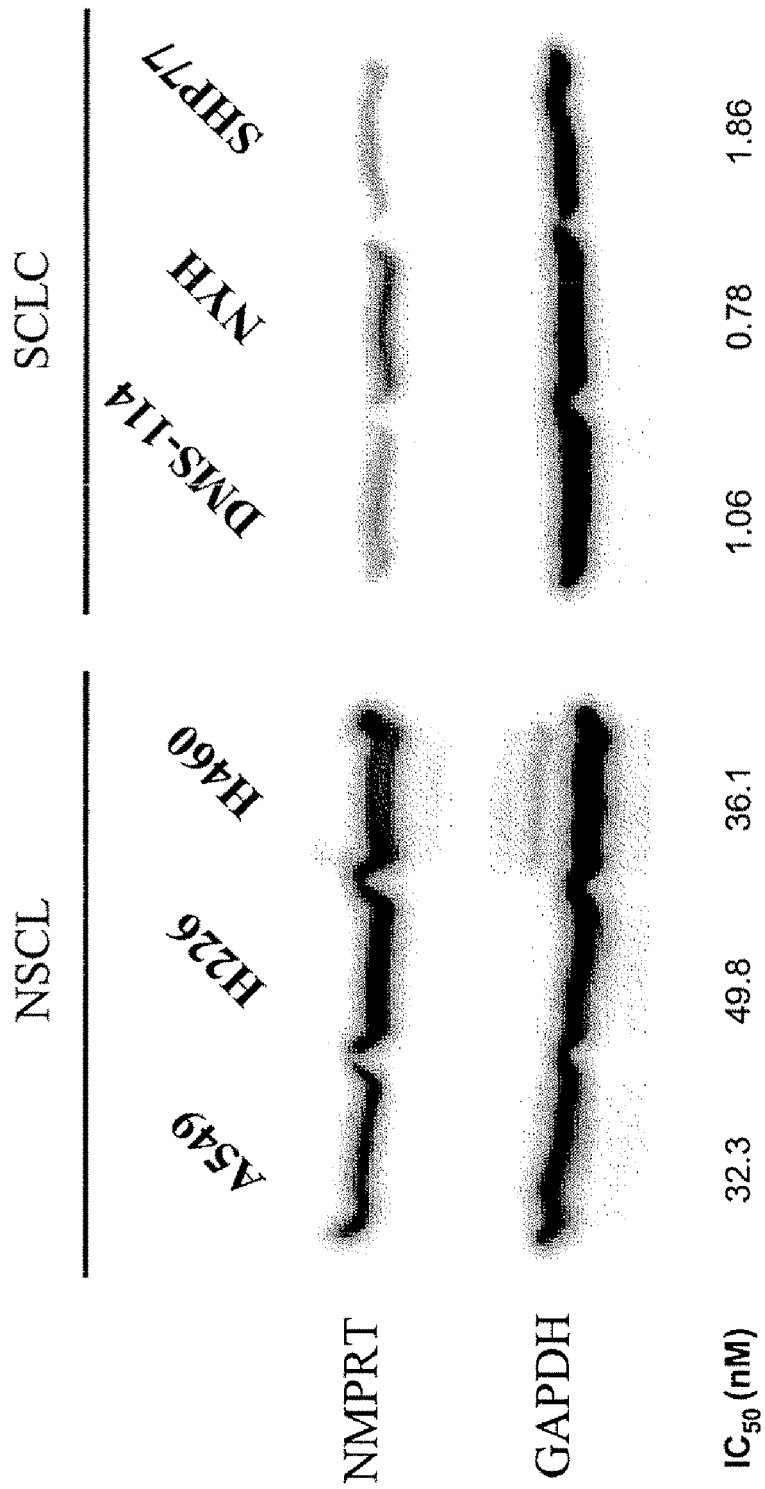
FIG. 7B is a Western blot representation that shows a comparison of endogenous NMPRT protein levels in small cell lung carcinoma (SCLC) and non-small cell lung carcinoma (NSCL) cell lines.

Cell viability ($IC_{50}$ values) for Compound 1 in 25 of the NCI panel of 60 cell lines was determined by 72 hour ViaLight assay. Relative mRNA expression levels of NMPRT for the same cell lines was obtained from the NCI DTP Molecular targets database as determined by Gene chip analysis. As shown in FIG. 7A, the Pearson correlation coefficient (r=0.83) and p<0.0001 was determined by correlation analysis and indicates a strong correlation. FIG. 7B shows a Western blot comparing endogenous NMPRT protein levels in small cell lung carcinoma (SCLC) and non-small cell lung carcinoma (NSCL) lung cancer cell lines. GAPDH protein was used as control. The corresponding $IC_{50}$ values are indicated for each cell line.

7.9 Example 8

Nicotinic Acid (Niacin) Provides an Antidote to a NMPRT Inhibitor

CB17 SCID female mice, 5 mice per group, who were not bearing tumors were administered a lethal dose of Compound 2 as a 24 h infusion of Compound 2 at 650 mg/kg. Thereafter, mice were infused with saline for 24 h (Group 1); a niacin solution (12 mg/mL) for 4 hours at a dose of 90 mg/m2/h (30 mg/kg/h) followed by saline for another 20 h at a flow rate of 50 μL/h (Group 2); or a niacin solution (12 mg/mL) for 24 hours at a dose of 90 mg/m$^2$/h (30 mg/kg/h) with a flow rate of 50 μL/h. Results shown in Table 4 indicate that 650 mg/kg was lethal to 3 of the 5 mice. Administration of nicotinic acid (niacin) protected all mice from Compound 2 toxicity.

TABLE 4

| | Compound 2 Treatment | | Nicotinic acid treatment | | Mortality by day 5 |
|---|---|---|---|---|---|
| Group | Dose | Duration | Dose | Duration | |
| 1 | 650 mg/kg | 24 h | — | — | 3/5 |
| 2 | 650 mg/kg | 24 h | 90 mg/m$^2$/h | 4 h | 0/4 |
| 3 | 650 mg/kg | 24 h | 90 mg/m$^2$/h | 24 h | 0/5 |

Therefore, nicotinic acid provides an antidote to a toxic or lethal level of a NMPRT inhibitor.

7.10 Example 9

Pre-Treatment with Nicotinic Acid (Niacin) Protects from NMPRT Inhibitor Toxicity Balb/C female mice (Charles River; Saint Constant, Canada), 5 mice per group, who were not bearing tumors were treated by administering an intramuscular injection of Compound 2 once a day for five days at a lethal dose of 250 mg/kg. This resulted in Compound 2 being lethal to 3 of the 5 mice. Mice pre-treated with niacin at 200 mg/kg intravenously (IV), subcutaneously (SC), or orally (PO) once a day for five days for 30 min., followed by administering an intramuscular injection of Compound 2 once a day for five days at a lethal dose of 250 mg/kg were all protected from the toxicity of Compound 2. Therefore, results in Table 5 show that niacin administered intravenously, subcutaneously, or orally provides a potent antidote to a toxic or lethal level of a NMPRT inhibitor.

TABLE 5

| Compound 2 Intramuscular Treatment (QD × 5) | Nicotinic acid pre-treatment (QD × 5) | | Mortality |
|---|---|---|---|
| Dose | Dose | Administration | by day 11 |
| 250 mg/kg | — | — | 3/5 |
| 250 mg/kg | 200 mg/kg | IV | 0/5 |
| 250 mg/kg | 200 mg/kg | SC | 0/5 |
| 250 mg/kg | 200 mg/kg | PO | 0/5 |

7.11 Example 10

Sensitization of Cells to a DNA Damaging Chemotherapeutic Agent with a NMPRT Inhibitor Temozolomide exerts its cytotoxic effect through methylation of DNA at the $O^6$ position of guanine in DNA. Resistance to temozolomide can arise from the expression of the DNA-repair enzyme $O^6$-methylguanine DNA methyltransferase ($O^6$-MGMT) and/or from defects in the mismatch repair (MMR) pathway (Mhaidat et al., 2007, *British Journal of Cancer* 97: 1225-1233). Streptozotocin exerts its cytotoxic effects through DNA alkylation which causes interstrand crosslinks (Szkudelski, 2001, *Physiol. Res.* 50: 536-546). Due to an attached sugar moiety, streptozotocin is selectively taken up by β- and exocrine cells of the pancreas.

The in vitro cytotoxic effect of simultaneous treatment with DNA damaging agent temozolomide or streptozotocin and Compound 1 was characterized in glioblastoma cell line T98G and the colon carcinoma cell line HCT-116, two cell lines that exhibit resistance to temozolomide, and the melanoma cell line SK-MEL5, a non-resistant cell line. The glioblastoma cell line T98G expresses $O^6$-MGMT ($O^6$-MGMT$^+$), and the colon carcinoma cell line HCT-116 is defective in the mismatch repair pathway (MMR$^-$).

TABLE 6

| Tissue Type | Resistance Mechanism | Cell Line | Temozolomide Mean CI ± SD | n | Streptozotocin Mean CI ± SD | n |
|---|---|---|---|---|---|---|
| Melanoma | — | SK-MEL5 | 0.45 ± 0.18 | 4 | 0.34 ± 0.28 | 2 |
| Glioblastoma | $O^6$-MGMT$^+$ | T98G | 0.56 ± 0.09 | 5 | 0.56 ± 0.05 | 3 |
| Colon | MMR$^-$ | HCT-116 | 0.57 ± 0.06 | 3 | 0.39 ± 0.22 | 2 |

The combination index (CI) was calculated by the median effect method of Chou-Talalay (1984) and through the use of CalcuSyn software (Biosoft, Cambridge, UK). This method takes into account both the potency of each drug and the shape of the dose-effect curve. Concentrations of Compound 1 representing the $IC_{50}$ were combined with a dose response curve of Temozolomide or Streptozotocin. Experiments in which Compound 1 gave greater than 50% cytotoxicity alone were excluded from the analysis. CI values were calculated based on drug combinations providing a combined effect of 80% and above and are represented as the mean ± SD of all combinations tested in n separate experiments. CI < 1, = 1, and >1 indicate synergism, additive effect and antagonism, respectively. n indicates the number of experiments.

As can be seen in Table 6, the combination index (CI) for the combination of Compound 1 and the DNA damaging agent temozolomide in the cell lines tested is below 1, which indicates synergism for both the temozolomide-resistant and non-resistant cell lines. In all of the cell lines tested, streptozotocin exhibits an equivalent or slightly lower combination index than temozolomide. Taken together, these data indicate that Compound 1 is able to sensitize the T98G, HCT-116, and the SK-MEL5 cell lines to temozolomide and streptozotocin and can be used to improve the potency of these agents.

7.13 Example 11

Sensitization of Cells to a DNA Damaging Chemotherapeutic Agent with a NMPRT Inhibitor To further evaluate the ability of an illustrative NMPRT inhibitor (Compound 1) to sensitize target cells to DNA damaging chemotherapeutic agents, DMS-114 human small cell lung carcinoma and Jurkat human T cell leukemia cells were treated with increasing concentrations of DNA damaging chemotherapeutic agents and Compound 1. Treatment comprised either 0.5 nM or 0.75 nM of Compound 1 for 3 days, after which the relative ATP levels were measured to determine viability of these cells. The $IC_{50}$ values for the treatment with the DNA damaging agent were calculated relative to control cells that were treated with DMSO only. $IC_{50}$ values for the treatment with DNA damaging agent and Compound 1 were calculated relative to control cells that were treated with Compound 1 only.

TABLE 7

| DNA damaging chemotherapeutic agent | Percent viability of DMS-114 cells 0.75 nM Compound 1 (no DNA damaging chemotherapeutic agent) | IC$_{50}$ in DMS-114 cells (µM) | | Fold change |
|---|---|---|---|---|
| | | DNA damaging chemotherapeutic agent + No Compound 1 | DNA damaging chemotherapeutic agent + 0.75 nM Compound 1 | |
| Temozolomide (n = 3) | 53.20 ± 9.1 | 339.33 ± 190 | 50.1 ± 7.83 | 2.53 ± .11 |
| Carmustine (n = 5) | 47.7 ± 12 | 33.3 ± 7.3 | 11.46 ± 3.6 | 6.12 ± 7.5 |
| Streptozotocin (n = 3) | 61.9 ± 16 | 3958.0 ± 2270 | 391.2 ± 152 | 10.4 ± 4.0 |
| Ribavirin (n = 1) | 57.9 | 172.1 | 173.3 | 0.99 |

TABLE 8

| DNA damaging chemotherapeutic agent | Percent viability of Jurkat cells 0.5 nM Compound 1 + No DNA damaging chemotherapeutic agent | IC$_{50}$ in Jurkat cells (µM) | | Fold change |
|---|---|---|---|---|
| | | DNA damaging chemotherapeutic agent + No Compound 1 | DNA damaging chemotherapeutic agent + 0.5 nM Compound 1 | |
| Temozolomide (n = 3) | 76.0 ± 55 | 211.9 ± 135 | 158 ± 125 | 1.46 ± 0.26 |
| Carmustine (n = 2) | 90.1 ± 20 | 2.97 ± 1.1 | 3.13 ± 0.49 | 0.93 ± 0.21 |
| Streptozotocin (n = 3) | 80.7 ± 12 | 1013.7 ± 10 | 360.0 ± 304 | 5.63 ± 6.3 |
| Ribavirin (n = 2) | 97.6 ± 3.2 | 63.31 ± 10 | 15.53 ± 3.1 | 4.09 ± 0.16 |

Data in Tables 7 and 8 below demonstrate that the IC$_{50}$ values of the DNA damaging chemotherapeutic agents in the absence of Compound 1 are higher than in the presence of Compound 1. These results, therefore, indicate that a NMPRT inhibitor administered concurrently with the DNA damaging chemotherapeutic agents is able to sensitize the DMS-114 and Jurkat cells to these DNA damaging chemotherapeutic agents.

Additional experiments have shown that Procarbazine, Cyclophosphamide, 6-Mercaptopurine, Dexamethasone, and Paclitaxel, show less than additive effect in the presence of Compound 1. Thus, Compound 1 will not sensitize cells to these DNA damaging chemotherapeutic agents.

7.14 Example 12

Exemplary Test for a Cancer Deficient in Nicotinic Acid Pathway

Figure 8:
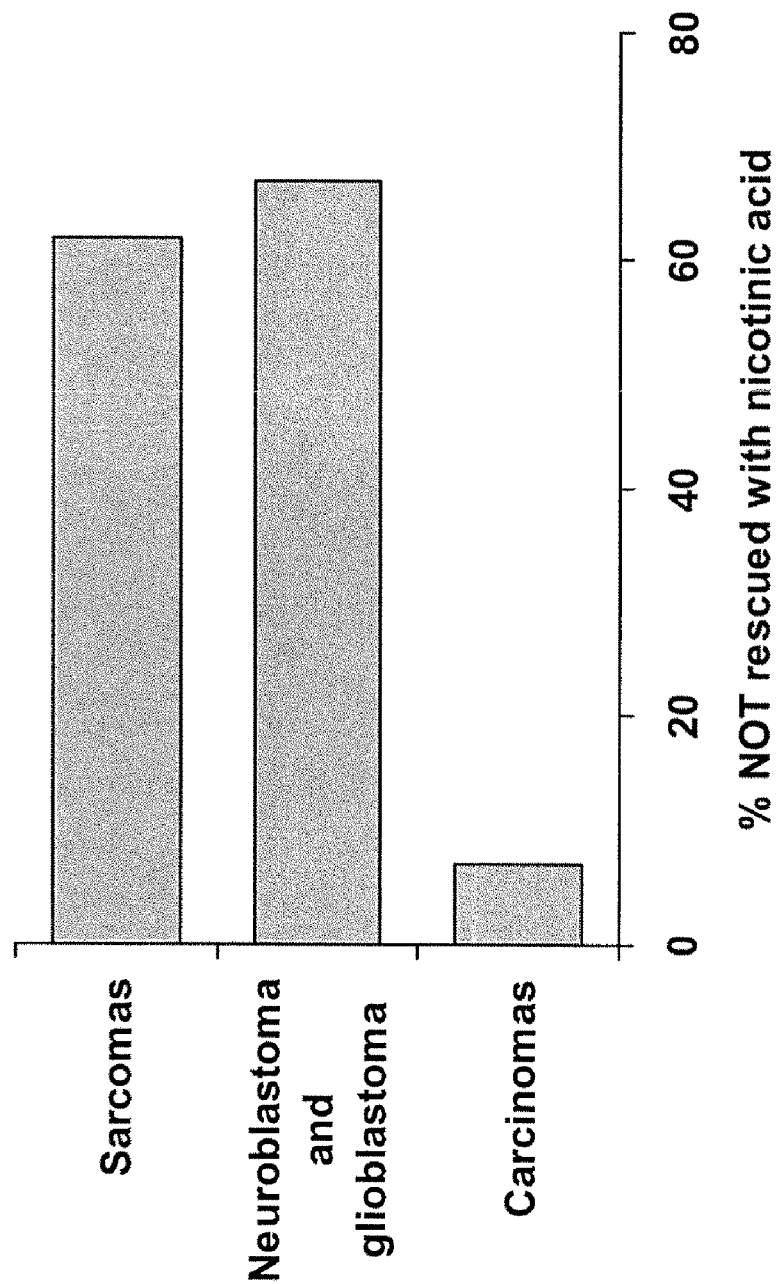
FIG. 8 is a graphic representation that shows the fraction of tested cell lines of a given cancer type that were not rescued by nicotinic acid, indicating that these cancer cell lines are deficient in nicotinic acid pathway.

Different cancer cell lines were treated with increasing concentrations of a NMPRT inhibitor (Compound 1) in the absence or presence of 0.01, 0.1 and 1 mM nicotinic acid (niacin). FIG. 8 shows the fraction of cell lines that were not rescued from Compound 1 induced cytotoxicity by administration of nicotinic acid.

Out of 13 sarcoma cell lines tested, 8 of them were not rescued by nicotinic acid, yielding a percentage of 60% of sarcomas not being rescued. The sarcoma cell lines that were not rescued were: Hs821.T giant cell sarcoma, MES-SA uterine sarcoma, U-2OS osteosarcoma, HT1080 fibrosarcoma, GCT MFH histiocytoma, SW1353 chondrosarcoma, A204 rhabdomyosarcoma, and MG-63 osteosarcoma.

Two out of three cell lines for the neuroblastoma and glioblastoma were also not rescued by nicotinic acid from Compound 1 induced cytotoxicity. The neuroblastoma and glioblastoma cell lines that were not rescued by nicotinic acid were IMR32 and T98G, respectively. Fourteen other carcinomas were tested and only the colon cancer cell line Colo320DM was not rescued by nicotinic acid.

7.15 Example 13

In Vivo Activity of a NMPRT Inhibitor and Nicotinic Acid Against a Cancer that is not Deficient in Nicotinic Acid Pathway To demonstrate the in vivo effect of nicotinic acid on the antitumor activity of a NMPRT inhibitor (Compound 2) on tumors that are not deficient in nicotinic acid pathway, experiments were conducted in CB17 SCID mice (Charles River; Saint Constant, Canada), which were injected with human multiple myeloma IM-9 cancer cells.

Human multiple myeloma IM-9 cancer cells were maintained in RPMI (Hyclone, Utah, USA) supplemented with 10% inactivated fetal bovine serum (Bio-Whittaker; MD, USA) and 1% penicillin-streptomycin-L-Glutamine (Gibco; NY, USA), under 5% CO$_2$ at 37° C. IM-9 cells were transplanted subcutaneously into the flank of female mice. Each mouse was inoculated with a suspension of 10×10$^6$ tumors cells per 100 µl in PBS on day zero. There were three treatment groups of eight mice each: (a) a control group; (b) a group treated with Compound 2; and (c) a group treated with Compound 2 and nicotinic acid.

Treatments started on day eight after IM-9 cells transplantation. Compound 2 was administered intravenously (IV) for 24 hours infusion at a dose of 150 mg/kg followed by: (a) 80 hours infusion of 0.9% NaCl for the groups treated with Compound 2; or (b) 4 hours infusion of nicotinic acid at 120 mg/kg followed by a 76 hour infusion of 0.9% NaCl for the groups treated with Compound 2 and nicotinic acid. The control group was treated with vehicle (0.9% NaCl) alone for 104 hours. Treatments were conducted using Lomir External pump (Lomir Biomedical; Quebec, Canada)-Model 220 with a flow rate of 50 µL/hr (~2.5 mL/kg/hr) and equipped with 1 cc syringes (Becton Dickenson; Cat No. 309571) for treated groups or equipped with 10 cc syringes (Becton Dickenson; Cat No. 406078) for the control group. Compound 2 was prepared fresh for dosing and formulated in a vehicle solution of 10 mM citrate buffer at pH 4.8. Nicotinic acid (niacin) (Sigma-Aldrich; St. Louis, Mo.; Cat No: N4126-100G) was prepared fresh for dosing and formulated in 5% Dextrose USP.

Figure 9:
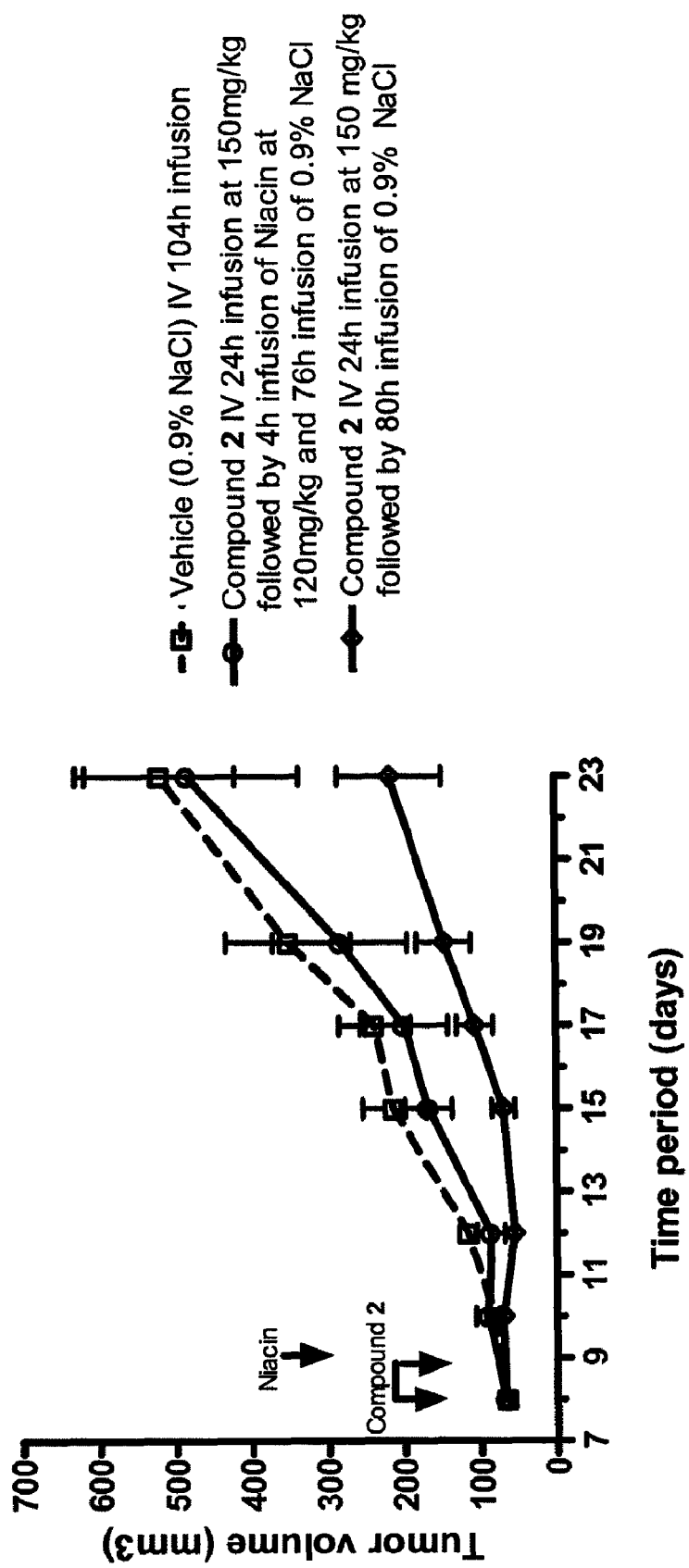
FIG. 9 is a graphic representation that shows the effects of administration of a NMPRT inhibitor (Compound 2) and nicotinic acid (niacin) on tumor size in mice injected with human multiple myeloma IM-9 cancer cells at the NMPRT inhibitor dosage of 150 mg/kg.

Observation continued for 23 days after initial tumor implantation. As shown in FIG. 9, Compound 2 treatment at a dose of 150 mg/kg for 24 hours resulted in a statistically significant reduction in tumor growth compared to the mice treated with vehicle only. The treatment with nicotinic acid at a dose of 120 mg/kg for 4 hours was able to inhibit the anti-tumor activity of Compound 2 in mice that are used as a model for a human with multiple myeloma.

Therefore, cancers that are not deficient in the nicotinic acid pathway are rescued from NMPRT inhibitor-induced cytotoxicity when treated with NMPRT inhibitor in the presence of nicotinic acid.

7.17 Example 14

In Vivo Activity of a NMPRT Inhibitor and Nicotinic Acid Against a Cancer Deficient in Nicotinic Acid Pathway Human Fibrosarcoma HT1080 cancer cells were maintained in RPMI (Hyclone, Utah, USA) supplemented with 10% inactivated fetal bovine serum (Bio-Whittaker, MD, USA) and 1% penicillin-streptomycin-L-Glutamine (Gibco; NY, USA), under 5% $CO_2$ at 37° C. HT1080 cells were transplanted subcutaneously into the flank of female mice. Each mouse was inoculated with a suspension of $1 \times 10^6$ tumors cells per 100 μl in PBS on day zero. There were five treatment groups of seven mice each: (a) a control group; (b) two groups treated with Compound 2; and (c) two groups treated with Compound 2 and nicotinic acid.

Treatments started on day fifteen after HT1080 cells transplantation. Compound 2 was administered intravenously (IV) for 24 hours infusion at a dose of 150 mg/kg (FIG. 10) or 650 mg/kg (FIG. 11) followed by: (a) 80 hours infusion of 0.9% NaCl for the groups treated with Compound 2; or (b) 4 hours infusion of nicotinic acid at 120 mg/kg followed by a 76 hour infusion of 0.9% NaCl for the groups treated with Compound 2 and nicotinic acid. The control group was treated with vehicle (0.9% NaCl) alone for 104 hours. Treatments were conducted using Lomir External pump-Model 220 with a flow rate of 50 μL/hr (2.5 mL/kg/hr) and equipped with 1 cc syringes for treated groups or equipped with 10 cc syringes for the control group. Compound 2 was prepared fresh for dosing and formulated in a vehicle solution of 10 mM citrate buffer at pH 4.8. Nicotinic acid (niacin) was prepared fresh for dosing and formulated in 5% Dextrose USP.

Observation continued for 22 days after initial tumor implantation. As shown in FIG. 10, Compound 2 treatment at a dose of 150 mg/kg for 24 hours resulted in a statistically significant reduction in tumor growth compared to the mice treated with vehicle only, and the treatment with niacin at a dose of 120 mg/kg for 4 hours appeared to be unable to inhibit the anti-tumor activity of Compound 2. Treatment with Compound 2 at higher dose of 650 mg/kg resulted in the mortality of a mouse in this treatment group. Treatment with Compound 2 at a dose of 650 mg/kg also resulted in a significant reduction in tumor growth as compared to mice treated with vehicle only and treatment with niacin at a dose of 120 mg/kg for 4 hours did not inhibit the anti-tumor activity of Compound 2 (FIG. 11). Hence, nicotinic acid was unable to rescue the human fibrosarcoma HT1080 cancer cells from the anti-tumor activity of Compound 2.

Therefore, cancers that are deficient in the nicotinic acid pathway can be treated with higher concentration of a NMPRT inhibitor in the presence of nicotinic acid. As the data show, nicotinic acid improves tolerance of mice to the NMPRT inhibitor without affecting its anti-tumor activity. As FIG. 11 shows, administration of a higher dosage of the NMPRT inhibitor, made possible by co-administration of nicotinic acid, leads to greater reduction of tumor volume than a lower dosage. Therefore, the combination of NMPRT inhibitor and nicotinic acid improves the therapeutic index (also known as the therapeutic ratio) of a NMPRT inhibitor.

7.18 Example 15

Immunohistochemisty Analysis for NAPRT1 Expression in Several Cancer and Normal Tissue Microarrays Formalin fixed paraffin embedded human cancer and normal tissue sections were analysed for NAPRT1 (NAPRT) expression by immunohistochemical screening of commercially available tissue microarray (TMA) slides from US Biomax Inc. (Rockville, Md. USA). Carcinoma samples were from arrays MC803 and MC804. Lymphoma samples were from arrays LYM1501, LYM802 and NHL801. Sarcoma samples were from array SO801 Brain glioblastoma samples were from arrays BS17018, GL801 and GL802. CLL samples were from arrays donated by Miguel Piris (Molecular Pathology Program, Centro Nacional de Investigaciones Oncológicas, Madrid Spain). Normal tissue samples were from arrays BN00011 and SK243. For NAPRT1 (NAPRT) expression analysis, tumor array slides (5 μM sections) were baked at 60° C. for 2 h and deparaffinized in xylene then rehydrated. Antigen retrieval using Antigen Unmasking Solution, High pH (Vector Labs, Burlingame Calif., USA) was followed by endogenous peroxidase inactivation with 3% hydrogen peroxide (Sigma-Aldritch Corp., St. Louis Mo., USA). Slides were blocked for 1 h at room temperature with TSA blocking solution (Perkin Elmer, Waltham Mass., USA) then incubated with 1:5000 dilution of purified rabbit polyclonal NAPRT1 (NAPRT) antibody (Proteintech Group Inc., Chicago Ill., USA) or 1:5000 dilution of purified rabbit IgG (Sigma-Aldritch Corp., St. Louis Mo., USA) in CanGet Signal Immunoreaction Enhancer Solution 1 (Cosmo Bio Co. Ltd., Tokyo Japan) for 36 h at 4° C. in a humidified chamber. Slides were incubated with a 1:1000 dilution of goat anti-rabbit HRP (Jackson ImmunoResearch Labs, West Grove Pa., USA) in PBS for 30 min at room temperature. Signal amplification using the TSA kit (Perkin Elmer, Waltham Mass., USA) was per the manufacturer's instructions followed by incubation with Vectastain ABC reagent (Vector Labs, Burlingame Calif., USA) for 30 min at room temperature. Colorimetric detection was performed using the Peroxidase substrate DAB (Vector Labs, Burlingame Calif., USA). Slides were mounted with Permount (ThermoFisher Scientific, Waltham Mass., USA) and scanned using a Nanozoomer instrument (Olympus Inc., Center Valley Pa., USA). Tissue sections were scored for specific NAPRT1 (NAPRT) expression by comparison of sections stained with anti-NAPRT1 (NAPRT) compared to sequential sections stained with a pre-immune rabbit IgG to assess non-specific staining. Scoring was assessed by an independent pathologist. Data are presented as number of sections scoring positive, negative or equivocal. As FIG. 12 shows, CCL is a cancer that is deficient in the nicotinic acid pathway and can be treated with a NMPRT inhibitor.

Equivalents: those skilled in the art will recognize, or be able to ascertain, using no more than routine experimentation, numerous equivalents to the specific embodiments described specifically herein. Such equivalents are intended to be encompassed in the scope of the following claims.

A number of references have been cited, the entire disclosures of which have been incorporated herein in their entirety.

What is claimed is:

1. A method for treating a patient diagnosed with or suspected to have chronic lymphocytic leukemia (CLL) comprising administering to the patient:

(a) an effective amount of a nicotinamide phosphoribosyl transferase inhibitor of the formula Ia

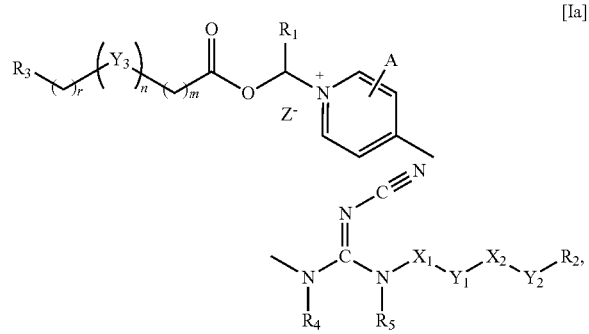

the formula Ib

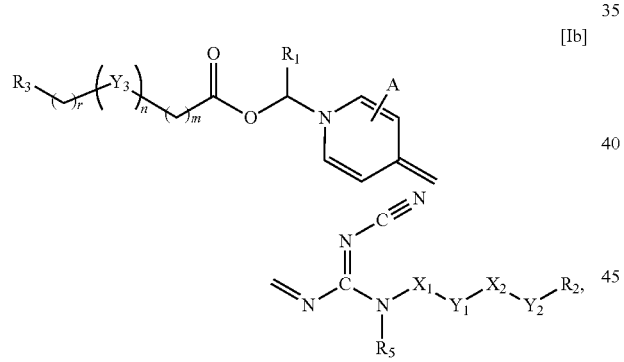

the formula II

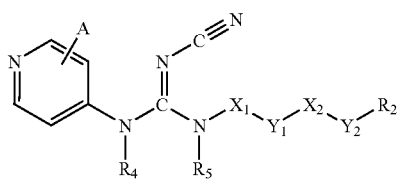

or a pharmaceutically acceptable salt thereof, wherein $X_1$ and $X_2$ are independently a bond, a straight, branched and/or cyclic hydrocarbon diradical which is unsubstituted or substituted with one or more hydroxy, halogen, nitro, amino, cyano, aminosulfonyl, alkylsulfonylamino, alkylcarbonyl, formyl, aminocarbonyl or alkylcarbonylamino; a heteroarylene or non-aromatic heterocyclic hydrocarbon diradical, each of which is unsubstituted or substituted with one or more straight, branched and/or cyclic non-aromatic hydrocarbon radical, hydroxyl, halogen, amino, nitro, cyano, aminosulfonyl, alkylsulfonylamino, alkylcarbonyl, formyl, aminocarbonyl or alkylcarbonylamino;

each $Y_1$ and $Y_2$ is independently a bond, an ether diradical (R'—O—R''), an amine diradical (R'—N—R''), O, S, S(O), S(O)$_2$, C(O), NH—CO, CO—NH, SO$_2$—N(R'), methylene or N(R')—SO$_2$ wherein R' and R'' are independently a straight or branched hydrocarbon diradical containing 1-4 carbon atoms;

$Y_3$ is O, O—C(O), C(O)—O, or N(R$_8$); R$_8$ is hydrogen or $C_{1-4}$ alkyl;

$R_1$ is hydrogen or straight, branched and/or cyclic alkyl, all of which other than hydrogen are unsubstituted or substituted with phenyl; aryl; aralkyl; or an aromatic hydrocarbon radical;

$R_2$ is aryl, heteroaryl or a non-aromatic heterocyclic hydrocarbon radical, tetrahydropyranyloxy, di-(C$_{1-4}$ alkoxy) phosphinoyloxy and $C_{1-4}$ alkoxycarbonylamino, all of which can be unsubstituted or substituted with one or more of halogen, trifluoromethyl, hydroxy, $C_{1-4}$ alkoxy, $C_{1-4}$ alkoxycarbonyl, nitro, cyano, amino, aminocarbonyl, sulfamoyl, $C_{1-4}$ alkyl or $C_{1-4}$ hydroxyalkyl, wherein the $C_{1-4}$ alkyl and $C_{1-4}$ hydroxyalkyl are unsubstituted or substituted with one or more of halogen, hydroxyl, cyano or nitro;

$R_3$ is hydrogen, a straight, branched and/or cyclic hydrocarbon radical, all of which other than hydrogen can be substituted with one or more amino, hydroxy, carboxy, halogen, nitro, cyano, alkoxy, aminocarbonyl, $C_{1-4}$ alkoxycarbonyl, $C_{1-4}$ alkoxycarbonylamino, sulfo, hydroxysulfonyloxy, dihydroxyphosphinoyloxy, phosphono, sulfamino, aminosulfonyl, aminoacylamino or dialkoxyphosphinoyl; heteroaryl or a non-aromatic heterocyclic hydrocarbon radical, all of which can be substituted with one or more straight, branched and/or cyclic hydrocarbon radical, amino, hydroxy, carboxy, halogen, nitro, cyano, alkoxy, aminocarbonyl, $C_{1-4}$ alkoxycarbonyl, $C_{1-4}$ alkoxycarbonylamino, sulfo, hydroxysulfonyloxy, dihydroxyphosphinoyloxy, phosphono, sulfamino, aminosulfonyl, aminoacylamino or dialkoxyphosphinoyl;

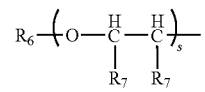

wherein s is an integer from 1 to 200; $R_6$ is hydrogen or a non-aromatic hydrocarbon radical which is unsubstituted or substituted with hydroxyl, halogen, amino, nitro, cyano, aminosulfonl, alkylsulfonylamino, alkylcarbonyl, formyl, aminocarbonyl or alkylcarbonylamino; each $R_7$ is independently hydrogen or methyl;

each $R_4$ and $R_5$ is independently represent hydrogen; a straight, branched and/or cyclic hydrocarbon radical, all of which other than hydrogen can be substituted with one or more of halogen, hydroxyl, halogen, amino, nitro or cyano;

A represents hydrogen, an substituted or unsubstituted straight, branched and/or cyclic hydrocarbon radical, hydroxy, halogen, nitro, cyano, heteroaryl, heteroaralkyl or thiol;

Z⁻ is a pharmaceutically acceptable anion;
each m and r is independently an integer from 0 to 4; and n is 0 or 1; and
(b) an effective amount of nicotinic acid.

2. The method of claim 1, wherein the compound of formula Ia, Ib, or II is:
1-[2-(2-(2-Methoxyethoxy)-ethoxy)-ethoxy-carbonyloxymethyl]-4-[N'-cyano-N"-(6-(4-chlorophenoxy)-hexyl)-N-guanidino]-pyridinium chloride;
1-[2-(2-Methoxyethoxy)-ethoxy-carbonyloxymethyl]-4-[N'-cyano-N"-(6-(4-chlorophenoxy)-hexyl)-N-guanidino]-pyridinium chloride;
1-[2-Methoxyethoxy)-carbonyloxymethyl]-4-[N'-cyano-N"-(6-(4-chlorophenoxy)-hexyl)-N-guanidino]-pyridinium chloride;
1-[2-(2-(2-Methoxyethoxy)-ethoxy)-ethoxy-carbonyloxymethyl]-4-[N'-cyano-N"-(6-(4-chlorophenoxy)-hexyl)-N-guanidino]-pyridinium iodide;
N-[1-(2-(2-(2-Methoxyethoxy)-ethoxy)-ethoxycarbonyloxymethyl)-1,4-dihydropyridin-4-ylidene]-N'-cyano-N"-(6-(4-chlorophenoxy)-hexyl)-guanidine;
1-[2-(2-(2-Methoxyethoxy)-ethoxy)-ethoxy-carbonyloxymethyl]-4-[N'-cyano-N"-(6-(4-chlorophenoxy)-hexyl)-N-guanidino]-pyridinium chloride;
1-[1-(2-(2-Methoxyethoxy)-ethoxy-carbonyloxy)-ethyl]-4-[N'-cyano-N"-(6-(4-chlorophenoxy)-hexyl)-N-guanidino]-pyridinium chloride;
1-[2-(2-(2-Methoxyethoxy)-ethoxy)-ethoxy-acetoxymethyl]-4-[N'-cyano-N"-(6-(4-chlorophenoxy)-hexyl)-N-guanidino]-pyridinium chloride;
1-[2-(2-(2-(2-Methoxyethoxy)-ethoxy)-ethoxy-ethoxycarbonyloxymethyl]-4-[N'-cyano-N"-(6-(4-chlorophenoxy)-hexyl)-N-guanidino]-pyridinium chloride;
1-Pivaloyloxymethyl-4-[N'-cyano-N"-(6-(4-chlorophenoxy)-hexyl)-N-guanidino]-pyridinium chloride;
1-Acetoxymethyl-4-[N'-cyano-N"-(6-(4-chlorophenoxy)-hexyl)-N-guanidino]-pyridinium chloride;
1-(L)-Valyloxymethyl-4-[N'-cyano-N"-(6-(4-chlorophenoxy)-hexyl)-N-guanidino]-pyridinium chloride;
1-Glycyloxymethyl-4-[N'-cyano-N"-(6-(4-chlorophenoxy)-hexyl)-N-guanidino]-pyridinium chloride;
1-[Monobenzyl succinyloxymethyl]-4-[N'-cyano-N"-(6-(4-chlorophenoxy)-hexyl)-N-guanidino]-pyridinium chloride;
1-[2-(2-(2-(2-(2-Methoxyethoxy)-ethoxy)-ethoxy)-ethoxy carbonyloxymethyl]-4-[N'-cyano-N"-(6-(4-chlorophenoxy)-hexyl)-N-guanidino]-pyridinium chloride;
1-[2-(2-(2-(2-(2-Methoxyethoxy)-ethoxy)-ethoxy)-ethoxy-ethoxy-ethoxy-carbonyloxymethyl]-4-[N'-cyano-N"-(6-(4-chlorophenoxy)-hexyl)-N-guanidino]-pyridinium chloride;
1-[2-(2-(2-Methoxyethoxy)-ethoxy)-ethoxy-carbonyloxymethyl]-4-[N'-cyano-N"-(9-(diethoxyphosphinoyloxy)-nonyl)-N-guanidino]-pyridinium chloride;
1-[2-(2-(2-Methoxyethoxy)-ethoxy)-ethoxy)-carbonyloxymethyl]-4-[N'-cyano-N"-(12-(tert-butyloxycarbonylamino)-dodecyl)-N-guanidino]-pyridinium iodide;
1-[2-(2-(2-Methoxyethoxy)-ethoxy)-ethoxy)-carbonyloxymethyl]-4-[N'-cyano-N"-(12-(tert-butyloxycarbonylamino)-dodecyl)-N-guanidino]-pyridinium chloride;
1-[2-(2-(2-(2-Methoxyethoxy)-ethoxy)-ethoxy)-ethoxy-carbonyloxymethyl]-4-[N'-cyano-N"-(12-(tert-butyloxycarbonylamino)-dodecyl)-N-guanidino]-pyridinium chloride;
1-[3-(N-tert-butoxycarbonylamino)-propyloxy-carbonyloxymethyl]-4-[N'-cyano-N"-(6-(4-chlorophenoxy)-hexyl)-N-guanidino]-pyridinium iodide;
1-[3-Amino-propyloxy-carbonyloxymethyl]-4-[N'-cyano-N"-(6-(4-chlorophenoxy)-hexyl)-N-guanidino]-pyridinium chloride;
1-[3-(N-tert-butoxycarbonylamino)-propyl-carbamoyloxymethyl]-4-[N'-cyano-N"-(6-(4-chlorophenoxy)-hexyl)-N-guanidino]-pyridinium iodide;
1-[3-Aminopropyl-carbamoyloxymethyl]-4-[N'-cyano-N"-(6-(4-chlorophenoxy)-hexyl)-N-guanidino]-pyridinium chloride;
1-[5-(N-tert-butoxycarbonylamino)-pentanoyloxymethyl]-4-[N'-cyano-N"-(6-(4-chlorophenoxy)-hexyl)-N-guanidino]-pyridinium iodide;
1-[5-Amino-pentanoyloxymethyl]-4-[N'-cyano-N"-(6-(4-chlorophenoxy)-hexyl)-N-guanidino]-pyridinium chloride;
1-[3-(tert-butoxycarbonyl)-propionyloxymethyl]-4-[N'-cyano-N"-(6-(4-chlorophenoxy)-hexyl)-N-guanidino]-pyridinium chloride;
1-[3-carboxy-propionyloxymethyl]-4-[N'-cyano-N"-(6-(4-chlorophenoxy)-hexyl)-N-guanidino]-pyridinium chloride;
1-[N-(tert-butoxycarbonylmethyl)-carbamoyloxymethyl]-4-[N'-cyano-N"-(6-(4-chlorophenoxy)-hexyl)-N-guanidino]-pyridinium iodide;
1-[N-(carboxymethyl)-carbamoyloxymethyl]-4-[N'-cyano-N"-(6-(4-chlorophenoxy)-hexyl)-N-guanidino]-pyridinium chloride;
1-[1-(tert-butoxycarbonyl)-4-piperidyloxy-carbonyloxymethyl]-4-[N'-cyano-N"-(6-(4-chlorophenoxy)-hexyl)-N-guanidino]-pyridinium iodide;
1-[4-Piperidyloxy-carbonyloxymethyl]-4-[N'-cyano-N"-(6-(4-chloro-phenoxy)-hexyl)-N-guanidino]-pyridinium chloride;
1-[tert-butoxycarbonylmethoxy-carbonyloxymethyl]-4-[N'-cyano-N"-(6-(4-chlorophenoxy)-hexyl)-N-guanidino]-pyridinium iodide;
1-[Carboxymethoxy-carbonyloxymethyl]-4-[N'-cyano-N"-(6-(4-chlorophenoxy)-hexyl)-N-guanidino]-pyridinium chloride;
N-[1-(α-(2-(2-(2-Methoxyethoxy)-ethoxy)-ethoxycarbonyloxy)benzyl)-1,4-dihydropyridin-4-ylidene]-N'-cyano-N"-(6-(4-chlorophenoxy)-hexyl)-guanidine;
4-[N'-cyano-N"-(6-(4-chlorophenoxy)-hexyl)-N-guanidino]-pyridine;
4-[N'-cyano-N"-(9-(diethoxyphosphinoyloxy)-nonyl)-N-guanidino]-pyridine;
4-[N'-cyano-N"-(12-(tert-butyloxycarbonylamino)-dodecyl)-N-guanidino]-pyridine;
or a pharmaceutically acceptable salt thereof.

3. The method of claim 2, wherein the compound is 1-[2-(2-(2-Methoxyethoxy) -ethoxy)-ethoxy)-ethoxy-carbonyloxymethyl]-4-[N'-cyano-N"-(6-(4-chlorophenoxy)-hexyl)-N-guanidino]-pyridinium chloride, 4-[N'-cyano-N"-(6-(4-chlorophenoxy)-hexyl)-N-guanidino]-pyridine, or a pharmaceutically acceptable salt thereof.

4. A method for treating a patient diagnosed with or suspected to have chronic lymphocytic leukemia (CLL) comprising administering to the patient:
(a) an effective amount of (E)-N-[4-(1-benzoylpiperidin-4-yl)butyl]-3-(pyridin-3-yl)acrylamide; and
(b) an effective amount of nicotinic acid.

5. The method selected from any one of claims 1-4, wherein the effective amount of nicotinic acid is administered intravenously or orally.

6. A method for treating a patient diagnosed with or suspected to have chronic lymphocytic leukemia (CLL) comprising administering to the patient:
(a) an effective amount of a nicotinamide phosphoribosyl transferase inhibitor of the formula Ia

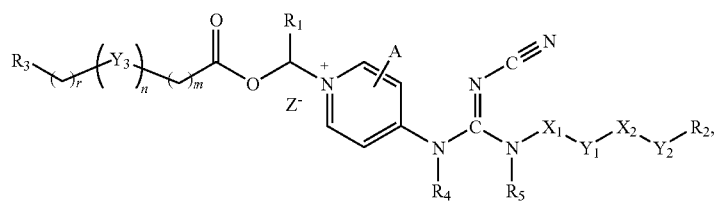

[Ia]

the formula Ib

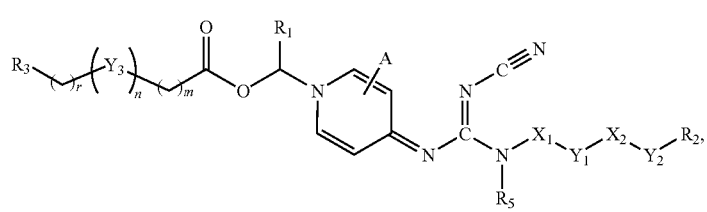

[Ib]

, formula II

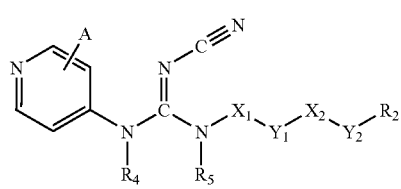

[II]

or a pharmaceutically acceptable salt thereof,
wherein $X_1$ and $X_2$ are independently a bond, a straight, branched and/or cyclic hydrocarbon diradical which is unsubstituted or substituted with one or more hydroxy, halogen, nitro, amino, cyano, aminosulfonyl, alkylsulfonylamino, alkylcarbonyl, formyl, aminocarbonyl or alkylcarbonylamino; a heteroarylene or non-aromatic heterocyclic hydrocarbon diradical, each of which is unsubstituted or substituted with one or more straight, branched and/or cyclic non-aromatic hydrocarbon radical, hydroxyl, halogen, amino, nitro, cyano, aminosulfonyl, alkylsulfonylamino, alkylcarbonyl, formyl, aminocarbonyl or alkylcarbonylamino;

each $Y_1$ and $Y_2$ is independently a bond, an ether diradical (R'—O—R"), an amine diradical (R'—N—R"), O, S, S(O), S(O)$_2$, C(O), NH—CO, CO—NH, SO$_2$—N(R'), methylene or N(R')—SO$_2$ wherein R' and R" are independently a straight or branched hydrocarbon diradical containing 1-4 carbon atoms;

$Y_3$ is O, O—C(O), C(O)—O, or N(R$_8$); R$_8$ is hydrogen or $C_{1-4}$ alkyl;

$R_1$ is hydrogen or straight, branched and/or cyclic alkyl, all of which other than hydrogen are unsubstituted or substituted with phenyl; aryl; aralkyl; or an aromatic hydrocarbon radical;

$R_2$ is aryl, heteroaryl or a non-aromatic heterocyclic hydrocarbon radical, tetrahydropyranyloxy, di-($C_{1-4}$ alkoxy) phosphinoyloxy and $C_{1-4}$ alkoxycarbonylamino, all of which can be unsubstituted or substituted with one or more of halogen, trifluoromethyl, hydroxy, $C_{1-4}$ alkoxy, $C_{1-4}$ alkoxycarbonyl, nitro, cyano, amino, aminocarbonyl, sulfamoyl, $C_{1-4}$ alkyl or $C_{1-4}$ hydroxyalkyl, wherein the $C_{1-4}$ alkyl and $C_{1-4}$ hydroxyalkyl are unsubstituted or substituted with one or more of halogen, hydroxyl, cyano or nitro;

$R_3$ is hydrogen, a straight, branched and/or cyclic hydrocarbon radical, all of which other than hydrogen can be substituted with one or more amino, hydroxy, carboxy, halogen, nitro, cyano, alkoxy, aminocarbonyl, $C_{1-4}$ alkoxycarbonyl, $C_{1-4}$ alkoxycarbonylamino, sulfo, hydroxysulfonyloxy, dihydroxyphosphinoyloxy, phosphono, sulfamino, aminosulfonyl, aminoacylamino or dialkoxyphosphinoyl; heteroaryl or a non-aromatic heterocyclic hydrocarbon radical, all of which can be substituted with one or more straight, branched and/or cyclic hydrocarbon radical, amino, hydroxy, carboxy, halogen, nitro, cyano, alkoxy, aminocarbonyl, $C_{1-4}$ alkoxycarbonyl, $C_{1-4}$ alkoxycarbonylamino, sulfo, hydroxysulfonyloxy, dihydroxyphosphinoyloxy, phosphono, sulfamino, aminosulfonyl, aminoacylamino or dialkoxyphosphinoyl;

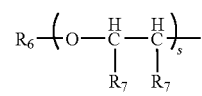

wherein s is an integer from 1 to 200; $R_6$ is hydrogen or a non-aromatic hydrocarbon radical optionally substituted with hydroxyl, halogen, amino, nitro, cyano, aminosulfonl, alkylsulfonylamino, alkylcarbonyl, formyl, aminocarbonyl or alkylcarbonylamino; each $R_7$ is independently hydrogen or methyl;

each $R_4$ and $R_5$ is independently represent hydrogen; a straight, branched and/or cyclic hydrocarbon radical, all of which other than hydrogen can be substituted with one or more of halogen, hydroxyl, halogen, amino, nitro or cyano;

A represents hydrogen, an substituted or unsubstituted straight, branched and/or cyclic hydrocarbon radical, hydroxy, halogen, nitro, cyano, heteroaryl, heteroaralkyl or thiol;

$Z^-$ is a pharmaceutically acceptable anion;

each m and r is independently an integer from 0 to 4; and n is 0 or 1;

(b) an effective amount of nicotinic acid; and (c) DNA damaging therapy.

7. The method of claim 6, wherein the compound of formula Ia, Ib, or II is:

1-[2-(2-(2-Methoxyethoxy)-ethoxy)-ethoxy-carbonyloxymethyl]-4-[N'-cyano-N"-(6-(4-chlorophenoxy)-hexyl)-N-guanidino]-pyridinium chloride;

1-[2-(2-Methoxyethoxy)-ethoxy-carbonyloxymethyl]-4-[N'-cyano-N"-(6-(4-chlorophenoxy)-hexyl)-N-guanidino]-pyridinium chloride;

1-[2-Methoxyethoxy)-carbonyloxymethyl]-4-[N'-cyano-N"-(6-(4-chlorophenoxy)-hexyl)-N-guanidino]-pyridinium chloride;

1-[2-(2-(2-Methoxyethoxy)-ethoxy)-ethoxy-carbonyloxymethyl]-4-[N'-cyano-N"-(6-(4-chlorophenoxy)-hexyl)-N-guanidino]-pyridinium iodide;

N-[1-(2-(2-(2-Methoxyethoxy)-ethoxy)-ethoxycarbonyloxymethyl)-1,4-dihydropyridin-4-ylidene]-N'-cyano-N"-(6-(4-chlorophenoxy)-hexyl)-guanidine;

1-[2-(2-(2-Methoxyethoxy)-ethoxy)-ethoxy-carbonyloxymethyl]-4-[N'-cyano-N"-(6-(4-chlorophenoxy)-hexyl)-N-guanidino]-pyridinium chloride;

1-[1-(2-(2-Methoxyethoxy)-ethoxy-carbonyloxy)-ethyl]-4-[N'-cyano-N"-(6-(4-chlorophenoxy)-hexyl)-N-guanidino]-pyridinium chloride;

1-[2-(2-(2-Methoxyethoxy)-ethoxy)-ethoxy-acetoxymethyl]-4-[N'-cyano-N"-(6-(4-chlorophenoxy)-hexyl)-N-guanidino]-pyridinium chloride;

1-[2-(2-(2-(2-Methoxyethoxy)-ethoxy)-ethoxy)-ethoxycarbonyloxymethyl]-4-[N'-cyano-N"-(6-(4-chlorophenoxy)-hexyl)-N-guanidino]-pyridinium chloride;

1-Pivaloyloxymethyl-4-[N'-cyano-N"-(6-(4-chlorophenoxy)-hexyl)-N-guanidino]-pyridinium chloride;

1-Acetoxymethyl-4-[N'-cyano-N"-(6-(4-chlorophenoxy)-hexyl)-N-guanidino]-pyridinium chloride;

1-(L)-Valyloxymethyl-4-[N'-cyano-N"-(6-(4-chlorophenoxy)-hexyl)-N-guanidino]-pyridinium chloride;

1-Glycyloxymethyl-4-[N'-cyano-N"-(6-(4-chlorophenoxy)-hexyl)-N-guanidino]-pyridinium chloride;

1-[Monobenzyl succinyloxymethyl]-4-[N'-cyano-N"-(6-(4-chlorophenoxy)-hexyl)-N-guanidino]-pyridinium chloride;

1-[2-(2-(2-(2-(2-Methoxyethoxy)-ethoxy)-ethoxy)-ethoxy)-ethoxy carbonyloxymethyl]-4-[N'-cyano-N"-(6-(4-chlorophenoxy)-hexyl)-N-guanidino]-pyridinium chloride;

1-[2-(2-(2-(2-(2-Methoxyethoxy)-ethoxy)-ethoxy)-ethoxy-ethoxy-ethoxy-carbonyloxymethyl]-4-[N'-cyano-N"-(6-(4-chlorophenoxy)-hexyl)-N-guanidino]-pyridinium chloride;

1-[2-(2-(2-Methoxyethoxy)-ethoxy)-ethoxy-carbonyloxymethyl]-4-[N'-cyano-N"-(9-(diethoxyphosphinoyloxy)-nonyl)-N-guanidino]-pyridinium chloride;

1-[2-(2-(2-Methoxyethoxy)-ethoxy)-ethoxy-carbonyloxymethyl]-4-[N'-cyano-N"-(12-(tert-butyloxycarbonylamino)-dodecyl)-N-guanidino]-pyridinium iodide;

1-[2-(2-(2-Methoxyethoxy)-ethoxy)-ethoxy-carbonyloxymethyl]-4-[N'-cyano-N"-(12-(tert-butyloxycarbonylamino)-dodecyl)-N-guanidino]-pyridinium chloride;

1-[2-(2-(2-(2-Methoxyethoxy)-ethoxy)-ethoxy)-ethoxy-carbonyloxymethyl]-4-[N'-cyano-N"-(12-(tert-butyloxycarbonylamino)-dodecyl)-N-guanidino]-pyridinium chloride;

1-[3-(N-tert-butoxycarbonylamino)-propyloxy-carbonyloxymethyl]-4-[N'-cyano-N"-(6-(4-chlorophenoxy)-hexyl)-N-guanidino]-pyridinium iodide;

1-[3-Amino-propyloxy-carbonyloxymethyl]-4-[N'-cyano-N"-(6-(4-chlorophenoxy)-hexyl)-N-guanidino]-pyridinium chloride;

1-[3-(N-tert-butoxycarbonylamino)-propyl-carbamoyloxymethyl]-4-[N'-cyano-N"-(6-(4-chlorophenoxy)-hexyl)-N-guanidino]-pyridinium iodide;

1-[3-Aminopropyl-carbamoyloxymethyl]-4-[N'-cyano-N"-(6-(4-chlorophenoxy)-hexyl)-N-guanidino]-pyridinium chloride;

1-[5-(N-tert-butoxycarbonylamino)-pentanoyloxymethyl]-4-[N'-cyano-N"-(6-(4-chlorophenoxy)-hexyl)-N-guanidino]-pyridinium iodide;

1-[5-Amino-pentanoyloxymethyl]-4-[N'-cyano-N"-(6-(4-chlorophenoxy)-hexyl)-N-guanidino]-pyridinium chloride;

1-[3-(tert-butoxycarbonyl)-propionyloxymethyl]-4-[N'-cyano-N"-(6-(4-chlorophenoxy)-hexyl)-N-guanidino]-pyridinium chloride;

1-[3-carboxy-propionyloxymethyl]-4-[N'-cyano-N"-(6-(4-chlorophenoxy)-hexyl)-N-guanidino]-pyridinium chloride;

1-[N-(tert-butoxycarbonylmethyl)-carbamoyloxymethyl]-4-[N'-cyano-N"-(6-(4-chlorophenoxy)-hexyl)-N-guanidino]-pyridinium iodide;

1-[N-(carboxymethyl)-carbamoyloxymethyl]-4-[N'-cyano-N"-(6-(4-chlorophenoxy)-hexyl)-N-guanidino]-pyridinium chloride;

1-[1-(tert-butoxycarbonyl)-4-piperidyloxy-carbonyloxymethyl]-4-[N'-cyano-N"-(6-(4-chlorophenoxy)-hexyl)-N-guanidino]-pyridinium iodide;

1-[4-Piperidyloxy-carbonyloxymethyl]-4-[N'-cyano-N"-(6-(4-chloro-phenoxy)-hexyl)-N-guanidino]-pyridinium chloride;

1-[tert-butoxycarbonylmethoxy-carbonyloxymethyl]-4-[N'-cyano-N"-(6-(4-chlorophenoxy)-hexyl)-N-guanidino]-pyridinium iodide;

1-[Carboxymethoxy-carbonyloxymethyl]-4-[N'-cyano-N"-(6-(4-chlorophenoxy)-hexyl)-N-guanidino]-pyridinium chloride;

N-[1-(α-(2-(2-(2-Methoxyethoxy)-ethoxy)-ethoxycarbonyloxy)benzyl)-1,4-dihydropyridin-4-ylidene]-N'-cyano-N"-(6-(4-chlorophenoxy)-hexyl)-guanidine;

4-[N'-cyano-N"-(6-(4-chlorophenoxy)-hexyl)-N-guanidino]-pyridine;

4-[N'-cyano-N"-(9-(diethoxyphosphinoyloxy)-nonyl)-N-guanidino]-pyridine;

4-[N'-cyano-N"-(12-(tert-butyloxycarbonylamino)-dodecyl)-N-guanidino]-pyridine;

or a pharmaceutically acceptable salt thereof.

8. The method of claim 7, wherein the compound is 1-[2-(2-(2-(2-Methoxyethoxy)-ethoxy)-ethoxy)-ethoxy-carbonyloxymethyl]-4-[N'-cyano-N"-(6-(4-chlorophenoxy)-hexyl)-N-guanidino]-pyridinium chloride, 4-[N'-cyano-N"-(6-(4-chlorophenoxy)-hexyl)-N-guanidino]-pyridine, or a pharmaceutically acceptable salt thereof.

9. A method for treating a patient diagnosed with or suspected to have chronic lymphocytic leukemia (CLL) comprising administering to the patient:

(a) an effective amount of (E)-N-[4-(1-benzoylpiperidin-4-yl)butyl]-3-(pyridin-3-yl)acrylamide;

(b) an effective amount of nicotinic acid; and (c) DNA damaging therapy.

10. The method of any one of claims 6-9, wherein the effective amount of nicotinic acid is administered intravenously or orally.

11. The method of any one of claims 6-9, wherein the DNA damaging therapy comprises administering the patient an effective amount of a DNA damaging chemotherapeutic agent.

12. The method of claim 11, wherein the DNA damaging chemotherapeutic agent is Cladribine, Pentostatin, Methotrexate, Trimetrexate glucuronate, Pemetrexed, Treosulfan, Busulfan, Dacarbazine, Temozolomide, Mitomycin C, Chlorambucil, Ifosfamide, Melphalan, Thiotepa, Mechlorethamine, Carmustine, Bendamustin, Fotemustine, Lomustine, Streptozocin, Carboplatin, Cisplatin, Lobaplatin, Oxaliplatin Bleomycin, Hydroxyurea, Actinomycin D, Azacitidine, Decitabine, Nelarabine, Cytarabine, Fludarabine, Clofarabine, Vorinostat, Gemcitabine, 5-Fluorouracil, Capecitabine, Floxuridine, Raltitrexed, Pemetrexed, Irinotecan, Topotecan, Amrubicin, Daunorubicin, Doxorubicin, Epirubicin, Etoposide, Idarubicin, Mitoxantrone, Teniposide, Valrubicin, Allopurinol, or a pharmaceutically acceptable salt thereof.

* * * * *